United States Patent [19]
Takada et al.

[11] Patent Number: 5,876,756
[45] Date of Patent: Mar. 2, 1999

[54] MICROCAPSULE CONTAINING AMORPHOUS WATER-SOLUBLE 2-PIPERAZINONE-1-ACETIC ACID COMPOUND

[75] Inventors: Shigeyuki Takada; Tomofumi Kurokawa, both of Hyogo; Susumu Iwasa, Kyoto, all of Japan

[73] Assignee: Takeda Chemical Industries, Ltd., Osaka, Japan

[21] Appl. No.: 724,498

[22] Filed: Sep. 30, 1996

Related U.S. Application Data

[63] Continuation-in-part of Ser. No. 535,386, Sep. 28, 1995.

[30] Foreign Application Priority Data

Mar. 29, 1996 [JP] Japan ................................ 8-077012

[51] Int. Cl.[6] ................................................ A61K 9/52
[52] U.S. Cl. .................. 424/489; 424/426; 514/821; 514/822; 514/951; 514/963; 514/964; 264/4.6
[58] Field of Search ..................... 424/426, 451, 424/489; 264/4.32, 4.6; 514/821, 822, 951, 963, 964

[56] References Cited

U.S. PATENT DOCUMENTS

| | | | |
|---|---|---|---|
| 4,954,298 | 9/1990 | Yamamoto et al. | 264/4.6 |
| 5,330,767 | 7/1994 | Yamamoto et al. | 424/497 |
| 5,622,657 | 4/1997 | Takada et al. | 269/4.32 |

FOREIGN PATENT DOCUMENTS

| | | |
|---|---|---|
| 0251476 | 1/1988 | European Pat. Off. . |
| 0350246 | 7/1989 | European Pat. Off. . |
| 0481732 | 4/1992 | European Pat. Off. . |
| 529 858 | 3/1993 | European Pat. Off. . |
| 11009 | 4/1995 | European Pat. Off. . |
| 709 085 | 5/1996 | European Pat. Off. . |
| 9113595 | 9/1991 | WIPO . |

OTHER PUBLICATIONS

J. Pharm. Sciences, vol. 75, No. 8 (1986) 750–755.

*Primary Examiner*—Raj Bawa
*Attorney, Agent, or Firm*—Fitzpatrick, Cella, Harper & Scinto

[57] ABSTRACT

A microcapsule contains a pharmaceutically effective amorphous water-soluble 2-piperazinone-1-acetic acid compound or salt thereof and a polymer binder and a method of preparing said microcapsule. The microcapsule is produced by dispersing in an aqueous phase a dispersion of the amorphous water-soluble 2-piperazinone-1-acetic acid compound or salt thereof in a solution of a polymer in an organic solvent to give an s/o/w type emulsion and subjecting the emulsion to in-water drying. The sustained-release microcapsule entraps 2-piperazinone-1-acetic acid compound or the salt thereof, as a drug, in high concentration, and in reducing the initial release of the drug, thereby reducing undesirable side effects of the drug.

32 Claims, No Drawings

MICROCAPSULE CONTAINING AMORPHOUS WATER-SOLUBLE 2-PIPERAZINONE-1-ACETIC ACID COMPOUND

The application is a continuation-in-part of pending U.S. patent application Ser. No. 08/535,386, field Sep. 28, 1995.

FIELD OF THE INVENTION

This invention relates to a microcapsule containing an amorphous water-soluble 2-piperazinone-1-acetic acid compound or salt thereof and a method of preparing it.

BACKGROUND OF THE INVENTION

Many reports have been made on sustained-release microcapsules of various low-molecular water-soluble drugs [e.g. JPA S57(1982)-118512, J. Pharm. Sci., 75, 750–755 (1986)]. Most of the microcapsules so far reported have the following drawbacks: (1) in the manufacturing process, the amount of the water-soluble drug leaked to the outer aqueous phase is relatively large to result in a relatively low entrapment ratio of the drug, and (2) the resulting microcapsules are generally porous and cause a relatively large initial drug release. Thus, at the present stage, sustained-release of water-soluble drugs over a sufficiently desirable long period have not yet been successfully prepared.

On the other hand, in recent years, novel peptides or low-molecular compounds having excellent cell-adhesion regulating or inhibiting actions have been found and are expected to be used as therapeutic agents of various diseases. For example, compounds having GPIIb/IIIa antagonistic activity remarkably inhibit platelet aggregation or suppress the metastasis of tumor cells and are expected to be clinically useful drugs. (Sci., 233, 467–469 (1986); Sci., 238, 1132–1134 (1987); Proc. Natl. Acad. Sci. USA, 87, 2471–2475(1990)]. As examples of such compounds, linear or cyclic peptides containing the amino acid sequence, -Arg-Gly-Asp-(RGD) have been known [e.g. J. Biol. Chem., 262, 17294–17298 (1987); JPA H2(1990)-174797]. And, non-peptide compounds having an anti-thrombotic activity are disclosed in JPA H4(1992)-264068 and EPA No.505868, in which having 4- to 7-membered cyclic alkyleneimino such as a pyrrolidine ring and compounds having e.g. piperidine ring are respectively described. Further, compounds having piperidinone ring, which have cell-adhesion inhibiting activity, are disclosed in EPA No.529858.

These known compounds are not satisfactory from the viewpoint of the potency of their activity, undesirable side effects (e.g. prolonging bleeding time), absorbability, stability or durability of the action. Circumstances being such as above, there are problems still to be solved for clinical application of these compounds.

Recently, novel 2-piperazinone-1-acetic acid derivatives were synthesized and were found to possess, based on the chemical structural characteristic feature, a potent platelet aggregation inhibiting activity and, at the same time, are safely administrable, i.e. there are few undesirable side effects such as prolongation of bleeding time. These compounds are expected to be applied to a variety of circulatory diseases (e.g. thrombosis, transient cerebral ischemic attack, myocardial infarction, cerebral infarction, peripheral obstruction and arteriosclerotic obliteration), tumors, inflammatory diseases, or prevention of reobstruction and restenosis of coronary arteries after PTCA (percutaneous transluminal coronary angioplasty), prevention of reobstruction and restenosis after surgical operation for coronary artery bypass and secondary prophylaxis after re-opening of infarction. Especially, for patients of chronic diseases, administration of drugs for a long period is required. While preparations capable of sustained-release for a long period are desired, no report on sustained-release microcapsules of the above-mentioned novel compounds has been found.

Exploitation of a method of preparing sustained-release microcapsules which demonstrates a high entrapping ratio of a 2-piperazinone-1-acetic acid compound and a low initial release of the drug is expected.

SUMMARY OF THE INVENTION

The present inventors have diligently studied the above-mentioned problems to find that a microcapsule comprising an amorphous water-soluble 2-piperazinone-1-acetic acid compound and a polymer has a high entrapment of the said compound with a relatively low initial release thereof. Further studies based on this finding have accomplished the present invention.

Namely, the present invention is to provide a microcapsule comprising an amorphous water-soluble 2-piperazinone-1-acetic acid compound, which is a compound of the formula (I):

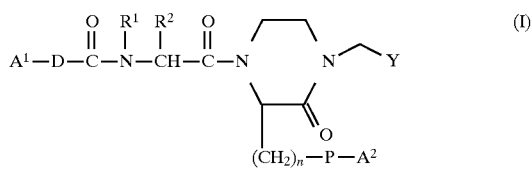

wherein $A^1$ and $A^2$ independently are a proton-accepting group or a group convertible into a proton-accepting group; D is a spacer having a 2- to 6-atom chain optionally bonded through a hetero-atom and/or a 5- or 6-membered ring (provided that the 5- or 6-membered ring is, depending on its bonding position, counted as 2- or 3-atom chain); $R^1$ is a hydrogen atom or a hydrocarbon group; $R^2$ is a hydrogen atom or a residual group formed by removing —CH(NH$_2$) COOH from an α-amino acid, or $R^1$ and $R^2$ may be combined to form a 5- or 6-membered ring; P is a spacer having a 1- to 10-atom chain optionally bonded through a hetero-atom and/or a 5- or 6-membered ring (provided that the 5- or 6-membered ring is, depending on its bonding position, counted as 2- or 3-atom chain); Y is an optionally esterified or amidated carboxyl group; and n denotes an integer of 0 to 8, or salt thereof, [hereinafter sometimes simply referred to as the compound (I)] and a polymer.

The present invention also provides a microcapsule which is prepared by dispersing, in an aqueous phase, a dispersion of an amorphous water-soluble 2-piperazinone-1-acetic acid compound which is a compound of the formula (I) or a salt thereof in a solution of a polymer in an organic solvent to prepare an s/o/w type emulsion and subjecting the emulsion to in-water drying.

The present invention is also to provide a method of preparing a microcapsule, which comprises dispersing, in an aqueous phase, a dispersion of an amorphous water-soluble 2-piperazinone-1-acetic acid compound which is a compound of the formula (I) or a salt thereof in a solution of a polymer in an organic solvent to prepare an s/o/w type emulsion and subjecting the emulsion to in-water drying.

DETAILED DESCRIPTION OF THE INVENTION

The abbreviations of amino acids, peptides, protecting groups or the like used in this specification are based on those established by IUPAC-IUB Commission on Biochemical Nomenclature or those commonly used in the relevant fields. When optical isomers of amino acids are present, they are L-isomers unless otherwise specified.

The term "microcapsule" used in this specification includes microspheres, microcapsules, microparticles, nanospheres and nanocapsules.

The term "s/o/w type emulsion" used in this specification means a solid/oil/water (solid phase in oil in water type). The "s" phase means a solid phase including microparticles and an aqueous phase in the form of gel.

The present invention has made it possible to prepare a sustained-release microcapsule which contains a high content of the water-soluble compound (I) with a relatively low initial release thereof.

The amorphous compound (I) employed in the present invention is soluble in water, which means that the solubility of the compound (I) in water is not less than about 1 g/100 ml at 20° C. Preferably, the compound (I) is a one which is readily soluble in water. The term "readily soluble in water" means that the water-solubility of the compound (I) is, in general, not less than about 5 g/100 ml at 20° C.

As described above, the compound (I) of this invention is (1) a compound, whose characteristic feature in the chemical structure lies in having proton-accepting groups respectively at terminals of substituents at 3- and 4-positions on the piperazine ring, represented by the formula (I):

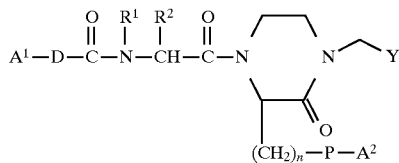

wherein $A^1$ and $A^2$ independently are a proton-accepting group or a group convertible into a proton-accepting group; D is a spacer having a 2- to 6-atom chain optionally bonded through a hetero-atom and/or a 5- or 6-membered ring (provided that the 5- or 6-membered ring is, depending on its bonding position, counted as 2- or 3-atom chain); $R^1$ is a hydrogen atom or a hydrocarbon group; $R^2$ is a hydrogen atom or a residual group formed by removing —CH(NH$_2$)COOH from an α-amino acid, or $R^1$ and $R^2$ may be combined to form a 5- or 6-membered ring; P is a spacer having a 1- to 10-atom chain optionally bonded through a hetero-atom and/or a 5- or 6-membered ring (provided that the 5- or 6-membered ring is, depending on its bonding position, counted as 2- or 3-atom chain); Y is an optionally esterified or amidated carboxyl group; and n denotes an integer of 0 to 8, or a salt thereof.

Especially, the following compounds are preferable, namely, (2) a compound as described in (1) above, wherein $A^1$ and $A^2$ independently are an optionally substituted amino, amidino or guanidino group or a group convertible to them, (3) a compound as described in (1) above, wherein $A^1$ and $A^2$ independently are an optionally substituted oxadiazolyl or thiadiazolyl group, (4) a compound as described in (1) above, wherein $A^1$ and $A^2$ independently are (1) an amidino or guanidino group which may be substituted with $C_{2-8}$ alkoxycarbonyl, or (2) an amino group which may be substituted with an oxadiazolyl group which may be substituted with oxo or $C_{1-4}$ alkyl which may be substituted with halogen, (5) a compound as described in (1) above, wherein $A^1$ and $A^2$ independently are an unsubstituted amino, amidino or guanidino group, (6) a compound as described in (1) above, wherein D is group of the formula:

(i) 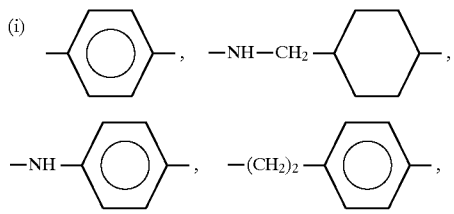

(7) a compound as described in (1) above, wherein $R^1$ is a hydrogen atom, (8) a compound as described in (1) above, wherein $R^2$ is a hydrogen atom or a $C_{1-4}$ alkyl group substituted with phenyl optionally substituted with $C_{1-4}$ alkoxy, (9) a compound as described in (1) above, wherein P is a group of the formula: in which Z is

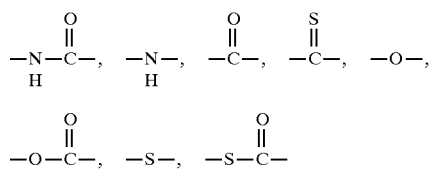

in which either bond may be bonded to B, or a bond; and B is

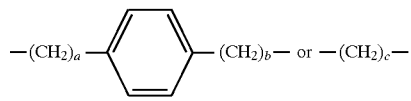

in which a is an integer of 0 to 2, b is an integer of 0 to 2 and c is an integer of 1 to 5, or (ii) a bond, excepting the case where Z and B both are a bond, (10) a compound as described in (9) above, wherein Z is

in which either bond may be bonded to B,

(11) a compound as described in (9) above, wherein B is

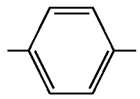

or —(CH$_2$)$_d$— in which d is an integer of 1 to 4,

(12) a compound as described in (1) above, wherein Y is a carboxyl group or a $C_{1-6}$ alkoxy-carbonyl group,

(13) a compound as described in (1) above, wherein n is an integer of 1 to 4,

(14) a compound as described in (1) above, wherein n is 2 or 3,

(15) a compound as described in (1) above, wherein $A^1$ and $A^2$ independently are 1) an amidino or guanidino group optionally substituted with $C_{2-8}$ alkoxycarbonyloxy, 2) an amino group optionally substituted with oxadiozolyl optionally substituted with oxo or $C_{1-4}$ alkyl optionally substituted with halogen, or 3) an oxadiazolyl group optionally substituted with oxo or $C_{1-4}$ alkyl optionally substituted with halogen, D is a group of the formula:

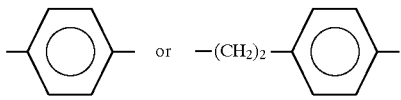

$R^1$ is a hydrogen atom, $R^2$ is a hydrogen atom or a $C_{1-4}$ alkyl group substituted with phenyl optionally substituted with $C_{1-4}$ alkoxy, P is a group of the formula: —Z—B— wherein Z is

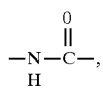

a bond or

and B is

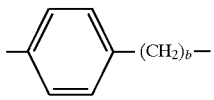

or —$(CH_2)_c$— in which b is 0 or 1, and c is an integer of 1 to 5,

Y is a group of the formula:

wherein $R^7$ is 1) hydroxy group, 2) a $C_{1-8}$ alkoxy or $C_{2-12}$ alkenyloxy group which may be substituted with $C_{1-4}$ alkoxy-carbonyl or 5-methyl-2-oxo-1,3-dioxolen-4-yl, or 3) a group of the formula: —$OCH(R^{7a})OCOR^8$ in which $R^{7a}$ is a hydrogen atom or a $C_{1-6}$ alkyl group, and $R^8$ is a $C_{1-6}$ alkyl group or a $C_{5-7}$ cycloalkyloxy group, and n is an integer of 1 to 4,

(16) a compound as described in (1) above, wherein $A^1$ and $A^2$ are independently 1) an amidino or guanidino group optionally substituted with methoxycarbonyl or 2) an amino group optionally substituted with 5-oxo-1,2,4-oxodiazol-3-yl or 5-trifluoromethyl-1,2,4-oxadiazol-3-yl,

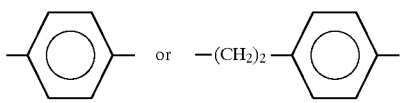

$R^1$ is a hydrogen atom, $R^2$ is a hydrogen atom or p-methoxybenzyl,

P is

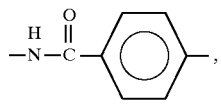

Y is a carboxyl group and n is 2 or 3, and

(17) a compound as described in (1) above, wherein $A^1$ and $A^2$ are independently an unsubstituted amino, amidino or guanidino group and $R^2$ is a hydrogen atom.

In the above formula (I), $A^1$ and $A^2$ independently are a proton-accepting group or a group convertible into a proton-accepting group.

In the above formula (I), the proton-accepting group means a group which accepts proton from a relevant group, namely a Bronsted base as exemplified by a group containing nitrogen atom capable of being positively charged. Specific examples of the proton-accepting group include optionally substituted amino, amidino and guanidino groups. Preferable examples of the proton-accepting group include unsubstituted amino, amidino and guanidino groups, or secondary or tertiary amino groups (especially ethylamino), amidino or guanidino groups substituted with a $C_{1-4}$ alkyl group.

Examples of the substituents of optionally substituted amino, amidino and guanidino groups include chain-like or cyclic hydrocarbon groups such as $C_{1-6}$ alkyl groups (e.g. methyl, ethyl, propyl, isopropyl, butyl, sec-butyl, tert-butyl, pentyl and hexyl), $C_{2-6}$ alkenyl groups (e.g. vinyl, allyl, isopropenyl, butenyl, isobutenyl and sec-butenyl), $C_{2-6}$ alkynyl groups (e.g. propargyl, ethynyl, butynyl and 1-hexynyl), $C_{3-6}$ cycloalkyl groups (e.g. cyclopropyl, cyclobutyl, cyclopentyl and cyclohexyl), $C_{6-14}$ aryl groups (e.g. phenyl, tolyl, xylyl, 1-naphthyl, 2-naphthyl, biphenyl, 2-indenyl and 2-anthryl, especially phenyl group), and $C_{7-16}$ aralkyl groups (e.g. benzyl, phenethyl, diphenylmethyl, triphenylmethyl, 1-naphthylmethyl, 2-naphthylmethyl, 2-diphenylethyl, 3-phenylpropyl, 4-phenylbutyl and 5-phenylpentyl, especially benzyl group); $C_{1-4}$ alkyl groups (e.g. methyl) substituted with carbamoyloxy optionally substituted with $C_{1-4}$ alkyl (e.g. N,N-dimethylaminocarbonyloxy), $C_{2-5}$ alkanoyloxy (e.g. pivaloyloxy) or a 5- or 6-membered heterocyclic group (e.g. a 5-membered cyclic group containing, besides carbon atoms, 1 to 4 hetero-atoms selected from oxygen atom, sulfur atom and nitrogen atom, such as 2- or 3-thienyl, 2- or 3-furyl, 1-, 2- or 3-pyrrolyl, 1-, 2- or 3-pyrrolidinyl, 2-, 4- or 5-oxazolyl, 2-, 4- or 5-thiazolyl, 3-, 4- or 5-pyrazolyl, 2-, 4- or 5-imidazolyl, 1,2,3-triazolyl, 1,2,4-triazolyl and 1H- or 2H-tetrazolyl, a 6-membered cyclic group, preferably pyrrolidin-1-yl and morpholino, containing, besides carbon atoms, 1 to 4 hetero-atoms selected from oxygen atom, sulfur atom and nitrogen atom, such as 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, piperidinyl, pyranyl, thiopyranyl, 1,4-oxazinyl, 1,4-thiadinyl, 1,3-thiadinyl, piperazinyl, triazinyl, 3- or 4-pyridazinyl, pyrazinyl, N-oxido-3- or 4-pyridazinyl); $C_{2-8}$ alkoxycarbonyl (e.g. methoxycarbonyl, ethoxycarbonyl, propoxycarbonyl, butoxycarbonyl, pentyloxycarbonyl, n-hexyloxycarbonyl and n-octyloxycarbonyl); $C_{1-8}$ alkylaminocarbonyl (e.g. n-hexylaminocarbonyl and n-octylaminocarbonyl); $C_{2-8}$ alkoxycarbonyloxy (e.g. methoxycarbonyloxy, ethoxycarbonyloxy, propoxycarbonyloxy, butoxycarbonyloxy, pentyloxycarbonyloxy, n-hexyloxycarbonyloxy and n-octyloxycarbonyloxy, preferably methoxycarbonyloxy); and 5- or 6-membered heterocyclic groups (e.g. a 5-membered cyclic group containing, besides carbon atoms, 1 to 4 hetero-atoms selected from oxygen atom, sulfur atom and nitrogen atom, such as 2- or 3-thienyl, 2- or 3-furyl, 1-, 2- or 3-pyrrolyl, 1-, 2- or 3-pyrrolidinyl, 2-, 4- or 5-oxazolyl, 2-, 4- or 5-thiazolyl, 3-, 4- or 5-pyrazolyl, 2-, 4- or 5-imidazolyl, 1,2,3-triazolyl, 1,2,4-triazolyl and 1H- or 2H-tetrazolyl, a 6-membered cyclic group, preferably e.g. tetrahydrofuran-2-yl, containing, besides carbon atoms, 1 to 4 hetero-atoms selected from oxygen atom, sulfur atom and nitrogen atom, such as 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, piperidinyl, pyranyl, thiopyranyl, 1,4-oxazinyl, 1,4-thiadinyl, 1,3-thiadinyl, piperazinyl, triazinyl, 3- or 4-pyridazinyl, pyrazinyl, N-oxido-3- or 4-pyridazinyl). And, in the case where two or more substituents of the amino, amidino or guanidino group exist, they may be combined to form a 5- or 6-membered heterocyclic group (e.g. pyrrolidine, piperidine, morpholine or imidazoline).

Preferable groups convertible into proton-accepting groups include groups which convert into proton-accepting groups in a living body and can accept physiologically active free proton. Examples of these groups include amidoxime groups optionally having substituents on oxygen atom (specific examples of the substituents include lower ($C_{1-4}$) alkyl (e.g. methyl, ethyl, propyl), acyl (e.g. $C_{2-5}$ alkanoyl (e.g. pivaloyl) and benzoyl), lower ($C_{1-4}$) alkoxy-carbonyl (e.g. methoxycarbonyl, ethoxycarbonyl, propoxycarbonyl), lower ($C_{1-4}$) alkylthiocarbonyl (e.g. methylthiocarbonyl, ethylthiocarbonyl), acyloxycarbonyl (e.g. $C_{2-5}$ alkanoyloxycarbonyl (e.g. pivaloyloxycarbonyl) and benzoyloxycarbonyl), optionally substituted $C_{6-12}$ aryloxycarbonyl (e.g. phenoxycarbonyl) or $C_{7-14}$ aralkyloxycarbonyl (e.g. benzyloxycarbonyl) (specific examples of the substituents include cyano, nitro, amino, lower ($C_{1-4}$) alkoxycarbonyl (e.g. methoxycarbonyl, ethoxycarbonyl, propoxycarbonyl), lower ($C_{1-4}$) alkyl (e.g. methyl, ethyl, propyl), lower ($C_{1-4}$) alkoxy (e.g. methoxy, ethoxy, propoxy), mono- and di- lower ($C_{1-4}$) alkylamino (e.g. methylamino, ethylamino, propylamino, dimethylamino), hydroxy, amido and lower ($C_{1-4}$) alkylthio (e.g. methylthio, ethylthio), optionally substituted $C_{6-12}$ aryl-carbonyl groups (e.g. phenylcarbonyl) (specific examples of the substituents include lower ($C_{1-4}$) alkyl (e.g. methyl, ethyl, propyl), lower ($C_{1-4}$) alkenyl (e.g. vinyl, allyl) or lower ($C_{1-4}$) alkynyl (e.g. ethynyl), or optionally substituted carbamoyl groups (specific examples of the substituents include cyano, nitro, amino, lower ($C_{1-4}$) alkoxy carbonyl (e.g. methoxycarbonyl, ethoxycarbonyl, propoxycarbonyl), lower ($C_{1-4}$) alkyl (e.g. methyl, ethyl, propyl), lower ($C_{1-4}$) alkoxy (e.g. methoxy, ethoxy, propoxy), mono- and di- lower ($C_{1-4}$) alkylamino (e.g. methylamino, ethylamino, propylamino, dimethylamino), hydroxy, amido and lower ($C_{1-4}$) alkylthio (e.g. methylthio, ethylthio), and optionally substituted oxadiazolyl or thiadiazolyl groups (examples of the substituents include oxo, thioxo, hydroxy, amino, mono- and di- lower ($C_{1-4}$) alkylamino (e.g. methylamino, ethylamino, propylamino, dimethylamino), halogen (e.g. fluoro, bromo, chloro), cyano, azido, lower ($C_{1-4}$) alkyl optionally substituted with halogen (e.g. trifluoromethyl), lower ($C_{1-4}$) alkoxy (e.g. methoxy, ethoxy, propoxy), lower ($C_{1-4}$) alkylthio (e.g. methylthio, ethylthio), lower ($C_{1-4}$) alkoxy carbonyl (e.g. methoxycarbonyl, ethoxycarbonyl, propoxycarbonyl), mono- or di- lower ($C_{1-4}$) alkylamino (e.g. methylamino, ethylamino, propylamino, dimethylamino), lower ($C_{1-4}$) alkylcarbamoyl (e.g. methylcarbamoyl, ethylcarbamoyl), $C_{6-12}$ aryl (e.g. phenyl) groups optionally having a substituent (specific examples the substituents include cyano, nitro, amino, lower ($C_{1-4}$) alkoxy carbonyl (e.g. methoxycarbonyl, ethoxycarbonyl, propoxycarbonyl), lower ($C_{1-4}$) alkyl (e.g. methyl, ethyl, propyl), lower ($C_{1-4}$) alkoxy (e.g. methoxy, ethoxy, propoxy), mono- and di- lower ($C_{1-4}$) alkylamino (e.g. methylamino, ethylamino, propylamino, dimethylamino), hydroxy, amido and lower ($C_{1-4}$) alkylthio (e.g. methylthio, ethylthio), or $C_{7-14}$ aralkyl groups (e.g. benzyl) optionally having a substituent (specific examples of the substituents include cyano, nitro, amino, lower ($C_{1-4}$) alkoxy carbonyl (e.g. methoxycarbonyl, ethoxycarbonyl, propoxycarbonyl), lower ($C_{1-4}$) alkyl (e.g. methyl, ethyl, propyl), lower ($C_{1-4}$) alkoxy (e.g. methoxy, ethoxy, propoxy), mono- and di- lower ($C_{1-4}$) alkylamino (e.g. methylamino, ethylamino, propylamino, dimethylamino), hydroxy, amido or lower ($C_{1-4}$) alkylthio (e.g. methylthio, ethylthio)), and among the optionally substituted oxadiazolyl or thiazolyl groups, 1,2,4-oxadiazol-3-yl or 1,2,4-thiadiazol-3-yl groups optionally having a substituent respectively are preferable. And, in the case where the substituent is oxo or thioxo, the groups may take either keto- or enol-form.

Among the optionally substituted $C_{6-12}$ aryloxycarbonyl or $C_{7-14}$ aralkyloxycarbonyl groups, optionally substituted carbamoyl groups, optionally substituted $C_{6-12}$ aryl groups or optionally substituted $C_{7-14}$ aralkyl groups as the above substituent of the amidoxime, oxadiazolyl and thiadiazolyl group, are preferable those respectively substituted with cyano, nitro, lower ($C_{1-4}$) alkoxy-carbonyl or lower ($C_{1-4}$) alkoxy.

Among the optionally substituted $C_{6-12}$ aryl-carbonyl groups as the above substituent of the amidoxime group, are preferable those substituted with hydrogen atom or lower ($C_{1-4}$) alkyl.

More specific examples of the groups convertible into proton-accepting groups include 5-oxo-1,2,4-oxadiazol-3-yl group, 5-oxo-1,2,4-thiadiazol-3-yl group, 5-thioxo-1,2,4-oxadiazol-3-yl group, 5-thioxo-1,2,4-thiadiazol-3-yl group, 4-methyl-5-oxo-1,2,4-oxadiazol-3-yl group, 4-ethyl-5-oxo-1,2,4-oxadiazol-3-yl group, 4-propyl-5-oxo-1,2,4-oxadiazol-3-yl group, 1,2,4-oxadiazol-3-yl group, 5-ethoxycarbonyl-1,2,4-oxadiazol-3-yl group, 5-carbamoyl-1,2,4-oxadiazol-3-yl group, 5-cyano-1,2,4-oxadiazol-3-yl group, 5-trifluoromethyl-1,2,4-oxadiazol-3-yl group, 5-phenyl-1,2,4-oxadiazol-3-yl group, 5-amino-1,2,4-oxadiazol-3-yl group, 5-propylamino-1,2,4-oxadiazol-3-yl group, 5-methylthio-1,2,4-oxadiazol-3-yl group, 5-azido-1,2,4-oxadiazol-3-yl group, amino (hydroxy) imino group, amino (methoxycarbonyloxy) imino group, amino (ethoxycarbonyloxy) imino group, amino (n-propyloxycarbonyloxy) imino group, amino (benzyloxycarbonyloxy) imino group, amino (p-nitrobenzyloxycarbonyloxy) imino group, amino (p-nitrophenyloxycarbonyloxy) imino group, amino (p-nitrobenzoyloxycarbonyloxy) imino group, amino (methoxy) imino group, amino (carbamoyloxy) imino group, amino (methylcarbamoyloxy) imino group, amino (ethylcarbamoyloxy) imino group, amino (n-propylcarbamoyloxy) imino group and amino (n-butylcarbamoyloxy) imino group.

Among them, are preferable 5-oxo-1,2,4-oxadiazol-3-yl group, 5-oxo-1,2,4-thiadiazol-3-yl group, 5-ethoxycarbonyl-1,2,4-oxadiazol-3-yl group, 5-cyano-1,2,4-oxadiazol-3-yl group, 5-trifluoromethyl-1,2,4-oxadiazol- 3-yl group, amino (methoxycarbonyloxy) imino group, amino (carbonyloxy) imino group, amino (methylcarbamoyloxy) imino group and amino (ethylcarbamoyloxy) imino group.

Preferable example of $A^1$ and $A^2$ include (1) amidino and guanidino groups which may be substituted with $C_{2-8}$ alkoxycarbonyloxy, and (2) amino groups which may be substituted with oxadiazolyl group which may be substituted with oxo or $C_{1-4}$ alkyl which may be substituted with halogen, and are unsubstituted amino, amidino or guanidino groups are more preferable.

And, the compound (I), wherein $A^1$ or $A^2$ are a group convertible into a proton-accepting group, or a salt thereof can be advantageously used as an orally administrable preparation.

In the above formula (I), D is a spacer having a 2- to 6-atom chain optionally bonded through a hetero-atom and/or a 5- or 6-membered ring (provided that the 5- or 6-membered ring is, depending on its bonding position, counted as 2- or 3-atom chain).

The spacer of D means a linear interval between $A^1$

and means having a interval with 2 to 6 atoms between them in the present invention.

In the above formula (I), examples of hetero-atoms in the spacer having a 2- to 6-atom chain (2- to 6-membered chain) optionally bonded through a hetero-atom and/or a 5- or 6-membered ring include N, O and S. And, the 5- or 6-membered ring may be carbocyclic one or a heterocyclic one containing 1 to 4 hetero-atoms selected from N, O and S or a saturated ring or an unsaturated ring such as aromatic ring. Examples of such 5- or 6-membered ring include the following;

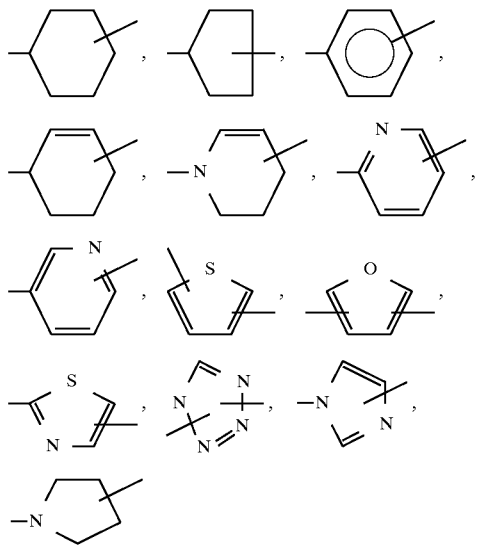

And, the above-mentioned 5- or 6-membered ring preferably has no bond at the adjacent position on the ring. The above-mentioned 5- or 6-membered ring preferably has a bond at the second or third position to one another on the ring. Usually, even though the ring is saturated or unsaturated, it is regarded as 2-to 3-atom chain (2- to 3-membered chain), and a group having a 2- to 6-atom chain as D itself is preferable. Nitrogen is the most preferable hetero-atom existing in the spacer shown by D, and, it is especially preferable to have D bonded to a group shown by $A^1$, such as an amidino group, through the -NH- group. The above-mentioned 5- or 6-membered ring may be bonded to the adjacent amidino group directly or to a group shown by $A^1$ such as amidino group through the —NH— group, and further to a group shown by $A^1$ such as amidino group through a methylene chain.

The adjacent carbonyl group may be bonded directly to the above-mentioned 5- or 6-membered ring, or bonded through a methylene chain or bonded through a hetero atom. The methylene chain in D may be substituted with a group of the formula

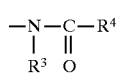

wherein $R^3$ is a hydrogen atom or a lower ($C_{1-4}$) alkyl group optionally substituted with an optionally substituted phenyl group; and $R^4$ is a lower ($C_{1-4}$) alkyl group optionally substituted with an optionally substituted phenyl group, an optionally substituted phenyl group or benzyloxy group.

Examples of substituents of the optionally substituted phenyl group as the substituent to the lower ($C_{1-4}$) alkyl group of $R^3$ or $R^4$ include lower ($C_{1-4}$) alkyl (e.g. methyl, ethyl), lower ($C_{1-4}$) alkoxy (e.g. methoxy, ethoxy), halogen (e.g. fluoro, chloro, bromo), and hydroxyl group.

Example of the lower ($C_{1-4}$) alkyl group of $R^3$ or $R^4$ include methyl and ethyl.

Preferable typical groups shown by D include those of the formula

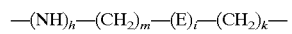

wherein h and i each is 0 or 1; m and k each is 0, 1 or 2; and E is the above-mentioned 5- or 6-membered ring, especially a cyclohexane ring, benzene ring, piperidine or a group of the formula

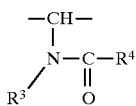

It is especially preferable when E is a 5- or 6-membered ring and, when h is 0 or 1, m is 0, 1 or 2, and k is 0. Among 5- or 6-membered rings shown by E, benzene ring and cyclohexane ring are preferable, and benzene ring is especially preferable.

In the above-mentioned formula (I), groups of the formula

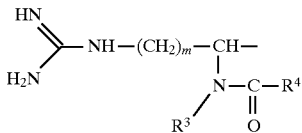

are substituted groups derived from arginine or homoarginine, wherein $R^3$, $R^4$ and m are the same as defined above, are especially preferable when D is a group of the formula

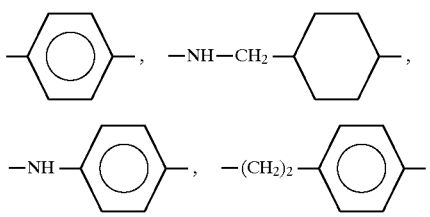

among others, above all

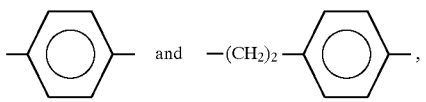

and especially

(in these groups, either of the bonds may be bonded to $A^1$).

In the above formula (I), $R^1$ is a hydrogen atom or a hydrocarbon group which may be chain-like or cyclic hydrocarbon groups including $C_{1-6}$ alkyl groups (e.g. methyl, ethyl, propyl, isopropyl, butyl, sec-butyl, tert-butyl, pentyl and hexyl), $C_{2-6}$ alkenyl groups (e.g. vinyl, allyl, isopropenyl, butenyl, isobutenyl and sec-butenyl), $C_{2-6}$ alkynyl groups (e.g. propargyl, ethynyl, butynyl and 1-hexynyl), $C_{3-6}$ cycloalkyl groups (e.g. cyclopropyl, cyclobutyl, cyclopentyl and cyclohexyl), $C_{6-14}$ aryl groups (e.g. phenyl, tolyl, xylyl, 1-naphthyl, 2-naphthyl, biphenyl, 2-indenyl and 2-anthryl, especially phenyl group), and $C_{7-16}$ aralkyl groups (e.g. benzyl, phenethyl, diphenylmethyl, triphenylmethyl, 1-naphthylmethyl, 2-naphthylmethyl, 2-diphenylethyl, 3-phenylpropyl, 4-phenylbutyl and 5-phenylpentyl, especially benzyl group). $R^1$ is preferably hydrogen, lower ($C_{1-4}$) alkyl or benzyl (especially hydrogen).

In the above formula (I), $R^2$ is a hydrogen atom or any of the residual groups formed by removing —CH(NH$_2$)COOH from an α-amino acid.

$R^1$ and $R^2$ may be combined to form a 5- or 6-membered ring. Preferable examples of such a 5- or 6-membered ring include rings as shown below,

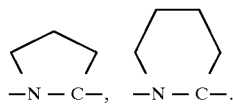

Usually, preferable examples of $R^2$ include residual groups of essential amino acids. Especially preferable examples of $R^2$ include a hydrogen atom, lower ($C_{1-4}$) alkyl groups, lower ($C_{1-4}$) alkyl groups substituted with an optionally substituted phenyl group, lower ($C_{1-4}$) alkyl groups substituted with hydroxyl group and lower ($C_{1-4}$) alkyl groups substituted with carbamoyl group. More specifically, R may be hydrogen, methyl, isopropyl, sec-butyl, isobutyl, hydroxylmethyl, benzyl, p-hydroxybenzyl, p-methoxybenzyl, carbamoylmethyl and carbamoylethyl.

Substituents optionally substituted on the benzene ring of an optionally substituted phenyl group as the substituent of the lower ($C_{1-4}$) alkyl of the above $R^2$, may be, for example, lower ($C_{1-4}$) alkyl groups (e.g. methyl, ethyl, propyl, isopropyl, n-butyl and sec-butyl), lower ($C_{1-4}$) alkoxy groups (e.g. methoxy and ethoxy), halogen (e.g. chlorine, fluorine and bromine) and hydroxyl group, and preferably, a lower ($C_{1-4}$) alkoxy group.

$R^2$ is preferably hydrogen or a $C_{1-4}$ alkyl group substituted with a phenyl group optionally substituted with $C_{1-4}$ alkoxy, more preferably p-hydroxybenzyl, p-methoxybenzyl or hydrogen atom, more preferably p-methoxybenzyl or hydrogen atoms and especially hydrogen.

In the above-mentioned formula (I), n is an integer of 0 to 8, preferably 1 to 4, and especially 2 or 3.

In the above formula (I), P is a spacer having a 1- to 10-atom chain optionally bonded through a hetero-atom and/or a 5- or 6-membered ring (provided that the 5- or 6-membered ring is, depending on its bonding position, counted as 2- or 3-atom chain). The spacer P is linear interval between (CH$_2$)$_n$ and $A^2$, and is 1 to 10 atoms optionally bonded through hetero-atoms and/or a 5- or 6-membered ring. P may be a divalent hydrocarbon group optionally bonded through 1 to 4 (preferably 1 or 2) groups selected from

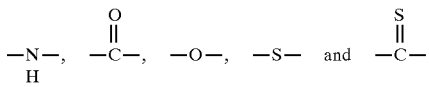

and/or a 5- or 6-membered ring. The 5- or 6-membered ring may be a saturated or unsaturated carbocyclic or heterocyclic ring containing 1 to 4 hetero-atoms selected from N, O and S. The carbocyclic ring, may be

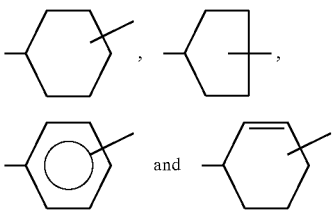

where the benzene ring and cyclohexane ring are preferable, and the benzene ring is especially preferable. The heterocyclic ring, may be a 5-membered cyclic group containing, besides carbon atoms, 1 to 4 hetero-atoms selected from, for example, an oxygen atom, sulfur atom and nitrogen atom, as exemplified by 2- or 3-thienyl, 2- or 3-furyl, 1-, 2- or 3-pyrrolyl, 1-, 2- or 3-pyrrolidinyl, 2-, 4- or 5-oxazolyl, 2-, 4- or 5-thiazolyl, 3-, 4- or 5-pyrazolyl, 2-, 4- or 5-imidazolyl, 1,2,3-triazolyl, 1,2,4-triazolyl, and 1H- or 2H-tetrazolyl. The heterocyclic ring may be a 6-membered cyclic group containing, besides carbon atoms, 1 to 4 hetero-atoms selected from an oxygen atom, sulfur atom and nitrogen atom, as exemplified by 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, piperidinyl, pyranyl, thiopyranyl, 1,4-oxazinyl, 1,4-thiazinyl, 1,3-thiazinyl, piperazinyl, triazinyl, 2- or 4-pyridazinyl, pyrazinyl, and N-oxido-3- or 4-pyridazinyl, where piperazine or piperidine is preferable.

More preferable spacer having a 1- to 10-atom chain optionally bonded through hetero-atoms and/or a 5- or 6-membered ring, is a divalent hydrocarbon group optionally bonded through 1 to 4 (preferably 1 or 2) groups selected from

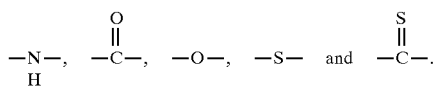

In the above-mentioned formula (I), P is represented by, for example, the formula,

—Z—B— wherein Z is a one selected from

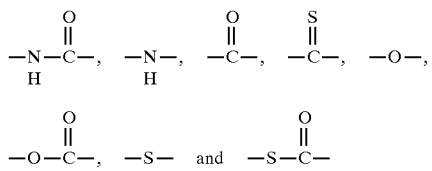

(either bond may be bonded to B) or a bond, and B is a group

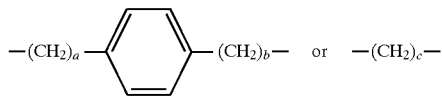

(a and b are an integer of 0 to 2 (preferably 0 or 1), and c is an integer of 1 to 5) or a bond (excepting the case where Z and B are both bonds).

Among the groups shown by the above Z, those represented by

(either of the bonds may be bonded to B) are preferable.

Among the groups shown by the above B, those represented by

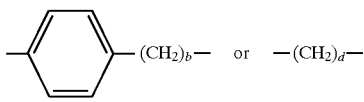

wherein b is an integer of 0 to 2 (preferably 0 or 1), and d is an integer of 1 to 4, are preferable. Further preferable groups shown by the above B include

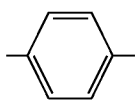

or —(CH$_2$)$_d$— wherein d is an integer or 1 to 4.

Preferable examples of the optionally amidated carboxyl group shown by Y include groups represented by the formula

wherein $R^5$ and $R^6$ independently are hydrogen, a lower (C$_{1-6}$) alkyl group (e.g. methyl, ethyl, propyl, butyl and hexyl), a C$_{2-8}$ alkenyl group (e.g. allyl, 2-butenyl and 3-pentenyl), a lower (C$_{1-4}$) alkyl group substituted with a 5- or 6-membered heterocyclic group (e.g. pyridylmethyl) wherein the 5-membered cyclic group contains, besides carbon atoms, 1 to 4 hetero-atoms selected from, for example, oxygen atom, sulfur atom and nitrogen atom, as exemplified by 2- or 3-thienyl, 2- or 3-furyl, 1-, 2- or 3-pyrrolyl, 1-, 2- or 3-pyrrolidinyl, 2-, 4- or 5-oxazolyl, 2-, 4- or 5-thiazolyl, 3-, 4- or 5-pyrazolyl, 2-, 4- or 5-imidazolyl, 1,2,3-triazolyl, 1,2,4-triazolyl, 1H- or 2H-tetrazolyl, and, a 6-membered cyclic group containing, besides carbon atoms, 1 to 4 hetero-atoms selected from oxygen atom, sulfur atom and nitrogen atom, as exemplified by 2-, 3- or 4-pyridyl, N-oxido-2-, 3- or 4-pyridyl, 2-, 4- or 5-pyrimidinyl, N-oxido-3-, 4- or 5-pyrimidinyl, thiomorpholinyl, morpholinyl, piperidinyl, pyranyl, thiopyranyl, 1,4-oxazinyl, 1,4-thiazinyl, 1,3-thiazinyl, piperazinyl, triazinyl, 2- or 4-pyridazinyl, pyrazinyl, and N-oxido-3- or 4-pyridazinyl, preferably pyridyl) or a C$_{6-12}$ aralkyl group (e.g. benzyl, phenethyl and phenyl propyl), wherein the aryl groups in the aralkyl group may be unsubstituted or optionally substituted with one or two substituents as exemplified by nitro, halogen (chlorine, fluorine and bromine), lower (C$_{1-4}$) alkyl groups (e.g. methyl and ethyl) and lower (C$_{1-4}$) alkoxy groups (e.g. methoxy, ethoxy and propoxy).

Preferable examples of optionally esterified carboxyl groups shown by Y include groups of the formula

wherein $R^7$ is 1) hydroxyl group, 2) an optionally substituted alkoxy, alkenyloxy or benzyloxy group (e.g. lower (C$_{1-8}$) alkoxy (e.g. methoxy, ethoxy, propoxy), lower (C$_{2-12}$) alkenyloxy (e.g. vinyloxy, allyloxy) or benzyloxy group which may be substituted with hydroxyl group, optionally substituted amino (e.g. amino, N-lower (C$_{1-4}$) alkylamino (e.g. methylamino), N,N-di-lower (C$_{1-4}$) alkylamino (e.g. dimethylamino), piperidino and morpholino), halogen (e.g. chloro, fluoro, bromo), lower (C$_{1-6}$) alkoxy (e.g. methoxy, ethoxy), lower (C$_{1-6}$) alkylthio (e.g. methylthio, ethylthio), lower (C$_{1-4}$) alkoxy-carbonyl (e.g. methoxycarbonyl, ethoxycarbonyl, propoxycarbonyl, isobutyloxycarbonyl), or optionally substituted dioxolenyl (e.g. 5-methyl-2-oxo-1,3-dioxolen-4-yl)) or 3) a group of the formula —OCH(R$^{7a}$)OCOR$^8$ in which R$^{7a}$ is hydrogen, a straight-chain or branched lower (C$_{1-6}$) alkyl group (e.g. methyl, ethyl, n-propyl, isopropyl, n-butyl, isobutyl, sec-butyl, t-butyl, n-pentyl, isopentyl and neopentyl), or a C$_{5-7}$ cycloalkyl group (e.g. cyclopentyl, cyclohexyl and cycloheptyl), and R$^8$ is i) a straight-chain or branched lower (C$_{1-6}$) alkyl group (e.g. methyl, ethyl, n-propyl, isopropyl, n-butyl, isobutyl, sec-butyl, t-butyl, n-pentyl, isopentyl and neopentyl), ii) a lower (C$_{2-8}$) alkenyl group (e.g. vinyl, propenyl, allyl and isopropenyl), iii) a C$_{5-7}$ cycloalkyl group (e.g. cyclopentyl, cyclohexyl and cyclobutyl), iv) a lower (C$_{1-3}$) alkyl group substituted with C$_{5-7}$ cycloalkyl (e.g. cyclopentyl, cyclohexyl and cycloheptyl) or optionally substituted C$_{6-12}$ aryl such as phenyl (e.g. benzyl, p-chlorobenzyl, phenethyl, cyclopentylmethyl and cyclohexylmethyl), v) a lower (C$_{2-3}$) alkenyl group substituted with C$_{5-7}$ cycloalkyl (e.g. cyclopentyl, cyclohexyl and cycloheptyl) or optionally substituted C$_{6-12}$ aryl such as phenyl (e.g. cinnamyl having alkenyl moiety such as vinyl, propenyl, allyl or isopropenyl), vi) an optionally substituted aryl groups such as optionally substituted phenyl group (e.g. phenyl, p-tolyl and naphthyl), vii) a straight-chain or branched lower (C$_{1-6}$) alkoxy group (e.g. methoxy, ethoxy, n-propoxy, isopropoxy, n-butoxy, isobutoxy, sec-butoxy, t-butoxy, n-pentyloxy, isopentyloxy and neopentyloxy), viii) a straight-chain or branched lower ($C_{1-6}$) alkenyloxy group (e.g. allyloxy and isobutenyloxy), ix) a $C_{5-7}$ cycloalkyloxy group (e.g. cyclopentyloxy, cyclohexyloxy and cycloheptyloxy), x) a lower ($C_{1-3}$) alkoxy group substituted with $C_{5-7}$ cycloalkyl groups (e.g. cyclopentyl, cyclohexyl and cycloheptyl) or optionally substituted $C_{6-12}$ aryl such as phenyl (e.g. benzyloxy, phenethyloxy, cyclopentylmethyloxy and cyclohexylmethyloxy, having alkoxy moiety such as methoxy, ethoxy, n-propoxy or isopropoxy), xi) a lower ($C_{2-3}$) alkenyloxy group substituted with $C_{5-7}$ cycloalkyl groups (e.g. cyclopentyl, cyclohexyl and cycloheptyl) or optionally substituted $C_{6-12}$ aryl such as phenyl (e.g. cinnamyloxy having alkenyloxy moiety such as vinyloxy, propenyloxy, allyloxy or isopropenyloxy), xii) an optionally substituted $C_{6-12}$ aryloxy group such as an optionally substituted phenoxy group (e.g. phenoxy, p-nitrophenoxy and naphthoxy).

In the above formula, when the substituent $R^8$ includes an optionally substituted $C_{6-12}$ aryl group, the $C_{6-12}$ aryl group is exemplified by phenyl and naphthyl (preferably phenyl), and, $C_{6-12}$ aryl group, is exemplified by nitro, halogen (e.g. chlorine, fluorine and bromine), lower ($C_{1-4}$) alkyl (e.g. methyl, ethyl, propyl) and lower ($C_{1-4}$) alkoxy (e.g. methoxy, ethoxy, propoxy), and, among them, unsubstituted phenyl is preferably used.

Preferable examples of Y are a carboxyl group and a lower ($C_{1-4}$) alkoxy-carbonyl group (e.g. carboxyl, ethoxycarbonyl), wherein a carboxyl group is more preferable.

The compounds of the formula (I) include the compound wherein $A^1$ and $A^2$ are (1) an amino, amidino or guanidino group which may be substituted with $C_{1-6}$ alkyl; $C_{2-6}$ alkenyl; $C_{2-6}$ alkynyl; $C_{3-6}$ cycloalkyl; $C_{6-14}$ aryl; $C_{7-16}$ aralkyl; $C_{1-4}$ alkyl substituted with carbamoyloxy optionally substituted with $C_{1-4}$ alkyl, $C_{2-5}$ alkanoyloxy or a 5-membered cyclic group containing, besides carbon atoms, 1 to 4 hetero-atoms selected from oxygen atom, sulfur atom and nitrogen atom, or a 6-membered cyclic group containing, besides carbon atoms, 1 to 4 hetero-atoms selected from oxygen atom, sulfur atom and nitrogen atom; $C_{2-8}$ alkoxycarbonyl; $C_{1-8}$ alkylaminocarbonyl; $C_{2-8}$ alkoxycarbonyloxy; a 5-membered cyclic group containing, besides carbon atoms, 1 to 4 hetero-atoms selected from oxygen atom, sulfur atom and nitrogen atom, or a 6-membered cyclic group, besides carbon atoms, 1 to 4 hetero-atoms selected from oxygen atom, sulfur atom and nitrogen atom, in the case where two or more substituents of the amino, amidino or guanidino group exist, they may be combined to form a 5- or 6-membered heterocyclic group, (2) an amidoxime group which may be substituted on the oxygen atom with $C_{1-4}$ alkyl; $C_{2-5}$ alkanoyl; benzoyl; $C_{1-4}$ alkoxycarbonyl; $C_{1-4}$ alkylthiocarbonyl; $C_{2-5}$ alkanoyloxycarbonyl; benzoyloxycarbonyl; $C_{6-12}$ aryloxycarbonyl or $C_{7-14}$ aralkyloxycarbonyl which may be substituted with cyano, nitro, amino, $C_{1-4}$ alkoxycarbonyl, $C_{1-4}$ alkyl, $C_{1-4}$ alkoxy, mono- or di- $C_{1-4}$ alkylamino, hydroxy, amido or $C_{1-4}$ alkylthio; $C_{6-12}$ aryl-carbonyl which may be substituted with $C_{1-4}$ alkyl, $C_{2-4}$ alkenyl or $C_{2-4}$ alkynyl; carbamoyl which may be substituted with cyano, nitro, amino, $C_{1-4}$ alkoxy-carbonyl, $C_{1-4}$ alkyl, $C_{1-4}$ alkoxy, mono- or di- $C_{1-4}$ alkylamino, hydroxy, amido or $C_{1-4}$ alkylthio or (3) an oxadiazolyl or thiadiazolyl group which may be substituted with oxo; thioxo; hydroxy; amino; mono- or di- $C_{1-4}$ alkylamino; halogen; cyano; azido; $C_{1-4}$ alkyl optionally substituted with halogen; $C_{1-4}$ alkoxy; $C_{1-4}$ alkylthio; $C_{1-4}$ alkoxy-carbonyl; $C_{1-4}$ alkylcarbamoyl; $C_{6-12}$ aryl optionally substituted with cyano, nitro, amino, $C_{1-4}$ alkoxy-carbonyl, $C_{1-4}$ alkyl, $C_{1-4}$ alkoxy, hydroxy, amido or $C_{1-4}$ alkylthio; or $C_{7-14}$ aralkyl optionally substituted with cyano, nitro, amino, $C_{1-4}$ alkoxy-carbonyl, $C_{1-4}$ alkyl, $C_{1-4}$ alkoxy, mono- or di- $C_{1-4}$ alkylamino, hydroxy, amido or $C_{1-4}$ alkylthio, D is a 2- to 6- membered chain optionally bonded through a hetero-atom and/or a 5- or 6- membered carbocyclic ring or a 5- or 6- membered heterocyclic ring containing 1 to 4 hetero-atoms selected from N, O and S, provided that the 5- or 6-membered carbocyclic ring or the 5- or 6-membered heterocyclic ring containing 1 to 4 heteroatoms selected from N, O and S is, depending on its bonding position, counted as 2- or 3- membered chain, $R^2$ is a hydrogen atom, a $C_{1-6}$ alkyl group, a $C_{2-6}$ alkenyl group, a $C_{2-6}$ alkynyl group, a $C_{3-6}$ cycloalkyl group, a $C_{6-14}$ aryl group or a $C_{7-16}$ aralkyl group, $R^2$ is a hydrogen atom; a $C_{1-4}$ alkyl group; a $C_{1-4}$ alkyl group substituted with phenyl which may be substituted with $C_{1-4}$ alkyl, $C_{1-4}$ alkoxy, halogen or hydroxy; a $C_{1-4}$ alkyl group substituted with hydroxy; or a $C_{1-4}$ alkyl group substituted with carbamoyl, or $R^1$ and $R^2$ may be combined to form:

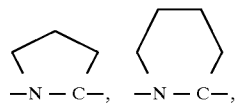

P is a 1- to 10-membered chain optionally bonded through a hetero atom and/or a 5- or 6-membered carbocyclic ring or a 5- or 6-membered heterocyclic ring containing 1 to 4 hetero-atoms selected from N, O and S, provided that the 5- or 6-membered carbocyclic ring or the 5- or 6-membered heterocyclic ring containing 1 to 4 hetero-atoms selected from N, O and S is, depending on its bonding position, counted as 2- or 3-membered chain, Y is a group of the formula:

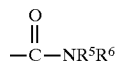

wherein $R^5$ and $R^6$ independently are hydrogen, a $C_{1-6}$ alkyl group; a $C_{2-8}$ alkenyl group; a $C_{1-4}$ alkyl group substituted with a 5-membered cyclic group containing, besides carbon atoms, 1 to 4 hetero-atoms selected from, oxygen atom, sulfur atom and nitrogen atom, or, a 6-membered cyclic group containing, besides carbon atoms, 1 to 4 hetero-atoms selected from oxygen atom, sulfur atom and nitrogen atom, or a $C_{6-12}$ aralkyl group which may be substituted with nitro, halogen, $C_{1-4}$ alkyl or $C_{1-4}$ alkoxy, or, a group of the formula:

wherein $R^7$ is 1) hydroxyl group, 2) a $C_{1-8}$ alkoxy, $C_{2-12}$ alkenyloxy or benzyloxy group which may substituted with hydroxyl, amino, N-$C_{1-4}$ alkylamino, N,N-di-$C_{1-4}$ alkylamino, piperidino, morpholino, halogen, $C_{1-6}$ alkoxy, $C_{1-6}$ alkylthio, $C_{1-4}$ alkoxy-carbonyl, or 5-methyl-2-oxo-1, 3-dioxolen-4-yl or 3) a group of the formula: —OCH($R^{7a}$) OCOR$^8$ in which $R^{7a}$ is hydrogen, a $C_{1-6}$ alkyl group or a $C_{5-7}$ cycloalkyl group, and $R^8$ is i) a $C_{1-6}$ alkyl group, ii) a $C_{2-8}$ alkenyl group, iii) a $C_{5-7}$ cycloalkyl, iv) a $C_{1-3}$ alkyl group substituted with $C_{5-7}$ cycloalkyl or $C_{6-12}$ aryl optionally substituted with nitro, halogen, $C_{1-4}$ alkyl or $C_{1-4}$ alkoxy, v) a $C_{2-3}$ alkenyl group substituted with $C_{5-7}$ cycloalkyl or $C_{6-12}$ aryl, vi) a $C_{6-12}$ aryl optionally substituted with nitro, halogen, $C_{1-4}$ alkyl or $C_{1-4}$ alkoxy, vii) a $C_{1-6}$ alkoxy group, viii) a $C_{2-6}$ alkenyloxy group, ix) a $C_{5-7}$ cycloalkyloxy group, x) a $C_{1-3}$ alkoxy group substituted with $C_{5-7}$ cycloalkyl or $C_{6-12}$ aryl optionally substituted with nitro, halogen, $C_{1-4}$ alkyl or $C_{1-4}$ alkoxy, xi) a $C_{2-3}$ alkenyloxy group substituted with $C_{5-7}$ cycloalkyl or $C_{6-12}$ aryl optionally substituted with nitro, halogen, $C_{1-4}$ alkyl or $C_{1-4}$ alkoxy, or xii) a $C_{6-12}$ aryloxy group optionally substituted with nitro, halogen, $C_{1-4}$ alkyl or $C_{1-4}$ alkoxy, and n is an integer of 0 to 8.

Among the compounds represented by the above-mentioned formula (I) or their salts, the compounds (Ia) of the formula

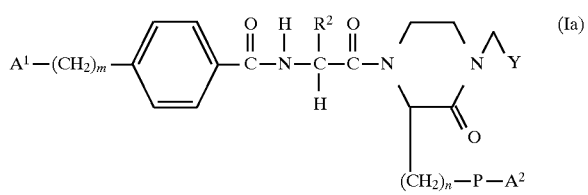

wherein $A^1$ and $A^2$ independently are an optionally substituted amino, amidino or guanidino group, an amidoxime group optionally having a substituent on the oxygen atom, or an optionally substituted oxadiazolyl or thiadiazolyl group, $R^2$ is hydrogen, a lower ($C_{1-4}$) alkyl group, a lower ($C_{1-4}$) alkyl group substituted with an optionally substituted phenyl group, a lower ($C_{1-4}$) alkyl group substituted with hydroxyl group or a lower ($C_{1-4}$) alkyl group substituted with carbamoyl group, P is a divalent hydrocarbon optionally bonded through 1 to 4 groups selected from

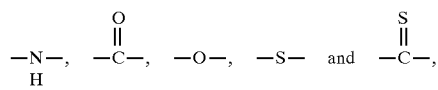

Y is an optionally esterified or amidated carboxyl group, m is an integer of 0 to 2, and n is an integer of 0 to 8, and their salts are preferable.

More preferable examples of the above-mentioned compounds (Ia) and their salts include compounds (Ia) wherein $A^1$ and $A^2$ independently are an unsubstituted amino, amidino or guanidino group, or an optionally substituted 1,2,4-oxadiazol-3-yl or 1,2,4-thiadiazol-3-yl group, $R^2$ is p-hydroxybenzyl, p-methoxybenzyl or hydrogen atom, P is a group of the formula, —Z—B— in which Z is a group selected from

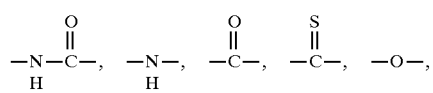

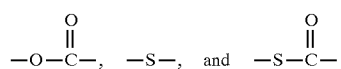

(either of the bonds of them may bonded to B) or a bond, and

B is

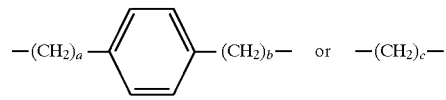

(a and b each is an integer of 0 to 2 (preferably 0 or 1), and c is an integer of 1 to 5) or a bond (excepting the case where Z and B both are a bond), Y is an optionally esterified or amidated carboxyl group, m is an integer of 0 to 2, and n is an integer of 1 to 4, and their salts.

Furthermore, preferable examples of the above-mentioned compounds (Ia) and their salts include compounds (Ia) wherein $A^1$ and $A^2$ independently are unsubstituted amino, amidino or guanidino group, or an optionally substituted 1,2,4-oxadiazol-3-yl or 1,2,4-thiadiazol-3-yl group, $R^2$ is p-hydroxybenzyl, p-methoxybenzyl or hydrogen atom, P is a group of the formula —Z—B— in which Z is

B is a group of the formula

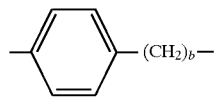

(b is an integer of 0 to 2 (preferably 0 or 1)), Y is an optionally esterified or amidated carboxyl group, m is an integer of 0 to 2, and n is an integer of 1 to 4, or their salts.

Preferable examples of the compound (I) and their salts include compounds (I) wherein $A^1$ and $A^2$ independently are (1) an amidino or guanidino group optionally substituted with $C_{2-8}$ alkoxycarbonyloxy, (2) an amino group optionally substituted with oxadiazolyl optionally substituted with oxo or $C_{1-4}$ alkyl optionally substituted with halogen, or (3) an oxadiazolyl group optionally substituted with oxo or $C_{1-4}$ alkyl optionally substituted with halogen, D is a group of the formula:

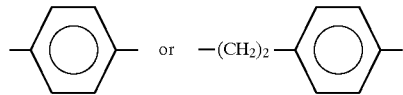

$R^1$ is a hydrogen atom, $R^2$ is a hydrogen atom or a $C_{1-4}$ alkyl group substituted with phenyl optionally substituted with $C_{1-4}$ alkoxy, P is a group of the formula: —Z—B— wherein Z is $$-\underset{H}{N}-\overset{O}{\underset{\|}{C}}-,$$

a bond or $$-\underset{H}{N}-,$$

and
B is

[benzene ring]—(CH$_2$)$_b$— or —(CH$_2$)$_c$— in which b is 0 or 1, and c is an integer of 1 to 5,
Y is a group of the formula:

$$-\overset{O}{\underset{\|}{C}}-R^7$$

wherein $R^7$ is 1) hydroxy group, 2) a $C_{1-8}$ alkoxy or $C_{2-12}$ alkenyloxy group which may be substituted with $C_{1-4}$ alkoxy-carbonyl or 5-methyl-2-oxo-1,3-dioxolen-4-yl, or
3) a group of the formula: —OCH($R^{7a}$)OCOR$^8$ in which $R^{7a}$ is a hydrogen atom or a $C_{1-6}$ alkyl group, and $R^8$ is a $C_{1-6}$ alkyl group or a $C_{5-7}$ cycloalkyloxy group, and n is an integer of 1 to 4.

More preferable examples of the compound (I) and their salts include compounds (I) wherein $A^1$ and $A^2$ are independently (1) an amidino or guanidino group optionally substituted with methoxycarbonyloxy or
(2) an amino group optionally substituted with 5-oxo-1,2,4-oxodiazol-3-yl or 5-trifluoromethyl-1,2,4-oxadiazol-3-yl, D is

[benzene ring]— or —(CH$_2$)$_2$—[benzene ring]—

$R^1$ is a hydrogen atom,
$R^2$ is a hydrogen atom or p-methoxybenzyl,
P is $$-\underset{H}{N}-\overset{O}{\underset{\|}{C}}-[\text{benzene ring}]-,$$

Y is a carboxyl group and
n is 2 or 3.

In the case where the compound of this invention is used as an orally administrable agent, desirable examples of optionally esterified carboxyl groups shown by Y include methoxycarbonyl, ethoxycarbonyl, tert-butoxycarbonyl, propoxycarbonyl, pivaloyloxymethoxycarbonyl, 1-(cyclohexylcarbonyloxy)ethoxycarbonyl, 5-methyl-2-oxo-1,3-dioxolen-4-ylmethoxycarbonyl, acetoxymethyloxycarbonyl, propionyloxymethoxycarbonyl, n-butyloxymethoxycarbonyl, isobutyloxymethoxycarbonyl, 1-(ethoxycarbonyloxy)ethoxycarbonyl, 1-(acetyloxy) ethoxycarbonyl, 1-(isobutyloxy)ethoxycarbonyl, 2-(isobutyloxycarbonyl)-2-propylidenethoxycarbonyl and (3-phthalidylidene)ethoxycarbonyl.

The compounds of this invention have one or more asymmetric carbons in the molecule, and both R-configurated compounds and S-configurated compounds relative to these asymmetric carbons are included in the present invention.

Examples of the salts of the compounds (I) and (Ia) to be used in this invention include pharmaceutically acceptable salt such as inorganic acid salts such as hydrochloride, hydrobromide, sulfate, nitrate and phosphate, organic acid salts such as acetate, tartrate, citrate, fumarate, maleate, toluenesulfonate and methanesulfonate, metal salts such as sodium salt, potassium salt, calcium salt and aluminum salt, and salts with a base such as triethylamine salt, guanidine salt, ammonium salt, hydrazine salt, quinine salt and cinchonine salt.

The compounds (I) and (Ia) and their salts may be hydrates or not hydrates.

Specific examples of preferable compounds include 4-(4-amidinobenzoyl)aminoacetyl-3-[3-(4-amidinobenzoyl) aminopropyl]-2-oxopyperazine-1-acetic acid, 4-(4-amidinobenzoyl)aminoacetyl-3-[4-(4-amidinobenzoyl) aminobutyl]-2-oxopiperazine-1-acetic acid, 4-(4-amidinobenzoyl)aminoacetyl-3-[2-(4-amidinobenzoyl) aminoethyl]-2-oxopiperazine-1-acetic acid, 4-(4-amidinobenzoyl)aminoacetyl-3-[2-(4-amidinophenylaminocarbonyl)ethly]-2-oxopiperazine-1-acetic acid, 4-(4-amidinobenzoyl)aminoacetyl-3-[3-(4-amidinophenylaminocarbonyl)propyl]-2-oxopiperazine-1-acetic acid, 4-(4-amidinobenzoyl)aminoacetyl-3-[4-(4-amidinophenylaminocarbonyl)butyl]-2-oxopiperazine-1-acetic acid, 4-(4-guanidinobenzoyl)aminoacetyl-3-[2-(4-guanidinobenzoylamino)ethyl]-2-oxopiperazine-1-acetic acid, 4-(4-guanidinobenzoyl)aminoacetyl-3-[3-(4-guanidinobenzoylamino)propyl]-2-oxopiperazine-1-acetic acid, 4-(4-guanidinobenzoyl)aminoacetyl-3-[4-(4-guanidinobenzoylamino)butyl]-2-oxopiperazine-1-acetic acid, 4-(4-amidinobenzoylamino)acetyl-3-[2-(4-guanidinobenzoylamino)ethyl]-2-oxopiperazine-1-acetic acid, 4-(4-amidinobenzoylamino)acetyl-3-[3-(4-guanidinobenzoylamino)propyl]-2-oxopiperazine-1-acetic acid, 4-(4-amidinobenzoylamino)acetyl-3-[4-(4-guanidinobenzoylamino)butyl]-2-oxopiperazine-1-acetic acid, 4-[4-(2-aminoethyl)benzoylamino]acetyl-3-[2-(4-amidinobenzoylamino)ethyl]-2-oxopiperazine-1-acetic acid, 4-[4-(2-aminoethyl)benzoylamino]-3-[3-(4-amidinobenzoylamino)propyl]-2-oxopiperazine-1-acetic acid, and 4-[4-(2-aminoethyl)benzoylamino]acetyl-3-[4-(4-amidinobenzoylamino)butyl]-2-oxopiperazine-1-acetic acid, 4-(4-amidinobenzoylamino)acetyl-3-[3-(4-guanidinobutanoylamino)]propyl-2-oxopiperazine-1-acetic acid, (S,S)-[3-[3-(4-guanidinobenzoylamino)propyl]-4-[3-(4-methoxyphenyl)-2-[4-(5-trifluoromethyl-[1,2,4] oxadiazol-3-ylamino)benzoylamino]propionyl]-2-oxopiperazine-1-yl]acetic acid, (S,S)-[4-[3-(4-methoxyphenyl)-2-[4-(5-trifluoromethyl[1,2,4]oxadiazol-3-ylamino)benzoylamino]propionyl]-2-oxo-3-[4-(5-trifluoromethyl[1,2,4]oxadiazol-3-ylaminobenzoyl-amino] propyl]piperazin-1-yl]acetic acid, (S,S)-[4-[3-(4-methoxyphenyl)-2-[4-(5-oxo-4,5-dihydro[1,2,4]oxadiazol-3-ylamino)benzoylamino]propionyl]-2-oxo-3-[4-(5-oxo-4, 5-dihydro[1,2,4]oxadiazol-3-ylamino)benzoylamino]-propyl]piperazin-1-yl]acetic acid or (S,S)-4-[2-(4-guanidinobenzoyl)amino-3-(4-methoxyphenyl)propionyl]-3-[3-(4-guanidinobenzoyl)aminopropyl]-2-oxopiperazine-1-acetic acid, or a salt thereof, more preferably, (S)-4-(4-amidinobenzoyl)aminoacetyl-3-{3-(4-amidinobenzoyl)amino}propyl-2-oxopiperazine-1-acetic acid [trifluoroacetate of this compound may be hereinafter referred to as Compound B], (S)-4-(4-guanidinobenzoylamino)acetyl-3-[3-(4-guanidinobenzoylamino)]propyl-2-oxopiperazine-1-acetic acid[hydrochloride of this compound may be hereinafter referred to as Compound A], (S)-4-(4-amidinobenzoylamino)acetyl-3-[2-(4-guanidinobenzoylamino)]ethyl-2-oxopiperazine-1-acetic acid[hydrochloride of this compound may be hereinafter referred to as Compound D], (S)-4-[4-(2-aminoethyl)benzoylamino]acetyl-3-[3-(4-amidinobenzoylamino)]propyl-2-oxopiperazine-1-acetic acid[trifluoroacetate of this compound may be hereinafter referred to as Compound C], (S)-4-(4-amidinobenzoylamino)acetyl-3-[3-(4-guanidinobutanoylamino)]propyl-2-oxopiperazine-1-acetic acid [hydrochloride of this compound may be hereinafter referred to as Compound E], (S,S)-[3-[3-(4-guanidinobenzoylamino)propyl]-4-[3-(4-methoxyphenyl)-2-[4-(5-trifluoromethyl-[1,2,4]oxadiazol-3-ylamino)benzoylamino]propionyl]-2-oxopiperazine-1-yl]acetic acid, (S,S)-[4-[3-(4-methoxyphenyl)-2-[4-(5-trifluoromethyl[1,2,4]oxadiazol-3-ylamino)benzoylamino]propionyl]-2-oxo-3-[3-[4-(5-trifluoromethyl[1,2,4]oxadiazol-3-ylaminobenzoyl-amino]propyl]piperazin-1-yl]acetic acid, (S,S)-[4-[3-(4-methoxyphenyl)-2-[4-(5-oxo-4,5-dihydro[1,2,4]oxadiazol-3-ylamino)benzoylamino]propionyl]-2-oxo-3-[4-(5-oxo-4,5-dihydro[1,2,4]oxadiazol-3-ylamino)benzoylamino]-propyl]piperazin-1-yl]acetic acid or (S,S)-4-[2-(4-guanidinobenzoyl)amino-3-(4-methoxyphenyl)propionyl]-3-[3-(4-guanidinobenzoyl)aminopropyl]-2-oxopiperazine-1-acetic acid, or a salt thereof, further more preferably, (S)-4-(4-amidinobenzoyl)aminoacetyl-3-{3-(4-amidinobenzoyl)amino}propyl-2-oxopiperazine-1-acetic acid, (S)-4-(4-guanidinobenzoylamino)acetyl-3-[3-(4-guanidinobenzoylamino)]propyl-2-oxopiperazine-1-acetic acid, (S)-4-(4-amidinobenzoylamino)acetyl-3-[2-(4-guanidinobenzoylamino)]ethyl-2-oxopiperazine-1-acetic acid or (S)-4-[4-(2-aminoethyl)benzoylamino]acetyl-3-[3-(4-amidinobenzoylamino)]propyl-2-oxopiperazine-1-acetic acid trifluoroacetate, or a salt thereof.

The most preferable example is (S)-4-(4-guanidinobenzoylamino)acetyl-3-[3-(4-guanidinobenzoylamino)propyl-2-oxopiperazine-1-acetic acid or a salt thereof (a pharmaceutically acceptable salt thereof), more preferably (S)-4-(4-guanidinobenzoylamino)acetyl-3-[3-(4-guanidinobenzoylamino)]propyl-2-oxopiperazine-1-acetic acid or a pharmaceutically acceptable acid addition salt thereof, especially preferably (S)-4-(4-guanidinobenzoylamino)acetyl-3-[3-(4-guanidinobenzoylamino)]propyl-2-oxopiperazine-1-acetic acid hydrochloride.

Another preferable example is 4-(4-guanidinobenzoylamino)acetyl-3-[3-(4-guanidinobenzoylamino)]propyl-2-oxopiperazine-1-acetic acid or a salt thereof.

The compounds (I) and (Ia) of this invention can be produced by, for example, methods as described below, namely, by reacting a compound (II) of the formula

wherein each symbol is of the same meaning as defined above or, a reactive derivative thereof, or a salt thereof, with a compound (III) of the formula

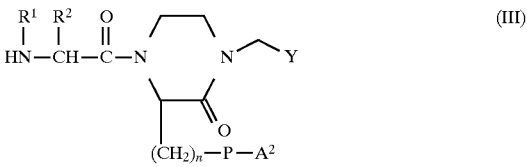

wherein each symbol is of the same meaning as defined above, or a salt thereof.

Examples of the salt of the compound (II) or (III) include inorganic acid salts such as hydrochloride, hydrobromide, sulfate, nitrate and phosphate, organic acid salts such as acetate, tartrate, citrate, fumarate, maleate, toluenesulfonate and methanesulfonate, metal salts such as sodium salt, potassium salt, calcium salt and aluminum salt, and salts with a base such as triethylamine salt, guanidine salt, ammonium salt, hydrazine salt, quinine salt and cinchonine salt, which are pharmaceutically acceptable ones.

Examples of the reactive derivative of the compound (II) include compounds (II) of the formula

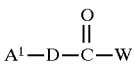

wherein $A^1$ is of the same meaning as defined above, and W is halogen (preferably chlorine) or corresponding acid halides, azides, active esters (esters with alcohol such as pentachlorophenol, 2,4,5-trichlorophenol, 2,4-dinitrophenol, cyanomethylalcohol, paranitrophenol, N-hydroxy-5-norbornene-2,3-dicarboxyimide, N-hydroxysuccinimide, N-hydroxyphthalimide, and N-hydroxybenztriazole).

The condensation reaction as the methods for producing the compounds (I) and (Ia) of this invention can be carried out by an amide-linkage formation reaction in a conventional peptide synthesis, for example, the method using active ester, mixed acid anhydride or acid chloride.

For example, the condensation reaction between the compound (II) and the compound (III) can be conducted by subjecting the compound (II) to condensation with a phenol such as 2,4,5-trichlorophenol, pentachlorophenol, 2-nitrophenol or 4-nitrophenol or an N-hydroxy compound such as N-succinimide, N-hydroxy-5-norbornen-endo-2,3-dicarboxyimide, 1-hydroxybenztriazole or N-hydroxypiperidine in the presence of a reagent such as dicyclohexylcarbodiimide to convert into an active ester thereof, followed by condensation. Alternatively, the compound (II) is allowed to react with isobutyl chloroformate to give a mixed acid anhydride, which is then subjected to condensation.

The condensation between the compound (II) or a reactive derivative thereof and the compound (III) can also be performed by using singly a peptide-formation reagent such as dicyclohexylcarbodiimide, N,N'-carbonyldiimidazole, diphenylphosphoryl azide or diethyl cyanophosphate.

In said condensation reaction, the amidino group, guanidino group or amino group present in the compound (II), a reactive derivative thereof or the compound (III) are preferably present as the salt of an inorganic acid (e.g. hydrogen chloride, sulfuric acid, nitric acid or hydrobromic acid) or protected with tert-butoxycarbonyl group or benzyloxycarbonyl group.

And, in said condensation reaction, the carboxyl group present in the compound (II), a reactive derivative thereof or the compound (III) is desirably present as the salt of an inorganic acid (e.g. hydrogen chloride, sulfuric acid, nitric acid or hydrobromic acid) or protected with methyl, ethyl, benzyl or tert-butyl group.

And, in said condensation reaction, the hydroxyl group present in the compound (II) a reactive derivative thereof or the compound (III) is desirably present as the salt of an inorganic acid (e.g. hydrogen chloride, sulfuric acid, nitric acid or hydrobromic acid) or protected with benzyl or tert-butyl group.

Any of the above-mentioned condensation reactions can be promoted by the addition of preferably an organic base (e.g. triethylamine, N-methylpiperidine, 4-N,N-dimethylaminopyridine) or an inorganic base (sodium hydrogencarbonate, sodium carbonate, potassium carbonate). The reaction temperature ranges usually from −20° to +50° C., preferably from 0° C. to about +30° C. The reaction time varies depending on kinds of the solvents (including mixing ratio in the case of a mixed solvent) and reaction temperature, which ranges usually from one minute to 72 hours, preferably from about 15 minutes to 5 hours. Examples of solvents usually employed include water, dioxane, tetrahydrofuran, acetonitrile, pyridine, N,N-dimethylformamide, dimethyl sulfoxide, N-methylpyrrolidone, chloroform and methylene chloride, and these can be used singly or as a mixture.

The protective group of the carboxyl group contained in the product of the final method (benzyl group or tert-butyl group, which is the protective group of the carboxyl group of Y in the general formula (I)) can be removed by a per se known method. For example, a compound having a benzyl ester group can be converted to a carboxylic acid derivative by subjecting the compound to hydrogenation in the presence of a precious metal catalyst such as palladium or platinum, and a compound having a tert-butyl ester group can be converted to a carboxylic acid derivative by processing the compound with an acid such as trifluoroacetic acid or hydrogen chloride.

The protective group of the amino group contained in the product in the final method (tert-butoxycarbonyl group or benzyloxycarbonyl group, which is the protective group of the amino group of X' in the below reaction schema) can be removed by a per se known method. For example, the tert-butoxycarbonyl group can be readily removed by processing the compound containing the group with an acid such as trifluoroacetic acid or hydrogen chloride in an organic solvent (e.g. methanol, ethanol, ethyl acetate and dioxane). And, the benzyloxycarbonyl group can be removed by subjecting the compound containing the group to catalytic reduction in the presence of a metal such as platinum, palladium or Raney nickel or a mixture of such metal and an optional carrier.

While salts of the compound (I) can be obtained by the reaction for producing the compound (I) itself, they can be produced also by adding, upon necessity, an acid, alkali or base.

Thus-obtained compound (I) to be used in this invention can be isolated from the reaction mixture by a conventional separation and purification means such as extraction, concentration, neutralization, filtration, recrystalization, column chromatography and thin-layer chromatography.

In the compound (I), at least two stereoisomers can be present. These individual isomers or a mixture thereof are included in the scope of the present invention. And, it is also possible to produce these isomers individually.

By conducting the reaction as described using a single isomer of the compound (III), a single optical isomer of the compound (I) can be obtained.

And, when the product is a mixture of two or more isomers, it can be separated into respective isomers by a conventional separation method, for example, a method of causing formation of a salt with an optically active acid (e.g. camphor sulfonic acid, tartaric acid and dibenzoyl tartaric acid), an optically active base (e.g. cinchonine, cinchonidine, quinine, quinidine and α-methylbenzylamine), or various chromatographic means or fractional recrystallization.

The starting compounds (II) and (III) in the present invention are per se known compounds, or can be produced in a manner analogous to per se known methods. While the compound (III) can be produced by a method analogous to per se known methods, it can also be produced by the methods shown by the following reaction scheme.

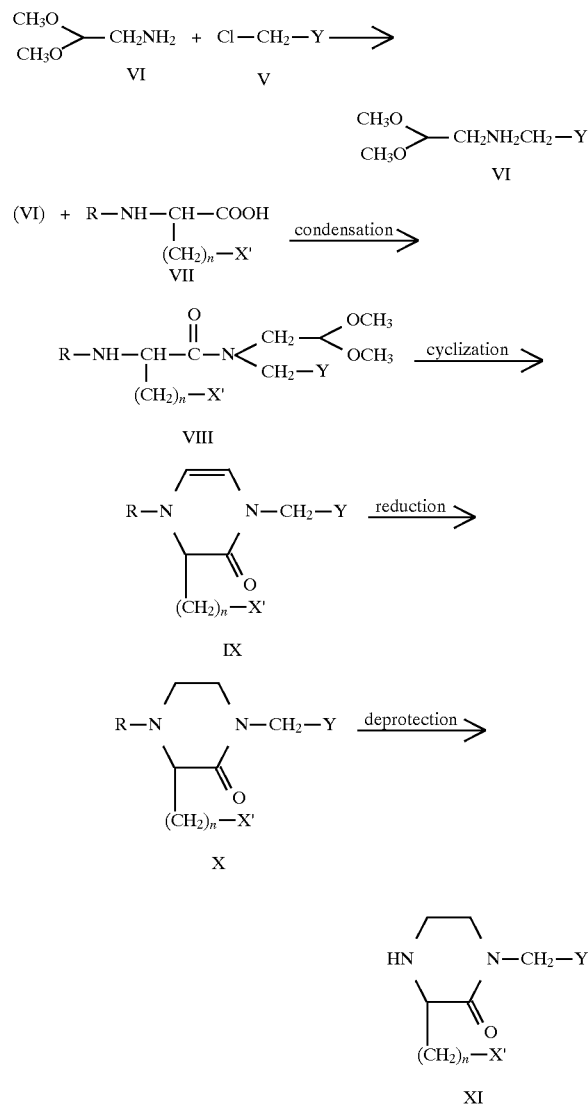

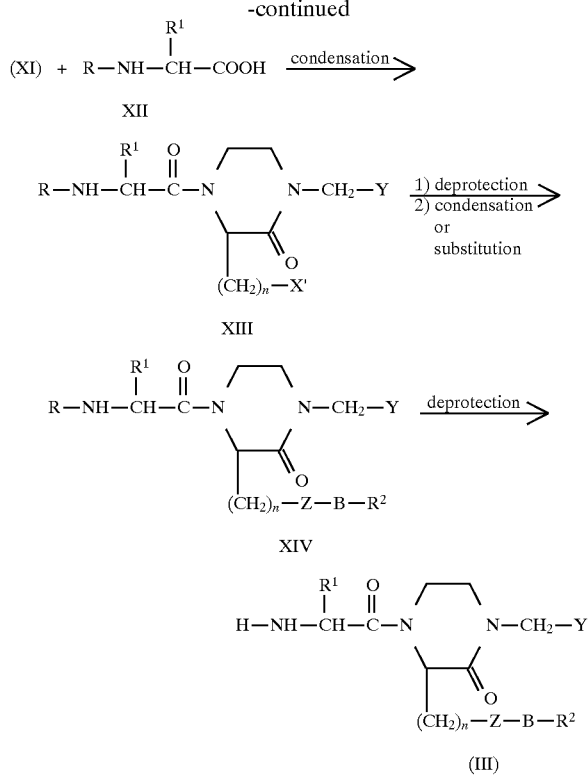

In the above reaction formulae, R is an amino-protective group, and stands for benzyloxycarbonyl group or tert-butoxycarbonyl group. X' stands for a protected amino group (as the protective group, use is made of, for example, benzyloxycarbonyl group and tert-butoxycarbonyl group), a protected carboxyl group (as the protective group, use is made of, for example, methyl, ethyl, benzyl and tert-butyl group), a protected hydroxyl group (as the protective group, use is made of, for example, benzyl group and tert-butyl group) or a protected mercapto group (as the protective group, use is made of, for example, benzyl group and trityl group). Y stands for a protected carboxyl group (as the protective group, use is made of, for example, benzyl or tert-butyl group).

The method of producing the compound (III) shown by the above reaction scheme is explained in further detail. The reaction for obtaining the compound (VI) by reacting the compound (IV) with the compound (V) is a conventional alkylation of an amino group. More specifically stating, the compound (IV) is allowed to react with the compound (V) usually at a temperature ranging from 0° to 100° C. for a period ranging from about 15 minutes to 5 hours in the presence of a base (e.g. an inorganic base such as sodium carbonate, potassium carbonate, potassium hydrogencarbonate or cesium fluoride, or an organic base such as triethylamine, pyridine or 4-N,N-dimethylaminopyridine) to give the compound (VI). As the reaction solvent, mention is made of an organic solvent such as acetonitrile, N,N-dimethylformamide, tetrahydrofuran, toluene and methylene chloride.

The subsequent reaction to produce the compound (VIII) by subjecting the compound (VI) to condensation with the compound (VII) is a conventional peptide-linkage reaction, which can be conducted under substantially the same reaction conditions as those for the condensation reaction of the compound (II) with the compound (III).

Cyclization of the compound (VIII) into the compound (IX) is a cyclization reaction with an acid catalyst. As the catalyst, use is made of, for example, p-toluenesulfonic acid, camphorsulfonic acid and methanesulfonic acid. The compound (IX) can be produced by conducting the reaction usually in a solvent such as toluene, benzene, ethyl acetate or 1,2-dichloroethane at a temperature ranging from 0° to 100° C., preferably from 30° to 80° C.

The subsequent reaction for reducing the compound (IX) to the compound (X) can be conducted by catalytic reduction using, as a catalyst, a metal such as platinum, palladium or Raney nickel, or a mixture of them with an optional carrier, or a reduction using a metallic hydride, for example, sodium borohydride. The above reactions are conducted usually in an organic solvent (e.g. methanol, ethanol, dioxane and ethyl acetate), and the reaction temperature ranges, in general, preferably from about −20° to about 100° C. This reaction can be conducted under normal pressure or under elevated pressure. When R is benzyloxycarbonyl group, the reaction of removing the protective group of R proceeds simultaneously to obtain the compound (XI).

Reactions for removing protective groups in (X) to (XI) and (XVI) to (III) are conventional reactions for removing protective groups of amino groups, and, in the case where R stands for a benzyloxycarbonyl group, the protective group can be removed by catalytic reduction using, as the catalyst, a metal such as platinum, palladium or Raney nickel or a mixture of the metal with an optional carrier. And, when R stands for tert-butoxycarbonyl group, the protective group can be easily removed by the use of an acid such as trifluoroacetic acid or hydrogen chloride in an organic solvent such as methanol, ethanol, ethyl acetate or dioxane.

The condensation reaction of the compound (XI) with the compound (XII) is an amide-linkage formation reaction, which can be conducted in substantially the same manner as in the condensation of the compound (II) with the compound (III).

The reaction for converting the compound (XIII) to the compound (XIV) can be conducted usually in two steps, i.e. deprotection and condensation or substitution reaction. In the case where X' is a protected amino group, the amino group is deprotected under substantially the same conditions as in the conversion of the compound (X) into the compound (XI), which is then condensed with a corresponding carboxylic acid under substantially the same conditions as in the condensation of the compound (II) with the compound (III), or subjected to substitution reaction with a corresponding halogenide under substantially the same conditions as in the reaction employed for the substitution reaction of the compound (IV) and the compound (V). When X' is a protected carboxyl group, the protecting group can be removed by a per se known method. For example, the protective group is methyl or ethyl ester, it can be removed by allowing a base such as sodium hydroxide, potassium hydroxide or lithium hydroxide to act in an organic solvent such as methanol ethanol, tetrahydrofuran and dioxane. And, a compound having a benzyl ester group, the compound can be converted into a carboxylic acid derivative by subjecting to hydrogenation in the presence of a precious metal catalyst such as palladium and platinum, and a compound having a tert-butyl ester group can be converted into a carboxylic acid derivative by processing with an acid such as trifluoroacetic acid or hydrogen chloride. The thus-obtained carboxylic acid can be converted to the compound (XIV) by condensing with a corresponding amine or hydroxy compound by the method employed for the condensation of the compound (II) with the compound (III).

In the above-mentioned methods of producing the compound (I) and its intermediates, compounds to be employed in the reactions may, unless undesirable effects are brought about, be in the form of a salt with, for example, an inorganic acid such as hydrochloride, hydrobromide, sulfate, nitrate or phosphate, an organic acid such as acetate, tartrate, citrate, fumarate, maleate, toluenesulfonate or methanesulfonate, a metal salt such as sodium salt, potassium salt or aluminum salt, or a salt with a base such as triethylamine salt, guanidine salt, ammonium salt, hydrazine salt or quinine salt.

When the compound (I) is obtained in the free form by the above-mentioned production method, it can be converted to a salt thereof by a conventional method, and when the compound (I) is obtained as a salt, it can be converted to the compound (I) by a conventional method.

The compounds (I) (including their salts and hydrates) are low in toxicity and are used safely, which inhibit both the binding of fibrinogen, fibronectin and von Willebrand factor to the fibrinogen receptor of blood platelets (Glycoprotein IIb/IIIa) and the binding thereof and other adhesive proteins, such as vitronectin, collagen and laminin, to the corresponding receptors on the surface of various types of cells.

While the amount of the above-mentioned amorphous water-soluble compound (I) to be employed varies with, for example, kinds of the compound (I) and desired pharmacological effects and duration, it ranges, in terms of the concentration in the solution of a polymer in an organic solvent, from about 0.001% to 90% (w/w), more preferably from about 0.01% to 80% (w/w), especially preferably from about 0.01% to 70% (w/w).

The said amorphous water-soluble compound (I) is used in the form of microparticles. The average particle size of the microparticles ranges, in general, less than 30 µm, usually from about 1 nm to about 10 µm, preferably less than 5 µm, more preferably from about 1 nm to about 1 µm.

The polymer to be employed in the present invention is a hardly water-soluble or water insoluble polymer having biocompatibility. Examples of the polymer are biodegradable polymers and more specifically include poly fatty acid ester (e.g. polylactic acid, polyglycolic acid, polycitric acid, polymalic acid and polylactic acid caprolactone), poly-α-cyanoacrylic acid ester, poly-β-hydroxybutyric acid, polyalkylene oxalate (e.g. polytrimethylene oxalate and polytetramethylene oxalate), poly ortho-ester, poly ortho-carbonate or other polycarbonate (e.g. polyethylene carbonate and polypropylene carbonate), polyamino acid (e.g. poly-γ-benzyl-L-glutamic acid, poly-L-alanine and poly-γ-methyl-L-glutamic acid) and hyaluronic acid ester. Furthermore, other polymers having biocompatibility are exemplified by polystyrene, polymethacrylic acid, copolymers of acrylic acid, polyamino acid, dextran stearate, ethyl cellulose, maleic anhydride copolymers, ethylene-vinylacetate copolymers, polyvinylacetate and polyacrylamide.

These polymers may optionally be used singly or as a copolymer of two or more of them or as a simple mixture of them or in the form of their salts.

Among these polymers, biodegradable ones are preferable especially when they are used as injectable preparations. In the case of, for example, lactic acid.glycolic acid copolymer (polymer) (PLGA), the biodegradability of the biodegradable polymer is defined as the percentage (w/w) of water-soluble low-molecular weight fragments degraded from PLGA relative to PLGA, and it should be not less than 10% in three months after subcutaneous or intramuscular administration, preferably not less than 80% in one year after subcutaneous or intramuscular administration. The said biodegradable polymer is preferably polyester. Preferred specific examples of the said biodegradable polymers include polymers or copolymers of hydroxycarboxylic acids or mixtures thereof.

While the hydroxycarboxylic acids are not necessarily specific ones, hydroxycarboxylic acids of the formula

HOCHCOOH wherein R represents hydrogen or an alkyl group are mentioned as preferable examples.

Preferable examples of the alkyl group represented by R in the above-mentioned formula include $C_{1-8}$ straight-chain or branched alkyl groups (e.g. methyl, ethyl, propyl, isopropyl, butyl, isobutyl, tert-butyl, pentyl, heptyl and octyl). Among them, $C_{1-3}$ straight-chain or branched alkyl groups are especially preferable.

Preferred examples of the above-mentioned hydroxycarboxylic acids include glycolic acid, lactic acid, hydroxybutyric acid (e.g. 2-hydroxybutyric acid), 2'-hydroxyvaleric acid, 2-hydroxy-3-methylbutyric acid, 2-hydroxycaproic acid and 2-hydroxycaprylic acid. Among them, especially, glycolic acid, lactic acid, 2-hydroxybutyric acid, 2-hydroxy-3-methylbutyric acid and 2-hydroxycaproic acid are preferable. And, glycolic acid, lactic acid and 2-hydroxybutyric acid are especially preferable. When these hydroxycarboxylic acids exist as D-isomers, L-isomers and D,L-isomers, any one of them may optionally be used, but, preferably D,L-isomers.

The copolymers may be any of random, block and graft ones. Among these glycolic acid copolymers, those whose biodegradability is relatively rapid and the release period when used singly is not longer than one month are preferred. Especially, lactic acid.glycolic acid copolymers or homopolymers (hereinafter, including copolymers and homopolymers of the respective acids, referred to briefly as copolymers) or hydroxybutyric acid.glycolic acid copolymers are preferable.

The polymer to be employed in the present invention can be synthesized without causing any problems by common synthetic methods [cf. e.g. JPA S61(1986)-28521].

The weight-average molecular weight of the polymer to be employed in the present invention ranges preferably from about 2000 to about 800000, more preferably from about 5000 to about 200000.

When lactic acid.glycolic acid copolymer (polymer) is used as the above-mentioned polymer, the molar ratio of lactic acid/glycolic acid ranges preferably from about 100/0 to about 25/75, more preferably from about 100/0 to about 50/50. The weight-average molecular weight of lactic acid.glycolic acid copolymer ranges from about 5000 to about 30000, more preferably from about 5000 to about 20000.

When hydroxybutyric acid.glycolic acid copolymer (polymer) (e.g. 2-hydroxybutyric acid.glycolic acid copolymer) is used as the above-mentioned polymer, the molar ratio of hydroxybutyric acid/glycolic acid ranges preferably from about 100/0 to about 25/75, more preferably from about 100/0 to about 50/50. Especially, the molar ratio of 2-hydroxybutyric acid/glycolic acid ranges preferably from about 60/40 to about 30/70. The weight-average molecular weight of hydroxybutyric acid.glycolic acid copolymer ranges from about 5000 to about 25000, more preferably from about 5000 to about 20000.

When butyric acid.glycolic acid copolymer is used as the above-mentioned polymer, the molar ratio of butyric acid/glycolic acid ranges preferably from about 100/0 to about 25/75.

When a mixture of polylactic acid (A) and glycolic acid2-hydroxybutyric acid copolymer (B), for example, is used as the above polymer, the mixing ratio shown by (A)/(B) ranges from about 10/90 to about 90/10 (by weight), preferably from about 25/75 to about 75/25 (by weight).

The weight-average molecular weight of polylactic acid ranges preferably from about 5000 to about 30000, more preferably from about 6000 to about 20000.

The molecular weight used herein means a molecular weight in terms of the molecular weight of polystyrene determined by gel permeation chromatography (GPC) using polystyrene as the standard material. The determination was carried out using GPC column KF 804L×2 (manufactured by Showa Denko K.K. Japan) and RI monitor L-3300 (Hitachi, Japan) and using chloroform as the mobile phase. In the present specification, more specifically, the weight-average molecular weight is based on polystyrene, obtained by gel permeation chromatography (GPC) with 9 polystyrenes as reference substances with weight-average molecular weights of 120,000, 52,000, 22,000, 9,200, 5,050, 2,950, 1,050, 580 and 162, respectively.

The polydispersity of the said polymer is defined as the value of weight average molecular weight/number average molecular weight, which ranges, in general, from 1 to 3.5, preferably from 1.5 to 2.5.

The amount of the polymer to be used depends upon, for example, the degree of the pharmacological activity of the physiologically active substance, release rate and release period of the said substance. For example, the polymer is used as the microcapsule base in an amount of about 0.2 to about 10000 times (by weight), preferably about about 1 to about 1000 times (by weight) relative to the weight of the physiologically active substance.

The concentration of the polymer in the oil phase is selected from the range of about 0.5 to about 90% (W/W), preferably about 2 to about 60% (W/W).

In order to inhibit the initial release of the water-soluble drug from the microcapsule, it is advantageous to add a basic substance or an oil and fat to the solution of this polymer in an organic solvent. Examples of the basic substance include basic amino acids such as L-arginine, N-methylglucamine and L-lysine. Among these, L-arginine or N-methylglucamine is preferred. Examples of the oil and fat include vitamin E, medium chain triglycerides (miglyols), cholesterol and phospholipids. The concentration of the basic substance in the solution of a polymer in an organic solvent ranges from about 0.01% to about 20% (W/W), preferably from about 0.1% to about 5% (W/W), more preferably from about 0.1% to about 3% (W/W). The concentration of the oil and fat in the solution of a polymer in an organic solvent ranges from about 0.01% to about 30% (W/W), preferably from about 0.1 to about 20% (W/W), more preferably from about 0.2% to about 10% (W/W).

In the present invention, it is preferable to allow an osmotic pressure adjustor to be contained in the aqueous phase. Any osmotic pressure adjustor can be employed so long as it produces osmotic pressure in an aqueous solution thereof.

Examples of the osmotic pressure adjustors include water-soluble polyhydric alcohols, water-soluble monovalent alcohols, water-soluble inorganic materials (e.g. inorganic salts), water-soluble monosaccharides, disaccharides, oligosaccharides and polysaccharides or their derivatives, water-soluble organic acids or salts thereof, water-soluble amino acids, water-soluble peptides, proteins or their derivatives. Among them, water-soluble polyhydric alcohols, water-soluble inorganic materials, water-soluble monosaccharides, disaccharides, oligosaccharides and polysaccharides or their derivatives, water-soluble organic acids or their salts. Furthermore, salts, water-soluble polyhydric alcohols and water-soluble inorganic materials are especially preferable.

Examples of the above-mentioned water-soluble inorganic salts include halogenated alkali metals such as potassium chloride, sodium chloride, potassium bromide, sodium bromide, potassium iodide and sodium iodide, halogenated alkaline earth metals such as calcium chloride and magnesium chloride, alkaline metal sulfates such as sodium sulfate and potassium sulfate, alkaline earth metal sulfates such as magnesium sulfate and calcium sulfate, alkali metal phosphates such as potassium dihydrogenphosphate, dipotassium hydrogenphosphate, potassium phosphate, sodium dihydrogenphosphate, disodium hydrogenphosphate and sodium phosphate. Among them, sodium chloride is especially preferred.

Examples of the above-mentioned polyhydric alcohols include dihydric alcohols such as glycerin, pentahydric alcohols such as arabitol, xylitol and adonitol, and hexahydric alcohols such as mannitol and sorbitol. Among these, hexahydric alcohols are preferred.

Examples of the above-mentioned water-soluble monohydric alcohols include methanol, ethanol and isopropyl alcohol. Among these, ethanol is preferred.

Examples of the above-mentioned water-soluble monosaccharides include pentoses such as arabinose, xylose, ribose and 2-deoxyribose, and hexoses such as glucose, fructose, galactose, mannose, sorbose, rhamnose and fucose. Among these, hexoses are preferred.

Examples of the above-mentioned water-soluble disaccharides include maltose, cellobiose, α-trehalose, lactose and sucrose. Among these lactose and sucrose are preferred.

Examples of the above-mentioned water-soluble oligosaccharides include trisaccharides such as maltotriose and raffinose, and tetrasaccharides such as stachyose. Among these, trisaccharides are preferred.

Examples of the above-mentioned water-soluble polysaccharides include glucans such as cellulose, starch and glycogen, galacturonans such as pectic acid, mannuronans such as alginic acid, fructans such as inulin and levan, N-acetylglycosamine polymers such as chitin, xylans such as xylan of rice straw, and diheteroglucans such as mannan, glucomannan, galactomannan, hyaluronic acid, chondroitin sulfate and heparin. Among these, glucans and diheteroglucans are preferred.

Examples of the derivatives of the above-mentioned water-soluble monosaccharides, disaccharides, oligosaccharides and polysaccharides include glucosamine, galactosamine, glucuronic acid and galacturonic acid.

Examples of the above-mentioned water-soluble organic acids or their salts include citric acid, tartaric acid, malic acid, and their alkali metal salts (e.g. sodium salts and potassium salts).

Examples of the above-mentioned water-soluble amino acids include neutral amino acids such as glycine, alanine, valine, leucine, isoleucine, phenylalanine, tyrosine, tryptophan, serine, threonine, proline, hydroxyproline, cysteine and methionine, acidic amino acids such as aspartic acid and glutamic acid, and basic amino acids such as lysine, arginine and histidine. Salts of these water-soluble amino acids with acids (e.g. hydrochloric acid, sulfuric acid and phosphoric acid) or alkalis (e.g. alkali metals such as sodium and potassium) are also used optionally.

Examples of the water-soluble peptides, proteins or their derivatives include casein, globulin, prolamins, albumin, gelatin, protamine and histone.

These osmotic pressure adjustors can be used alone or as a mixture of two or more of them. When the osmotic pressure adjustor is a non-ionic material, the concentration of the osmotic pressure adjustor in the outer aqueous phase ranges from about 0.001% to about 60% (W/W), preferably from about 0.01 to about 40% (W/W), more preferably from about 0.05 to about 30% (W/W). When the osmotic pressure adjustor is an ionic material, it is used in a concentration calculated by dividing the above-mentioned concentration by the total ionic valency. The concentration of the osmotic pressure adjustor to be added is not necessarily below their solubility, and a part of it may be left in the state of dispersion.

The microcapsules of the present invention can be prepared by, for example, an s/o/w type in-water drying process.

Initially, an amorphous water-soluble compound (I) is dispersed in a solution of a polymer in a water-insoluble organic solvent, then the resulting dispersion is mixed well to give an s/o type emulsion. In this emulsion, the compound (I) is dispersed substantially homogeneously in the polymer solution.

When the water-soluble compound (I) is available in amorphous state, it can be used as is. Even when it is available in crystalline form, it can be used after making it amorphous. The amorphous water-soluble compound (I) is preferably prepared by subjecting its aqueous solution, preferably its dilute aqueous solution to a rapid drying process such as freeze-drying or spray-drying. As described above, the amorphous water-soluble compound (I) is used preferably in the form of microparticles, and the average particle size of the compound (I) ranges generally from about 1 nm to about 30 μm, preferably from about 1 nm to about 5 μm. When the compound (I) is available in the form of microparticles, it can be used as is. When it is not available in the form of microparticles, it can be used after pulverizing it to microparticles by conventional methods (e.g. jet mill method, atomization or ball mill method).

Any water-insoluble solvent can be used so long as it dissolves the polymer and is insoluble in water. Examples of water-insoluble solvents include halogenated hydrocarbons (e.g. dichloromethane, chloroform, dichlorohexane, chloroethane, dichloroethane, trichloroethane and carbon tetrachloride), esters (e.g. ethyl acetate), ethers (e.g. ethyl ether), aromatic hydrocarbons (e.g. benzene and toluene) and hydrocarbons (e.g. n-pentane and n-hexane).

The emulsification of the above-mentioned s/o type emulsion can be carried out by a conventional dispersion technique, as exemplified by intermittent shaking, mixing by means of a mixer such as propeller-type stirrer or turbine-type stirrer, colloid mill operation, mechanical homogenization and ultrasonication. In this case, it is advantageous to use, when desired, the water-insoluble solvent in combination with a water-soluble solvent. Any water-soluble solvent can be employed so long as it is soluble in water and miscible with the above-mentioned water-insoluble solvent. Specific examples of the water-soluble solvent include alcohols (e.g. methanol, ethanol, propyl alcohol and isopropyl alcohol), acetone and acetonitrile. In the said s/o type emulsion, it is preferred to disperse more finely pulverized compound (I) having an average particle size ranging generally from about 1 nm to about 30 μm, preferable from about 1 nm to about 5 μm, most preferably about 1 nm to about 1 μm.

Subsequently, the s/o type emulsion thus prepared is subjected to in-water drying in an aqueous phase. Preferably, an osmotic pressure adjustor is present in the aqueous phase in the above-mentioned concentration. More specifically, the oil phase is added to the second aqueous phase containing the osmotic pressure adjustor to form an s/o/w type emulsion, followed by removing the solvent in the oil phase to prepare microcapsules.

An emulsifying agent may optionally be added to the outer aqueous phase in the s/o/w type in-water drying method. Any emulsifying agent can be used so long as it generally forms a stable o/w type emulsion. Specific examples of the emulsifying agent include anionic surfactants (e.g. sodium oleate, sodium stearate and sodium laurylsulfate), nonionic surfactants (e.g. polyoxyethylene-sorbitan fatty acid ester [e.g. Tween 60, Tween 80 (Atlas Powder Co.)], polyoxyethylene castor oil derivatives [e.g. HCO-60, HCO-50 (Nikko Chemicals, Japan)] or polyvinyl pyrrolidone, polyvinyl alcohol, carboxymethyl cellulose, lecithin and gelatin. These emulsifying agents can be used singly or in combination. They are used in a concentration appropriately selected from the range of about 0.01% to about 20% (W/W), more preferably about 0.05% to about 10% (W/W).

A conventional method is employed for removing the solvent in the oil phase. The removal of the solvent is conducted by, gradually reducing the pressure, while stirring the emulsion with a propeller-type stirrer or a magnetic stirrer, or, by using a rotary evaporator while controlling the vacuum extent. In this case, the time required for removing the solvent can be shortened by gradually warming the s/o/w type emulsion for the purpose of removing the solvent more completely at the time when the solidification of the polymer has proceeded to some extent and the loss of the compound (I) caused by its release from the internal phase has decreased. Alternatively, in the case where the thickening and solidification of the polymer is performed by a method other than that based on temperature, the solvent may be removed by merely leaving the s/o/w type emulsion to stand with stirring, or by warming the emulsion, or by spraying e.g. nitrogen gas. This step of removing the solvent is important and greatly influences the surface structure of microcapsules that controls the release of the compound (I). For example, rapid removal of the solvent produces many and larger pores on the surface to thereby increase the releasing rate of the compound (I).

The microcapsules thus prepared are collected by centrifugation or filtration. Then, the compound (I) and the substances that the compound (I) retains, which are attached onto the surface of the microcapsules are washed off with distilled water several times. Then, depending on necessity, water in the microcapsules and the solvent in the microcapsule preparation are removed more completely.

The microcapsules thus prepared are screened, when necessary after light pulverization, to remove those which are too large. The size of microcapsules varies with the desired degree of prolonged release, and, when the microcapsules are used as a suspension, the size is not specifically restricted so long as it falls in the range satisfying the dispersibility and needle-pass requirements. For example, the average diameter ranges preferably from about 0.5 to 400 μm, more preferably from about 2 to 200 μm.

The microcapsules prepared by the method of this invention can be administered, orally or parenterally, as they are or in the various dose form. For example, the microcapsules can be administered in the form of injections or implants intramuscularly, subcutaneously, or into blood vessels, organs or joint cavities or foci of tumors and the like. They can also be administered after molding into various preparations, or can be used as raw materials in the production of such preparations.

The above-mentioned preparations include injections, orally administrable preparations (e.g. powders, granules, capsules and tablets), nasal preparations, suppositories (e.g. rectal suppositories and vaginal suppositories).

For example, when the microcapsules of this invention are processed into injections, they are dispersed in an aqueous vehicle together with, for example, a dispersing agent [e.g. Tween 80, HCO 60 (manufactured by Nikko Chemicals), carboxymethyl cellulose and sodium alginate], a preservative (e.g. methylparaben, benzyl alcohol and chlorobutanol) and an isotonication agent (e.g. sodium chloride, glycerin, sorbitol and glucose) to prepare an aqueous suspension, or, they are dispersed in a vegetable oil such as olive oil, sesame oil, peanut oil, cotton seed oil and corn oil, or in propylene glycol to prepare an oily suspension, thus sustained-release injections being prepared.

An excipient (e.g. mannitol, sorbitol, lactose and glucose) is further added to the above-mentioned sustained-release injections, as the suspending agent to cause redipersion, which is then solidified by freeze-drying or spray-drying. The thus-solidified preparation is used by adding distilled water for injection or an adequate dispersing agent spontaneously. In this way, more stable sustained-release injections can be prepared.

The microcapsules of this invention can be processed into, for example, tablets by a method analogous to conventional methods. For example, to the microcapsules are added an excipient (e.g. lactose, crystalline cellulose, sucrose and starch such as corn starch), a disintegrant (e.g. starch such as corn starch, cross carmellose sodium, carboxymethyl starch sodium and calcium carbonate), a binder (e.g. crystalline cellulose, gum arabic dextrin, carboxymethyl cellulose, polyvinyl pyrrolidone and hydroxypropyl cellulose) or a lubricant (e.g. talc, magnesium stearate and polyethylene glycol 6000), then the mixture is subjected to compression molding.

For preparing the microcapsules of this invention into a composition for nasal administration, they are processed into solid, semi-solid or liquid preparations by conventional methods. For example, the solid composition for nasal administration can be prepared as a powdery composition from the microcapsules as they are or together with, for example, an excipient (e.g. glucose, mannitol, starch and microcrystalline cellulose) and a thickener (e.g. natural gum, cellulose derivatives and polyacrylates). The above-mentioned liquid composition can be prepared as an oily or aqueous suspension by substantially the same manner as in the case of preparing injections. The semi-solid composition for nasal administration is preferably an aqueous or oily gel preparation of an ointment. In any of the above cases, pH adjustors (e.g. carbonic acid, phosphoric acid, citric acid, hydrochloric acid and sodium hydroxide) and preservatives (e.g. p-hydroxybenzoic acid esters, chlorobutanol and chlorobutanol and benzalkonium chloride) may optionally be supplemented.

For preparing the microcapsules of this invention into a suppository, an oily or aqueous solid, semi-solid or liquid suppository can be prepared by a per se known method. Any the oleagenous base for the above-mentioned composition, one can be employed so long as it does not dissolve the microcapsules, as exemplified by higher fatty acid glycerides [cacao butter, Witepsol (Dynamit-Nobel, Germany)], medium chain triglycerides [e.g. Miglyol (Dynamit-Nobel, Germany)] or vegetable oil (e.g. sesame oil, soybean oil and cotton seed oil). The aqueous bases are exemplified by polyethylene glycol and propylene glycol, and the aqueous gel bases are exemplified by natural gum, cellulose derivatives, vinyl polymers and polyacrylates.

Since the microcapsules of this invention release a given amount of the drug over a long period, they exhibit a constant efficacy with low toxicity, and thus are expected as a safe and highly effective sustained-release preparation. For example, even in the case where bleeding is feared as a side-effect due to the antithrombotic activity of the drug, use of the microcapsules of this invention serves to maintain an effective concentration of the drug over a long period without any side effects. Therefore, as mentioned above, since the compound (I) inhibits the binding of fibrinogen to the fibrinogen receptor of blood platelets (Glycoprotein (GP) IIb/IIIa) and the binding of other adhesive proteins, to the corresponding receptos on the surface of various types of cells and prevents the development of thrombus, the microcapsules of the present invention can be used for treatment or prophylaxis of diseases such as angina pectoris, unstable angina, acute myocardial infarction, Kawasaki disease, acute or chronic heart failure, transient ischemic attack (TIA), cerebral apoplexy, cerebral ischemic disturbance in acute phase of cerebral thrombosis, dissecting aneurysm of the aorta, cerebral vasospasm after subarachnoid hemorrhage, acute or chronic renal disease (e.g. acute or chronic renal disease due to overagglutination such as snake venom and immunopathy), chronic and acute glomerulonephritis, diabetic nephropathy and nerve disturbance, nephrotic syndrome, liver diseases, pulmonary embolism, bronchial asthma, pulmonary edema, adult respiratory distress syndrome (ARDS), arteriosclerotic obliteration, peripheral arterial obstruction, deep vein thrombosis, vibration disease, peripheral obstruction complicated with diabetes mellitus, thrombotic thrombocytopenic purpura (TTP), disseminated intravascular coagulation (DIC), sepsis, surgical or infective shock, postoperative and post-delivery trauma, premature separation of placenta, incompatible blood transfusion, systemic lupus erythematosus, Raynaud's disease, inflammations, arteriosclerosis, hemolytic uremic syndrome, symmetric peripheral necrosis, bedsore and hemorrhoids in mammals including humans (e.g. mouse, rat, guinea pig, dog, rabbit and human). The microcapsules of this invention can be used for preventing thrombosis due to coronary bypass surgical operation, surgical operation for pump oxygenator, atrial fibrillation or fracture of hip joint, prosthetic valve replacement, artificial blood vessel and organs, or preventing thrombocytopenia during artificial dialysis, and further for secondary prophylaxis of myocardial infarction. The preventing thrombocytopenia during artificial dialysis also means preventing coagulation or non-washable blood in shunt of extracorporeal dialysis.

Further, the microcapsules of this invention can be used for coronary thrombolytic therapy (e.g. enhancing the action of thrombolytic agent such as tissue plasminogen activator (TPA)) and for preventing reobstruction, for preventing reobstruction and restenosis of coronary arteries after PTCA (percutaneous transluminal coronary angioplasty) or stent-indwelling and atherectomy, for preventing reobstruction and restenosis after a surgical operation for coronary artery bypass, for preventing ischemic complication (e.g. myocardial infarction, death) after PTCA or coronary thrombolytic therapy. Compound (I) also inhibits metastasis of tumors and can be used as an antitumor agent.

Especially, the microcapsules of the present invention are useful for the prophylaxis or treatment of thrombosis, angina pectoris, unstable angina or ischemic complication, reobstruction or restenosis after percutaneous transluminal coronary angioplasty or coronary thrombolytic therapy. The dosage of the microcapsule of the present invention for controlling or preventing the diseases referred to hereinbefore can vary within a wide range and can, of course, be adjusted to suit the individual circumstances in each particular case.

While the dosage of the sustained-release preparation of this invention varies with the types and structure of the compound (I) as the principal ingredient, dosage forms, duration of the release of the drug, subject animals (mammals, e.g. mouse, rat, horse, cow and human) and purposes of administration, it is effective if the principal ingredient is contained in an effective amount. For example, When administered orally to a patient with unstable angina, or, ischemic complication or reobstruction of coronary or restenosis of coronary after PTCA or coronary thrombolytic therapy, the unit dosage for an adult (body weight: 50 kg) is adequately selected from the range of about 1 mg to about 10 g, preferably about 10 mg to 2 g, of the microcapsules such that the dose per day of the compound (I) ranges from about 1 mg to 500 mg preferably about 10 mg to 200 mg. When administered non-orally to a patient with a transient ischemic attack (TIA), unstable angina, ischemic complication or reobstruction of coronary, restenosis of coronary after PTCA or coronary thrombolytic therapy, the volume of the suspension administer via injection can be appropriately selected from the range of about 0.1 to 5 ml, preferably about 0.5 to 3 ml such that the dose per day in terms of the compound (I) is about 0.05 to 50 mg, preferably about 1 to 20 mg/kg per day for an adult (50 kg).

Thus, pharmaceutical compositions can be prepared using the microcapsule which comprises the water soluble compound (I) in an effective therapeutic amount that is larger than a usual unit dose and a biocompatible polymer, which is capable of sustained release of the compound (I) over a long period.

The microcapsules of this invention have, for example, the following characteristic features:

(1) An amorphous water-soluble medicinal substance or drug can be entrapped into the microcapsule more efficiently and in a larger amount than the corresponding medicinal substance in a crystalline form.

1(2) The initial release of the medicinal substance after administration of the microcapsule can be reduced, whereby side-effects such as bleeding are suppressed.

(3) By using the microcapsules containing the medicinal substance in a high concentration, the total amount administered as a pharmaceutical composition can be reduced, thus serving to alleviate the pain or topical irritation at the site of subcutaneous administration.

EXAMPLES

The following experimental example, working examples and reference examples illustrate the present invention in further detail but are not to be construed to limit the scope thereof. In the working examples, all the percents (%) are indicated as weight/weight % unless otherwise specified.

Experimental Example

By following Example 1, using compound A in a crystalline form instead of amorphous compound A, the microcapsules containing crystalline compound A were obtained.

The ratio of the drug entrapped in the microcapsules and the initial release of one day were as shown below, compared with the microcapsules of Example 1.

| Drug Form | Ratio of Entrapped Drug | Initial Release |
|---|---|---|
| Crystalline | 67% | 46% |
| Amorphous | 78% | 9% |

From the results, it was shown that the amorphous drug is entrapped in the microcapsules in higher concentration and the initial release thereof is substantially reduced as compound to the crystalline drug.

Example 1

The fine powdery amorphous compound A (450 mg), prepared by freeze-drying, was dispersed in a solution of 4.05 g of lactic acid.glycolic acid copolymer (lactic acid/glycolic acid=75/25, weight average molecular weight calculated as polystyrene=10200) in 4 ml of methylene chloride. Thus-dispersed compound A, was pulverized by using Polytron, (Chinematica, Smitzerland) to microparticles, and was emulsified by using a homogenizer in 800 ml of a 0.1% aqueous solution, cooled at 15° C., of polyvinyl alcohol containing 2.7% of sodium chloride to give an s/o/w type emulsion. The emulsion was slowly stirred for 3 hours with a conventional propeller-type stirrer. After hardening of microcapsules with evaporation of methylene chloride, the microcapsules were collected by centrifugation and washed with purified water. The microcapsules thus collected were freeze-dried for a whole day and night to give a powdery product.

Determination of the ratio of the drug entrapped in the microcapsule and the releasability of the drug in vitro indicated that the drug entrapment was 78% and the initial release of one day was 9%.

Example 2

S/O/W Method: The fine powdery compound A (60 mg), prepared by freeze-drying, was dispersed in a solution of 1.94 g of a lactic acid.glycolic acid copolymer (lactic acid/glycolic acid=75/25, weight average molecular weight calculated as polystyrene=10200) in 2 ml of methylene chloride. Thus-dispersed compound A, was pulverized to microparticles by using Polytron, and was emulsified by using a homogenizer in 800 ml of a 0.1% aqueous solution, cooled at 15° C., of polyvinyl alcohol containing 2.7% of sodium chloride. The s/o/w type emulsion thus-prepared was subjected to substantially the same procedure as in Example 1 to prepare microcapsules containing the compound A. W/O/W Method: The compound A (60 mg) was dissolved in 1 ml of a 1% aqueous solution of acetic acid, which was mixed with a solution of 1.94 g of the above-mentioned lactic acid.glycolic acid copolymer (lactic acid/glycolic acid=75/25, weight average molecular weight calculated as polystyrene=10200) in 2 ml of methylene chloride. The compound in the mixture was pulverized to microparticles to give a w/o type emulsion. The w/o type emulsion was emulsified with a homogenizer in 800 ml of a 0.1% aqueous solution, cooled at 15° C., of polyvinyl alcohol containing 2.7% of sodium chloride. The w/o/w type emulsion thus-obtained was subjected to substantially the same procedure as in Example 1 to prepare microcapsules containing the compound A.

The determined releasabilities in vitro of the microcapsules prepared in the above-mentioned s/o/w type and w/o/w type indicated that the initial releases of one day were respectively 16% and 33%. In the microcapsules prepared by the s/o/w method of this invention, control of the initial release was possible.

Example 3

The finely pulverized compound B (450 mg), prepared by freeze-drying, was dispersed in a solution of 3.96 g of a lactic acid.glycolic acid copolymer (lactic acid/glycolic acid=50/50, weight average molecular weight calculated as polystyrene=9200) in 4 ml of methylene chloride in which L-arginine (90 mg) was previously dissolved. Thus-dispersed compound B was pulverized to microparticles with Polytron. The microparticles were emulsified, using a homogenizer, in 800 ml of a 0.2% aqueous solution, cooled at 15° C., of polyvinyl alcohol containing 2.7% of sodium chloride. The thus-prepared s/o/w type emulsion was subjected to substantially the same procedure as in Example 1 to prepare microcapsules containing the compound B.

Example 4

The fine powdery compound C (150 mg), prepared by spray-drying, was dispersed in a solution of 4.26 g of lactic acid.glycolic acid copolymer (lactic acid/glycolic acid=50/50, weight average molecular weight calculated as polystyrene=8000) in 4.5 ml of methylene chloride. Thus-dispersed compound C was pulverized to microparticles by using Polytron, which was emulsified by using a homogenizer in 800 ml of a 0.2% aqueous solution, cooled at 15° C., of polyvinyl alcohol containing 0.9% of sodium chloride to give an s/o/w type emulsion. The emulsion was slowly stirred for 3 hours with a conventional propeller-type stirrer. After hardening of microcapsules with evaporation of methylene chloride, the microcapsules were collected by centrifugation and washed with purified water. The microcapsules thus collected were freeze-dried, together with mannitol, for a whole day and night to give a powdery product.

Example 5

The fine powdery compound D (300 mg), prepared by freeze-drying, was dispersed in a solution of 4.20 g of a hydroxybutyric acid.glycolic acid copolymer (hydroxybutyric acid/glycolic acid=75/25, weight average molecular weight calculated as polystyrene=12000) in 5 ml of methylene chloride. Thus-dispersed compound D was pulverized to microparticles by using Polytron, which was emulsified by using a homogenizer in 1000 ml of a 0.2% aqueous solution, cooled at 15° C., of polyvinyl alcohol containing 1.8% of sodium chloride. The s/o/w type emulsion thus-prepared was subjected to substantially the same procedure as in Example 4 to prepare microcapsules containing the compound D.

Example 6

The finely pulverized compound E (200 mg), prepared by freeze-drying, was dispersed in a solution of 3.70 g of a lactic acid.glycolic acid copolymer (lactic acid/glycolic acid=90/10, weight average molecular weight calculated as polystyrene=8400) in 4 ml of methylene chloride in which N-methylglucamine (100 mg) was previously dissolved. Thus-dispersed compound was pulverized to microparticles with Polytron. The microparticles were emulsified, using a homogenizer, in 800 ml of a 0.1% aqueous solution, cooled at 15° C., of polyvinyl alcohol containing 2.7% of sodium chloride. The thus-prepared s/o/w type emulsion was subjected to substantially the same procedure as in Example 4 to prepare microcapsules containing the compound E.

Reference Example 1
(S)-3-(3-t-Butoxycarbonylaminopropyl)-2-oxopiperazine-1-acetic acid t-butyl ester oxalate In 54.6 cc of acetone was dissolved (2,2-dimethoxyethyl)aminoacetic acid t-butyl ester (6.0 g, 27.7 mmol) and N—Z—Orn(Boc)—OH (10.0 g, 27.7 mmol). To the solution was added, at 15° C. under stirring, 1-ethyl-3-(3-dimethylaminopropyl)-carbodiimide hydrochloride (5.6 g, 29.2 mmol). The mixture was stirred for one hour at room temperature, and concentrated under reduced pressure. The concentrate was dissolved in ethyl acetate, and washed with a 5% aqueous solution of potassium hydrogen sulfate and a saturated aqueous solution of sodium hydrogen carbonate. The organic layer was concentrated under reduced pressure to give a pale yellow oily substance. This oily substance and p-toluenesulfonic acid 1.0 hydrate (1.04 g, 5.46 mmol) were dissolved in 137 cc of toluene, and the solution was stirred for two hours at 70° C. The reaction mixture was poured into a saturated aqueous solution of sodium hydrogen carbonate and extracted with ethyl acetate. The organic layer was concentrated under reduced pressure, and purified by means of silica gel column chromatography (hexane/ethyl acetate= 3/2) to give 8.3 g of a pale yellow oily substance. This oily substance (8.3 g, 16.5 mmol) was dissolved in 166 cc of ethyl acetate, to which was added 1.7 g of 10% Pd-C, and then the mixture was stirred for two hours under a hydrogen atmosphere. The catalyst was filtered off, and the filtrate was dissolved in 16.6 cc of methanol. To the solution was added oxalic acid 2.0 hydrate (2.1 g, 16.5 mmol), and the mixture was concentrated under reduced pressure. The resulting crystalline product was washed with ethyl acetate to afford 5.1 g (66.8%) of the title compound as white crystals.

Specific optical rotation: $[\alpha]_D$ −29.3° (c=0.73, $H_2O$) m.p.: 181° C.

Elemental Analysis for $C_{18}H_{33}N_3O_5 \cdot (CO_2H)_2$ (461.511): Calcd.: C, 52.05; H, 7.64; N, 9.10 Found: C, 51.98; H, 7.61; N, 9.20.

Reference Example 2
(S)-4-Benzyloxycarbonylaminoacetyl-3-(3-t-butoxycarbonylaminopropyl)-2-oxopiperazine-1-acetic acid t-butyl ester In a saturated aqueous solution of sodium hydrogencarbonate was dissolved (S)-3-(3-t-butoxycarbonylaminopropyl)-2-oxopiperazine-1-acetic acid t-butyl ester oxalate (1.6 g, 3.47 mmol). The solution was subjected to extraction with ethyl acetate, and the extract solution was concentrated under reduced pressure. The concentrate and N—Z-Gly-OH (0.87 g, 4.16 mmol) were dissolved in 16.0 cc of acetone. To the solution was added, at 15° C. with stirring, 1-ethyl-3-(3-dimethylaminopropyl)-carbodiimide hydrochloride (0.87 g, 4.51 mmol). The mixture was stirred for one hour at room temperature, and the reaction mixture was concentrated under reduced pressure. The concentrate was washed with a 5% aqueous solution of potassium hydrogen sulfate and a saturated aqueous solution of sodium hydrogen carbonate. The organic layer was concentrated under reduced pressure, and the concentrate was purified by means of silica gel column chromatography (ethyl acetate) to afford 1.95 g (100%) of the title compound as a colorless amorphous powdery product. IR ν max $cm^{-1}$: 3360, 2970, 2930, 1713, 1650, 1513, 1448, 1363, 1246, 1158, 1045, 964, 848, 744, 695 NMR($CDCl_3$) δ: 1.43(9H,s), 1.46(9H,s), 1.50–2.20(4H,m), 3.02–4.28(10H,m), 4.52–4.80 (1H,m), 5.01(1H,dd,J=8.8,4.6Hz), 5.13(2H,s), 5.64–5.86 (1H,m), 7.37(5H,s)

Reference Example 3
(S)-4-(4-Amidinobenzoylamino)acetyl-3-(3-aminopropyl)-2-oxopiperazine-1-acetic acid trifluoroacetate In 13.4 cc of methanol was dissolved (S)-4-benzyloxycarbonylaminoacetyl-3-(3-t-butoxycarbonylaminopropyl)-2-oxopiperazine-1-acetic acid t-butyl ester (1.34 g, 2.38 mmol). To the solution was added 0.54 g of 10% Pd-C, and the mixture was stirred for 30 minutes under a hydrogen atmosphere. The catalyst was filtered off, and the filtrate was concentrated under reduced pressure. The concentrate and sodium hydrogen carbonate (0.4 g, 4.76 mmol) were dissolved in a mixture of 26.8 cc of water and 13.4 cc of 1,4-dioxane. To the solution was added, at room temperature with stirring, 4-amidinobenzoyl chloride hydrochloride (0.68 g, 3.09 mmol). The mixture was stirred for three hours, the pH of the reaction mixture was adjusted to 4 with 1N HCl, and was concentrated to dryness. The concentrate was dissolved in 3.75 cc of trifluoroacetic acid, and the solution was stirred for 2 hours at room temperature. The reaction mixture was concentrated under reduced pressure and purified by means of CHP-20 (Mitsubishi Chemical Industries, Ltd.) column chromatography (water) to afford 1.0 g (63.3%) of the title compound as a colorless amorphous powdery product.

Specific optical rotation: $[\alpha]_D$ +35.4° (c=0.75, MeOH)

Elemental Analysis for $C_{19}H_{26}N_6O_5.2CF_3CO_2H.H_2O$ (664.515): Calcd.: C, 41.57; H, 4.55; N, 12.65 Found: C, 41.86; H, 4.50; N, 12.60.

Reference Example 4

(S)-4-(4-Amidinobenzoyl)aminoacetyl-3-{3-(4-amidinobenzoyl)amino}propyl-2-oxopiperazine-1-acetic acid trifluoroacetate (Compound B)

In a mixture of 5.0 cc of water and 2.5 cc of 1,4-dioxane was dissolved (S)-4-(4-amidinobenzoylamino)acetyl-3-(3-aminopropyl)-2-oxo-piperazine-1-acetic acid trifluoroacetate (0.5 g, 0.94 mmol) and sodium hydrogen carbonate (0.32 g, 3.76 mmol). To the solution was added, at room temperature with stirring, 4-amidinobenzoyl chloride hydrochloride (0.22 g, 0.99 mmol). The mixture was stirred for two hours, the pH was adjusted to 4 with 1N HCl, and concentrated under reduced pressure. The concentrate was purified by means of CHP-20 column chromatography ($H_2O$ Right→5% $CH_3CN$) to afford 0.34 g (50.7%) of the title compound as a colorless amorphous powdery product.

Specific optical rotation: $[\alpha]_D$ +41.90° (c=0.73, MeOH)

Elemental Analysis for $C_{27}H_{32}N_8O_6.CF_3CO_2H.2H_2O$ (714.653):

Calcd.: C, 48.74; H, 5.22; N, 15.68 Found: C, 48.52; H, 5.22; N, 15.57.

Reference Example 5

(S)-3-(4-t-Butoxycarbonylaminobutyl)-2-oxopiperazine-1-acetic acid t-butyl ester oxalate In substantially the same manner as in Reference Example 1, the title compound was synthesized using N-Lys(Boc)—OH.

Specific optical rotation: $[\alpha]_D$ −29.0° (c=1.02, DMSO) m.p.: 170°–172° C.

Elemental Analysis for $C_{19}H_{35}N_3O_5.(CO_2H)_2$ (475.540):

Calcd.: C, 53.04; H, 7.84; N, 8.84 Found: C, 52.75; H, 7.65; N, 8.66.

Reference Example 6

(S)-4-Benzyloxycarbonylaminoacetyl-3-(4-t-butoxycarbonylaminobutyl)-2-oxopiperazine-1-acetic acid t-butyl ester In substantially the same manner as in Reference Example 2, the title compound was synthesized using (S)-3-(4-t-butoxycarbonylaminobutyl)-2-oxopiperazine-1-acetic acid t-butyl ester oxalate.

IR ν max cm$^{-1}$: 3400, 2990, 2945, 1713, 1657, 1520, 1458, 1368, 1253, 1166, 1070, 745, 700 NMR(CDCl$_3$) δ: 1.42(9H,s), 1.46(9H,s), 1.18–2.12(6H,m), 2.92–4.28(10H,m), 4.48–4.84(1H,m), 5.02(1H,dd,J=8.6,4.8Hz), 5.13(2H,s), 5.60–5.88(1H,m), 7.36(5H,s)

Reference Example 7

(S)-4-(4-Amidinobenzoylamino)acetyl-3-(4-aminobutyl)-2-oxopiperazine-1-acetic acid trifluoroacetate In substantially the same manner as in Reference Example 3, the title compound was synthesized using (S)-[4-benzyloxycarbonylaminoacetyl-3-(4-t-butoxycarbonylamino-butyl)-2-oxopiperazine-1-yl)-acetic acid t-butyl ester.

Specific optical rotation: $[\alpha]_D$ +46.80° (c=1.01, $H_2O$)

Elemental Analysis for $C_{20}H_{28}N_6O_5.1.7CF_3CO_2H.2H_2O$ (662.394):

Calcd.: C, 42.43; H, 5.13; N, 12.69 Found: C, 42.53; H, 4.88; N, 12.78.

Reference Example 8

(S)-4-(4-Amidinobenzoylamino)acetyl-3-{4-(4-amidinobenzoylamino)butyl}-2-oxopiperazine-1-acetic acid monotrifluoroacetate monohydrochloride In substantially the same manner as in Reference Example 4, the title compound was synthesized using (S)-4-(4-amidinobenzoylamino)acetyl-3-(4-aminobutyl)-2-oxopiperazine-1-acetic acid trifluoroacetate.

Specific optical rotation: $[\alpha]_D$ +44.3° (c=1.01, $H_2O$)

Elemental Analysis for $C_{28}H_{34}N_8O_6.CF_3CO_2H.HCl.3H_2O$ (783.157):

Calcd.: C, 46.01; H, 5.41; N, 14.31 Found: C, 46.23; H, 5.22; N, 14.54.

Reference Example 9

(S,S)-4-{2-Benzyloxycarbonylamino-3-(4-methoxyphenyl)propionyl}-3-(3-t-butoxycarbonylaminopropyl)-2-oxopiperazine-1-acetic acid t-butyl ester In substantially the same manner as in Reference Example 2, the title compound was synthesized using N-Z-Tyr(OMe)-OH. IR ν max cm$^{-1}$: 3360, 2975, 2925, 1710, 1643, 1512, 1448, 1360, 1245, 1152, 1033, 743, 696 NMR(CDCl$_3$) δ: 1.41(9H,s), 1.44(9H,s), 1.30–2.10(3H,m), 2.20–2.44(1H,m), 2.80–3.84(10H,m), 3.77(3H,s), 4.23(1H,d,J=17.2Hz), 4.50–4.85(1H,m), 4.93(1H,dd,J=6.2, 7.0Hz), 5.09(2H,dd,J=12.0, 16.4Hz), 5.67(1H,d,J=8.8Hz), 6.80(2H,d,J=8.8Hz), 7.09(2H,d,J=8.8Hz), 7.35(5H,s)

Reference Example 10

(S,S)-4-{2-(4-Amidinobenzoylamino)-3-(4-methoxyphenyl)-propionyl}-3-(3-aminopropyl)-2-oxopiperazine-1-acetic acid trifluoroacetate In substantially the same manner as in Reference Example 3, the title compound was synthesized using (S,S)-4-{2-benzyloxycarbonylamino-3-(4-methoxyphenyl)propionyl}-3-(3-t-butoxycarbonylaminopropyl)-2-oxopiperazine-1-acetic acid t-butyl ester.

Specific optical rotation: $[\alpha]_D$ +78.2° (c=0.62, $H_2O$)

Elemental Analysis for $C_{27}H_{34}N_6O_6.CF_3CO_2H.3H_2O$ (706.672): Calcd.: C, 49.29; H, 5.85; N, 11.89 Found: C, 49.53; H, 5.68; N, 11.90.

Reference Example 11

(S,S)-4-{2-(4-Amidinobenzoylamino)-3-(4-methoxyphenyl)-propionyl}-3-{3-(4-amidinobenzoylamino)propyl}-2-oxopiperazine-1-acetic acid trifluoroacetate In substantially the same manner as in Reference Example 4, the title compound was synthesized using (S,S)-4-{2-(4-amidinobenzoylamino)-3-(4-methoxyphenyl)propionyl}-3-(3-aminopropyl)-2-oxopiperazine-1-acetic acid trifluoroacetate.

Specific optical rotation: $[\alpha]_D$ +52.8° (c=0.76, MeOH)

Elemental Analysis for $C_{35}H_{40}N_8O_7.CF_3CO_2H.3H_2O$ (852.820): Calcd.: C, 52.11; H, 5.55; N, 13.14 Found: C, 52.27; H, 5.50; N, 13.26.

Reference Example 12
(S,S)-4-{2-Benzyloxycarbonylamino-3-(4-methoxyphenyl)-propionyl}-3-(4-t-butoxycarbonylaminobutyl)-2-oxopiperazine-1-acetic acid t-butyl ester In substantially the same manner as in Reference Example 2, the title compound was synthesized using (S)-3-(4-t-butoxycarbonylaminobutyl)-2-oxopiperazine-1-acetic acid t-butyl ester oxalate and N-Z-Tyr(OMe)-OH.

IR ν max cm$^{-1}$: 3345, 2975, 2930, 1712, 1646, 1512, 1447, 1364, 1244, 1155, 1034, 743, 696 NMR(CDCl$_3$) δ: 1.43(9H,s), 1.44(9H,s), 1.00–2.45(6H,m), 2.80–3.90(10H,m), 3.78(3H,s), 4.23(1H,d,J=17.4 Hz), 4.70–5.10(2H,m), 5.10(2H,d,J=2.4 Hz), 5.74(1H,d,J=8.8 Hz), 6.81(2H,d,J=8.6 Hz), 7.10(2H,d,J=8.6 Hz), 7.35(5H,s)

Reference Example 13
(S,S)-4-{2-(4-Amidinobenzoylamino)-3-(4-methoxyphenyl)propionyl}-3-(4-aminobutyl)-2-oxopiperazine-1-acetic acid trifluoroacetate In substantially the same manner as in Reference Example 3, the title compound was synthesized using (S,S)-[4-{2-benzyloxycarbonylamino-3-(4-methoxyphenyl)-propionyl}-3-(4-t-butoxycarbonylaminobutyl)-2-oxopiperazin-1-yl]-acetic acid t-butyl ester.

Specific optical rotation: $[\alpha]_D$ +53.1° (c=0.64, MeOH)

Elemental Analysis for $C_{28}H_{36}N_6O_6 \cdot CF_3CO_2H \cdot 3H_2O$ (720.699): Calcd.: C, 50.00; H, 6.01; N, 11.66 Found: C, 49.87; H, 5.77; N, 11.45.

Reference Example 14
(S,S)-4-{2-(4-Amidinobenzoylamino)-3-(4-methoxyphenyl)propionyl}-3-{4-(4-amidinobenzoylamino)butyl}-2-oxopiperazine-1-acetic acid hydrochloride In substantially the same manner as in Reference Example 4, the title compound was synthesized using (S,S)-4-{2-(4-amidinobenzoylamino)-3-(4-methoxyphenyl)propionyl}-3-(4-aminobutyl)-2-oxopiperazine-1-acetic acid trifluoroacetate.

Specific optical rotation: $[\alpha]_D$ +54.5° (c=0.88, H$_2$O)

Elemental Analysis for $C_{36}H_{42}N_8O_7 \cdot HCl \cdot 6H_2O$ (843.329): Calcd.: C, 51.27; H, 6.57; N, 13.29 Found: C, 51.24; H, 6.37; N, 13.26.

Reference Example 15
(S)-4-Benzyloxycarbonylaminoacetyl-3-{3-(6-t-butoxycarbonylaminohexanoylamino)propyl}-2-oxopiperazine-1-acetic acid In 3.0 cc of trifluoroacetic acid was dissolved (S)-4-benzyloxycarbonylaminoacetyl-3-(3-t-butoxycarbonylaminopropyl)-2-oxopiperazine-1-acetic acid t-butyl ester (0.6 g, 1.07 mmol), produced in Reference Example 2. The solution was stirred for 30 minutes at room temperature was concentrated under reduced pressure. In 2.1 cc of DMF was dissolved 6-t-butoxyaminocaproic acid (0.26 g, 1.12 mmol), 1-ethyl-3-(3-dimethylaminopropyl)-carbodiimide hydrochloride (0.22 g, 1.14 mmol) and 1-hydroxybenzotriazole (0.15 g, 1.12 mmol). The solution was stirred for one hour, to which was added 2.1 cc of a DMF solution of the concentrate obtained above, and tri-ethylamine (0.3 cc, 2.14 mmol). The mixture was stirred for 4 hours at room temperature. The reaction mixture was diluted with ethyl acetate, washed with a 5% aqueous solution of potassium hydrogen sulfate and a saturated aqueous solution of sodium hydrogen carbonate. The organic layer was concentrated under reduced pressure purified by silica gel column chromatography (ethyl acetate/methanol/acetic acid=20/10/0.6) to afford 0.42 g (y. 63.3%) of the title compound as a colorless amorphous powdery product.

IR ν max cm$^{-1}$: 3320, 2930, 1643, 1533, 1448, 1203, 1173, 1046 NMR(CDCl$_3$) δ: 1.42(9H,s), 1.20–2.09(10H,m), 2.17(2H,t,J=7.3 Hz), 2.92–4.20(12H,m), 4.80–4.98(1H,m), 5.11(2H,s), 7.22–7.44(5H,m)

Reference Example 16
(S)-4-(4-Amidinobenzoylamino)acetyl-3-{3-(6-aminohexanoylamino)propyl}-2-oxopiperazine-1-acetic acid trifluoroacetate In 8.4 cc of methanol was dissolved (S)-4-benzyloxycarbonylaminoacetyl-3-{3-(6-t-butoxycarbonylaminohexanoylamino)propyl}-2-oxopiperazine-1-acetic acid (0.42g, 0.68 mmol). To the solution was added 0.17 g of 10% Pd-C, and the mixture was stirred for one hour under a hydrogen atmosphere. The catalyst was filtered off, and the filtrate was concentrated under reduced pressure. The concentrate and sodium hydrogen carbonate (0.18 g, 2.14 mmol) were dissolved in a mixture of 8.4 cc of water and 4.2 cc of 1,4-dioxane. To the solution was added, with stirring at room temperature, 4-amidinobenzoyl chloride hydrochloride (0.20 g, 0.93 mmol). The mixture was stirred for one hour, the pH of the reaction mixture was adjusted to 4 with 1N HCl, and the resulting mixture was concentrated. The concentrate was dissolved in 4.3 cc of trifluoroacetic acid, and the solution was stirred for one hour at room temperature. The reaction mixture was concentrated under reduced pressure, purified by means of CHP-20 column chromatography (water→5% CH$_3$CN) to afford 0.26 g (y. 55%) of the title compound as a colorless amorphous powdery product.

Specific optical rotation: $[\alpha]_D$ +42.7° (c=0.99, MeOH)

Elemental Analysis for $C_{25}H_{37}N_7O_6 \cdot 1.1CF_3CO_2H \cdot 2H_2O$ (693.067): Calcd.: C, 47.14; H, 6.12; N, 14.15 Found: C, 47.30; H, 5.82; N, 14.40.

Reference Example 17
(S)-4-Benzyloxycarbonylaminoacetyl-3-{3-(5-t-butoxycarbonylaminopentanoylamino)propyl}-2-oxopiperazine-1-acetic acid In substantially the same manner as in Reference Example 15, the title compound was synthesized using 5-t-butoxyaminovaleric acid.

IR ν max cm$^{-1}$: 3370, 2940, 1650, 1533, 1455, 1254, 1170, 1050 NMR(CDCl$_3$) δ: 1.42(9H,s), 1.28–2.08(8H,m), 2.18(2H,t,J=7.0 Hz), 3.03(2H,t,J=6.8 Hz), 3.10–4.20(10H,m), 4.82–5.00(1H,m), 5.11(2H,s), 7.22–7.52(5H,m)

Reference Example 18
(S)-4-(4-Amidinobenzoylamino)acetyl-3-{3-(5-aminopentanoylamino)propyl}-2-oxopiperazine-1-acetic acid trifluoroacetate In substantially the same manner as in Reference Example 16, the title compound was synthesized using (S)-4-benzyloxycarbonylaminoacetyl-3-{3-(5-t-butoxycarbonylaminopentanoylamino)propyl}-2-oxopiperazine-1-acetic acid.

Specific optical rotation: $[\alpha]_D$ +46.0° (c=1.01, MeOH)

Elemental Analysis for $C_{24}H_{35}N_7O_6 \cdot CF_3CO_2H \cdot 2.5H_2O$ (676.646): Calcd.: C, 46.15; H, 6.11; N, 14.49 Found: C, 46.43; H, 6.15; N, 14.20.

Reference Example 19
(S)-4-Benzyloxycarbonylaminoacetyl-3-{3-(4-t-butoxycarbonylaminobutanoylamino)propyl}-2-oxopiperazine-1-acetic acid In substantially the same manner as in Reference Example 7, the title compound was synthesized using 4-t-butoxyaminobutyric acid.

IR ν max cm⁻¹: 3350, 2930, 1642, 1530, 1452, 1252, 1170, 1050 NMR(CDCl$_3$) δ: 1.42(9H,s), 1.30–2.10(4H,m), 1.73(2H,t,J=7.2 Hz), 2.18(2H,t,J=7.5 Hz), 3.04(2H,t,J=6.8 Hz), 3.10–4.20(10H,m), 4.83–4.97(1H,m), 5.11(2H,s), 7.22–7.50(5H,m)

Reference Example 20

(S)-4-(4-Amidinobenzoylamino)acetyl-3-{3-(4-aminobutanoylamino)propyl}-2-oxopiperazine-1-acetic acid trifluoroacetate In substantially the same manner as in Reference Example 16, the title compound was synthesized using (S)-4-benzyloxycarbonylaminoacetyl-3-{3-(4-t-butoxycarbonylaminobutanoylamino)propyl}-2-oxopiperazine-1-acetic acid.

Specific optical rotation: [α]$_D$ +47.9° (c=1.00, H$_2$O)

Elemental Analysis for C$_{23}$H$_{33}$N$_7$O$_6$·1.5CF$_3$CO$_2$H·2H$_2$O (710.623): Calcd.: C, 43.95; H, 5.46; N, 13.80 Found: C, 44.23; H, 5.63; N, 13.52.

Reference Example 21

(S,S)-4-{2-(4-Amidinobenzoylamino)-3-(4-methoxyphenyl)propionyl}-3-(4-guanidinobutyl)-2-oxopiperazine-1-acetic acid hydrochloride In 2.0 cc of trifluoroacetic acid was dissolved (S,S)-4-{2-benzyloxycarbonylamino-3-(4-methoxyphenyl)propionyl}-3-(4-t-butoxycarbonylaminobutyl)-2-oxopiperazine-1-acetic acid t-butyl ester (0.6 g, 0.86 mmol). The solution was stirred for one hour at room temperature, then concentrated under reduced pressure. An aqueous solution (5.6 cc) of the concentrate and sodium hydrogen carbonate (0.22 g, 2.57 mmol) was added to 5.6 cc of an aqueous solution of S-methylisothiourea sulfate (0.48 g, 1.71 mmol) and 2N NaOH (0.86 cc, 1.71 mmol). The mixture was stirred for 14 hours at room temperature. The resulting precipitates were collected by filtration, washed with water and dried. This solid product was dissolved in 5.8 cc of methanol, to which was added 0.12 g of 10% Pd-C, and the resulting mixture was stirred for one hour under a hydrogen atmosphere. The catalyst was filtered off, and the filtrate was concentrated under reduced pressure. The concentrate was purified by means of CHP-20 column chromatography (water→5%CH$_3$CN→10%CH$_3$CN) to afford (S,S)-4-{2-amino-3-(4-methoxyphenyl)propionyl}-3-(4-guanidinobutyl)-2-oxopiperazine-1-acetic acid. This intermediate (0.16 g, 0.36 mmol) and sodium hydrogen carbonate (0.09 g, 1.07 mmol) were dissolved in a mixture of 3.2 cc of water and 1.6 cc of 1,4-dioxane. To the solution was added, with stirring at room temperature, 4-amidinobenzoylchloride hydrochloride (0.10 g, 0.46 mmol). The mixture was stirred for 1.5 hours, the pH of the reaction mixture was adjusted to 4, and concentrated under reduced pressure. The concentrate was purified by means of CHP-20 column chromatography (water→5%CH$_3$CN) to afford 0.16 g (y. 27.3%) of the title compound as a colorless amorphous powdery product.

Specific optical rotation: [α]$_D$ +62.7° (c=0.99, MeOH)

Elemental Analysis for C$_{29}$H$_{38}$N$_8$O$_6$·HCl·3H$_2$O (685.176): Calcd.: C, 50.84; H, 6.62; N, 16.35 Found: C, 50.76; H, 6.47; N, 16.11.

Reference Example 22

(S)-4-(4-Amidinobenzoylamino)acetyl-3-{3-(4-guanidinobutanoylamino)propyl}-2-oxopiperazine-1-acetic acid hydrochloride (Compound E)

In 6.6 cc of trifluoroacetic acid was dissolved (S)-4-benzyloxycarbonylaminoacetyl-3-{3-(4-t-butoxycarbonylaminobutanoylamino)propyl}-2-oxopiperazine-1-acetic acid (0.33 g, 0.56 mmol) produced in Reference Example 16. The solution was stirred for one hour at room temperature, then the reaction mixture was concentrated under reduced pressure. An aqueous solution (3.3 cc) of the concentrate and sodium hydrogen carbonate (0.14 g, 1.68 mmol) was added to 3.3 cc of an aqueous solution of S-methyl isothiourea sulfate (0.93 g, 3.35 mmol) and 2N NaOH (1.68 cc, 3.35 mmol). The mixture was stirred for 14 hours at room temperature. The reaction mixture was concentrated under reduced pressure. The concentrate was purified by means of CHP-20 column chromatography (H$_2$O→5%CH$_3$CN→10%CH$_3$CN→15%CH$_3$CN) to give (S)-[4-(benzyloxycarbonylamino)-acetyl-3-{3-(4-guanidinobutylamino)-propyl}-2-oxopiperazin-1-yl]-acetic acid. This intermediate was dissolved in 6.0 cc of methanol, to which was added 0.30 g of 10% Pd-C, and the mixture was stirred for one hour under a hydrogen atmosphere. The catalyst was filtered off, and the filtrate was concentrated under reduced pressure. The concentrate and sodium hydrogen carbonate (0.19 g, 2.23 mmol) were dissolved in a mixture of 6.0 cc of water and 3.0 cc of 1,4-dioxane. To the solution was added, while stirring at room temperature, 4-amidinobenzoylchloride hydrochloride (0.16 g, 0.73 mmol). The mixture was stirred for one hour, the pH was adjusted to 4 with 1N HCl, and concentrated under reduced pressure. The concentrate was purified by means of CHP-20 column chromatography (H$_2$O) to afford 0.09 g (y.24.7%) of the title compound as a colorless amorphous powdery product.

Specific optical rotation: [α]$_D$ +48.4° (c=0.96, H$_2$O)

Elemental Analysis for C$_{24}$H$_{35}$N$_9$O$_6$·2HCl·3.5H$_2$O (681.572): Calcd.: C, 42.29; H, 6.51; N, 18.50 Found: C, 42.34; H, 6.59; N, 18.28.

Reference Example 23

4-(N-Benzyloxycarbonyl)glycyl-1-t-butoxycarbonylmethyl-2-oxopiperazine-3-acetic acid In a mixture of 5 ml of water and 5 ml of methanol was dissolved 1.46 g of 4-(N-benzyloxycarbonyl)glycyl-1-t-butoxycarbonylmethyl-2-oxopiperazine-3-acetic acid methyl ester. To the solution was added 190 mg of lithium hydroxide monohydrate at 0° C. in the course of five minutes. The mixture was stirred for one hour at 0° C., and then stirred for one hour at room temperature. The pH of the reaction mixture was adjusted to 7 with a 5% aqueous solution of potassium hydrogensulfate. The reaction mixture was concentrated under reduced pressure to eliminate methanol. To the concentrate was further added 5% potassium hydrogensulfate to adjust the pH to 3, which was subjected to extraction with ethyl acetate. The extract solution was dried over anhydrous magnesium sulfate and concentrated under reduced pressure to afford 1.1 g of the title compound as a colorless oily product.

NMR(CDCl$_3$) δ: 1.452(9H,s), 2.80–4.65(10H,m), 5.10 (2H,s), 5.82(1H,m), 6.03(1H,m), 7.33(5H,s) IR ν max' cm⁻¹: 3000, 1730, 1660, 1465, 1370, 1230, 1160.

Reference Example 24

3-(4-Amidinophenyl)aminocarbonylmethyl-4-(N-benzyloxycarbonyl)glycyl-2-oxopiperazine-1-acetic acid t-butyl ester In 5 ml of pyridine was dissolved 820 mg of 4-(N-benzyloxycarbonyl)glycyl-1-t-butoxycarbonylmethyl-2-oxopiperazine-3-acetic acid produced in Reference Example 5 and 370 mg of 4-aminobenzamidine dihydrochloride. To the solution were added 370 mg of dicyclohexyl carbodiimide and 10 mg of 4-dimethylaminopyridine. The mixture was stirred for 24 hours at room temperature. Insolubles were filtered off, and the filtrate was concentrated under reduced pressure to give a crude product, which was dissolved in a 1% aqueous solution of hydrochloric acid. The solution was subjected to CHP-20 column chromatography. Fractions eluted with 5% acetonitrile-water were collected and freeze-dried to afford 550 mg of the title compound as a colorless powdery product.

NMR(DMSO$_{d-6}$) δ: 1.42(9H,s), 2.83–4.44(13H,m), 5.02 (2H,s), 7.34(5H,s), 7.78–7.82(4H,m), 9.03–9.25(3H,m) IR ν max' cm$^{-1}$: 3325, 1730, 1680, 1640, 1480, 1365, 1260, 1155.

Reference Example 25

(S)-4-(N-(4-Amidinobenzoylamino)acetyl]-3-(4-amidinophenyl)aminocarbonylmethyl-2-oxopiperazine-1-acetic acid In 15 ml of methanol was dissolved 930 mg of 3-(4-amidinophenyl)aminocarbonylmethyl-4-(N-benzyloxy-carbonyl)glycyl-2-oxopiperazine-1-acetic acid t-butyl ester produced in Reference Example 12. To the solution was added 100 mg of 10% Pd-C, and the mixture was stirred for one hour under a hydrogen atmosphere. The catalyst was filtered off, and the filtrate was concentrated under reduced pressure to give an oily substance. The oily substance and 350 mg of sodium hydrogen carbonate were dissolved in a mixture of 25 ml of water and 15 ml of dioxane. To the solution was added, while stirring vigorously at room temperature, 307 mg of 4-amidinobenzoic acid in the course of 5 minutes. The reaction mixture was concentrated to give a crude product, which was dissolved in 5 ml of dichloromethane. To the solution was added 5 ml of trifluoroacetic acid at room temperature, and the mixture was stirred for one hour. The reaction mixture was concentrated under reduced pressure to give a crude product, which was purified by means of CHP-20 column chromatography to afford 490 mg of the title compound as a colorless powdery product.

Specific optical rotation: $[\alpha]_D^{23}$ +57.5° (c=0.9, H$_2$O)

Elemental Analysis for C$_{25}$H$_{28}$N$_8$O$_6$.CF$_3$CO$_2$H.2.7H$_2$O: Calcd.: C, 46.41; H, 4.96; N, 16.04 Found: C, 46.56; H, 4.80; N, 15.84.

Reference Example 26

(S)-4-(4-Guanidinobenzoylamino)acetyl-3-(3-(4-guanidinobenzoylamino)]propyl-2-oxopiperazine-1-acetic acid hydrochloride (Compound A)

In 4.9 ml of trifluoroacetic acid was dissolved 0.7 g of (S)-4-benzyloxycarbonylaminoacetyl-3-(3-t-butoxycarbonylamino)propyl-2-oxopiperazine-1-acetic acid t-butyl ester produced in Reference Example 2. The solution was stirred for one hour at room temperature. The reaction mixture was concentrated under reduced pressure, and then subjected to azeotropic distillation with toluene several times. The residue was subjected to CHP-20 (Mitsubishi Chemical Industries, Ltd.) column chromatography. Fractions eluted with 20% acetonitrile/water were combined and concentrated to give (S)-4-benzyloxycarbonylaminoacetyl-3-(3-amino)propyl-2-ox-opiperazine-1-acetic acid as a crude product. This crude product was dissolved in 12.0 ml of methanol, to which was added 250 mg of 10% Pd-C, and then the mixture was stirred for one hour under a hydrogen atmosphere. The catalyst was filtered off, and the filtrate was concentrated under reduced pressure. The concentrate and 836 mg of sodium hydrogen carbonate were dissolved in a mixture of 7.0 ml of 1,4-dioxane and 14.0 ml of water. To the solution was added, while stirring at room temperature, 1.27 g of 4-guanidinobenzoic acid N-hydroxy-5-norbornene-2,3-dicarboxylic acid imidoester hydrochloride. The mixture was stirred for one hour, the pH of the reaction mixture was adjusted to 3 to 4 with 1N hydrochloric acid, and concentrated under reduced pressure. The concentrate was subjected to CHP-20 column chromatography (eluted with 5% CH$_3$CN/H$_2$O). Relevant fractions were combined and freeze-dried to afford 0.48 g of the title compound as a colorless amorphous powdery product.

Specific optical rotation: $[\alpha]_D^{20}$ +56.3° (c=1.017, H70)

Elemental Analysis for C$_{27}$H$_{34}$N$_{10}$O$_6$.1.0HCl.3.5H$_2$O: Calcd.: C, 46.72; H, 6.10; N, 20.18 Found: C, 46.56; H, 6.17; N, 20.05.

Reference Example 27

(S)-3-(2-t-Butoxycarbonylamino)ethyl-2-oxopiperazine-1-acetic acid t-butyl ester oxalate In 200 ml of acetonitrile was dissolved 26 g of (S)-N$^2$-benzyloxycarbonyl-N-t-butoxycarbonyl-2,4-diaminobutanoic acid and 15.5 g of N-(2,2-dimethoxyethyl) glycine t-butyl ester. To the solution was added, while stirring at room temperature, 19 g of 1-ethyl-3-(3-dimethylaminopropyl)carbodiimide hydrochloride. The mixture was stirred for two hours at room temperature. The reaction mixture was then concentrated to an oily substance, which was dissolved in ethyl acetate. The solution was washed with a 5% aqueous solution of potassium hydrogen sulfate and, then, with a saturated aqueous solution of sodium hydrogen carbonate. The solution was dried over anhydrous magnesium sulfate and concentrated under reduced pressure. The concentrate was dissolved in 500 ml of toluene, to which was added 1.4 g of p-toluenesulfonic acid. The mixture was stirred for 3 hours at 70° C., cooled to room temperature and washed with a saturated aqueous solution of sodium hydrogen carbonate. The mixture was dried over anhydrous magnesium sulfate and concentrated under reduced pressure. The concentrate was dissolved in 500 ml of methanol, to which was added 10 g of 10% Pd-C. The mixture was stirred for 10 hours at room temperature under hydrogen atmosphere. The catalyst was filtered off. To the filtrate was added 6.4 g of oxalic acid, and the mixture was concentrated under reduced pressure to give a crude crystalline product. This crude product was recrystallized from methanol/ethyl acetate to afford 9.5 g of the title compound as colorless crystals.

m.p.: 165°–169° C.

Elemental Analysis for C$_{17}$H$_{31}$N$_3$O$_5$.(CO$_2$H)$_2$: Calcd.: C, 51.00; H, 7.43; N, 9.39 Found: C, 50.78; H, 7.59; N, 9.14.

Reference Example 28

(S)-4-(Benzyloxycarbonylamino)acetyl-3-(2-t-butoxycarbonylamino)ethyl-2-oxopiperazine-1-acetic acid t-butyl ester In 20 ml of dichloromethane was suspended 900 mg of (S)-3-(2-t-butoxycarbonylaminoethyl)-2-oxopiperazine-1-acetic acid t-butyl ester oxalate produced in Reference Example 12. To the suspension was added 20 ml of a saturated aqueous solution of sodium hydrogen carbonate, and the mixture was vigorously stirred for 10 minutes. The organic layer was separated and dried over anhydrous magnesium sulfate, to which was added 420 mg of N-benzyloxycarbonyl glycine and 500 mg of 1-ethyl-3-(3-dimethylaminopropyl)carbodiimide hydrochloride. The mixture was stirred for 2 hours at room temperature. The reaction mixture was concentrated under reduced pressure. The concentrate was dissolved in ethyl acetate then washed with 5% aqueous solution of potassium hydrogen sulfate and a saturated aqueous solution of sodium hydrogen carbonate. The concentrate was dried over anhydrous magnesium sulfate and concentrated under reduced pressure. The concentrate was purified by means of silica gel chromatography (eluent: ethyl acetate-hexane=3:1) to afford 1.05 g of the title compound as a colorless oily product.

IR ν max cm$^{-1}$: 3450, 1705, 1655, 1640, 1500, 1450, 1360, 1240, 1160 NMR(CDCl$_3$) δ: 1.43(9H,s), 1.46(9H,s), 2.05–2.33(1H,m), 2.73–2.95(1H,m), 3.15–4.20(10H,m), 5.05(1H,dd,J=3 Hz), 5.13(2H,s), 5.30(1H,brs), 5.83(1H, brs), 7.36(5H,s).

Reference Example 29

(S)-4-(4-Amidinobenzoylamino)acetyl-3-[2-(4-guanidinobenzoylamino)]ethyl-2-oxopiperazine-1-acetic acid hydrochloride (Compound D)

In 5 ml of trifluoroacetic acid was dissolved 550 mg of (S)-4-(N-benzyloxycarbonylamino)acetyl-3-(2-t-butoxycarbonylamino)ethyl-2-oxopiperazine-1-acetic acid t-butyl ester produced in Reference Example 28. The solution was stirred for one hour at room temperature. The reaction mixture was concentrated to give an oily substance. This oily substance and 400 mg of sodium hydrogen carbonate were dissolved in a mixture of 25 ml of water and 25 ml of dioxane. To the solution was added, while stirring at room temperature, 250 mg of 4-guanidinobenzoyl chloride hydrochloride. The pH of the reaction mixture was adjusted to pH 7 with 1N HCl, to which was added 100 mg of 10% Pd-C. The mixture was stirred for one hour under a hydrogen atmosphere. The catalyst was filtered off. To the filtrate was added 30 ml of dioxane and 400 mg of sodium hydrogencarbonate followed by addition of 230 mg of 4-amidinobenzoic acid hydrochloride with vigorously stirring. The reaction mixture was adjusted to pH 3 with 1N HCl and concentrated under reduced pressure to half of its initial volume. The concentrate was purified by means of CHP-20 column chromatography (5% acetonitrile/water) to afford 250 mg of the title compound as a colorless amorphous solid product.

Specific optical rotation: $[\alpha]_D^{20}$ +26.112° (c=0.450, MeOH)

Elemental Analysis for $C_{26}H_{31}N_9O_6 \cdot HCl \cdot 5H_2O$: Calcd.: C, 45.12; H, 6.12; N, 18.21 Found: C, 45.61; H, 6.06; N, 18.22.

Reference Example 30

(S)-4-Benzyloxycarbonylaminoacetyl-3-t-butoxycarbonylaminomethyl-2-oxopiperazine-1-acetic acid t-butyl ester In substantially the same manner as in Reference Examples 1 and 2, the title compound was produced as a colorless oily product using (S)-N$^2$-benzyloxycarbonyl-N$^3$-t-butoxycarbonyl-2,3-diaminopropanoic acid.

H$^1$-NMR(CDCl$_3$) δ: 1.38(9H,s), 1.47(9H,s), 3.19–4.20 (10H,m), 4.90–5.05(2H,m), 5.13(2H,s), 5.82(1H,brs), 7.36 (5H,s).

Reference Example 31

(S)-4-(4-Amidinobenzoylamino)acetyl-3-aminomethyl-2-oxopiperazine-1-acetic acid dihydrochloride The titled compound was produced as a colorless amorphous powdery product by subjecting (S)-4-benzyloxycarbonylaminoacetyl-3-t-butoxycarbonylaminomethyl-2-oxopiperazine-1-acetic acid t-butyl ester produced in Reference Example 30 to substantially the same procedure as in Reference Example 3.

Specific optical rotation: $[\alpha]_D^{20}$ +44.9° (c=0.655, MeOH)

Elemental Analysis for $C_{17}H_{22}N_6O_5 \cdot 2HCl \cdot 4H_2O$: Calcd.: C, 38.14; H, 6.02; N, 15.70 Found: C, 38.11; H, 5.65; N, 15.70.

Reference Example 32

(S)-4-(4-Amidinobenzoylamino)acetyl-3-(4-amidinobenzoylamino)methyl-2-oxopiperazine-1-acetic acid hydrochloride (S)-4-(4-Amidinobenzoylamino)acetyl-3-aminomethyl-2-oxopiperazine-1-acetic acid dihydrochloride produced in Reference Example 31 was subjected to substantially the same procedure as in Reference Example 4 to afford the title compound as a colorless amorphous powdery product.

Specific optical rotation: $[\alpha]_D^{20}$ +60.2° (c=0.535, MeOH)

Elemental Analysis for $C_{25}H_{28}N_8O_6 \cdot HCl \cdot 3H_2O$: Calcd.: C, 47.89; H, 5.63; N, 17.87 Found: C, 47.63; H, 5.36; N, 17.81.

Reference Example 33

(S)-4-(4-Amidinobenzoylamino)acetyl-3-[2-(4-amidinobenzoylamino)]ethyl-2-oxopiperazine-1-acetic acid trifluoroacetate (S)-4-(Benzyloxycarbonylamino)acetyl-3-(2-t-butoxycarbonylamino)ethyl-2-oxopiperazine-1-acetic acid t-butyl ester produced in Reference Example 28 was subjected to substantially the same procedure as in Reference Examples 3 and 4 to afford the title compound as a colorless amorphous powdery product.

Specific optical rotation: $[\alpha]_D^{20}$ +30.299° (c=0.470, H$_2$O)

Elemental Analysis for $C_{26}H_{30}N_8O_6 \cdot CF_3CO_2H \cdot 3H_2O$: Calcd.: C, 46.80; H, 5.19; N, 15.59 Found: C, 46.67; H, 4.99; N, 15.39.

Reference Example 34

(S)-4-(4-Guanidinobenzoylamino)acetyl-3-[2-(4-guanidinobenzoylamino)]ethyl-2-oxopiperazine-1-acetic acid trifluoroacetate (S)-4-(benzyloxycarbonylamino)acetyl-3-(2-t-butoxycarbonylamino)ethyl-2-oxopiperazine-1-acetic acid t-butyl ester produced in Reference Example 28 was subjected to substantially the same procedure as in Reference Example 26 to afford the title compound as a colorless amorphous powdery product.

Specific optical rotation: $[\alpha]_D^{20}$ +35.207° (c=0.650, H$_2$O)

Elemental Analysis for $C_{26}H_{32}N_{10}O_6 \cdot CF_3CO_2H \cdot 3H_2O$: Calcd.: C, 44.92; H, 5.25; N, 18.71 Found: C, 44.95; H, 5.54; N, 18.69.

Reference Example 35

(R)-4-(4-Amidinobenzoylamino)acetyl-3-(3-amino)propyl-2-oxopiperazine-1-acetic acid trifluoroacetic acid Z-D-Orn(Boc)-OH was subjected to substantially the same procedure as in Reference Examples 1, 2 and 3 to afford the title compound as a colorless amorphous powdery product.

Specific optical rotation: $[\alpha]_D^{20}$ –35.6° (c=0.519, MeOH)

Elemental Analysis for $C_{19}H_{26}N_6O_5 \cdot 2CF_3CO_2H \cdot 1.5H_2O$: Calcd.: C, 41.02; H, 4.64; N, 12.48 Found: C, 41.16; H, 4.47; N, 12.60.

Reference Example 36

(R)-4-(4-Amidinobenzoylamino)acetyl-3-[3-(4-amidinobenzoylamino)]propyl-2-oxopiperazine-1-acetic acid trifluoroacetate (R)-4-(4-Amidinobenzoylamino)acetyl-3-(3-amino)-propyl-2-oxopiperazine-1-acetic acid trifluoroacetic acid produced in Reference Example 35 was subjected to substantially the same procedure as in Reference Example 4 to afford the title compound as a colorless amorphous powdery product.

Specific optical rotation: $[\alpha]_D^{20}$ –41.6° (c=0.495, MeOH)

Elemental Analysis for $C_{27}H_{32}N_8O_6 \cdot CF_3CO_2H \cdot 4H_2O$: Calcd.: C, 46.40; H, 5.51; N, 14.93 Found: C, 46.66; H, 5.20; N, 14.90.

Reference Example 37
(S)-4-(4-Amidinobenzoylamino)acetyl-3-(3-(4-guanidinobenzoylamino)]propyl-2-oxopiperazine-1-acetic acid trifluoroacetate (S)-4-(Benzyloxycarbonylamino)acetyl-3-(3-t-butoxycarbonylamino)propyl-2-oxopiperazine-1-acetic acid t-butyl ester produced in Reference Example 2 was subjected to substantially the same procedure as in Reference Example 29 to afford the title compound as a colorless amorphous powdery product.

Specific optical rotation: $[\alpha]_D^{20}$ +48.60° (c=1.017, H$_2$O)
Elemental Analysis for C$_{27}$H$_{33}$N$_9$O$_6$.1.1CF$_3$CO$_2$H.1.5H$_2$O: Calcd.: C, 48.00; H, 5.30; N, 16.97 Found: C, 47.91; H, 5.11; N, 17.22.

Reference Example 38
(S)-4-(4-Amidinobenzoylamino)acetyl-3-(4-amidinophenylaminocarbonyl)ethyl-2-oxopiperazine-1-acetic acid trifluoroacetate (S)-4-Benzyloxycarbonylaminoacetyl-1-t-butoxycarbonylmethyl-2-oxopiperazine-3-propanoic acid methyl ester was subjected to substantially the same procedure as in Reference Example 23, 24 and 25 to afford the title compound as a colorless amorphous powdery product.

Specific optical rotation: $[\alpha]_D^{20}$ +59.625° (c=0.360, H$_2$O)
Elemental Analysis for C$_{26}$H$_{30}$N$_8$O$_6$.CF$_3$CO$_2$H.4H$_2$O: Calcd.: C, 45.65; H, 5.34; N, 15.21 Found: C, 45.70; H, 5.10; N, 14.91.

Reference Example 39
(S)-4-(4-Amidinobenzoylamino)acetyl-3-(4-amidinomethylbenzoylamino)methyl-2-oxopiperazine-1-acetic acid dihydrochloride (S)-4-Benzyloxycarbonylaminoacetyl-3-t-butoxycarbonylaminomethyl-2-oxopiperazine-1-acetic acid t-butyl ester produced in Reference Example 30, N-hydroxysuccinimide active ester of 4-amidinomethyl benzoic acid hydrochloride and 4-amidinobenzoyl chloride hydrochloride were subjected to substantially the same procedure as in Reference Example 29 to afford the title compound as a colorless amorphous powdery product.

Elemental Analysis for C$_{26}$H$_{30}$N$_8$O$_6$.2HCl.4.5H$_2$O: Calcd.: C, 44.32; H, 5.87; N, 15.90 Found: C, 44.23; H, 5.74; N, 15.88.

Reference Example 40
(S)-4-(4-Amidinobenzoylamino)acetyl-3-(4-guanidinomethylbenzoylamino)methyl-2-oxopiperazine-1-acetic acid dihydrochloride (S)-4-Benzyloxycarbonylaminoacetyl-3-t-butoxycarbonylaminomethyl-2-oxopiperazine-1-acetic acid t-butyl ester produced in Reference Example 30, N-hydroxysuccinimide active ester of 4-guanidinomethyl benzoic acid hydrochloride and 4-amidinobenzoyl chloride hydrochloride were subjected to substantially the same procedure as in Reference Example 29 to afford the title compound as a colorless amorphous powdery product.

Specific optical rotation: $[\alpha]_D^{20}$ +47.2° (c=0.553, H$_2$O)
Elemental Analysis for C$_{26}$H$_{31}$N$_9$O$_6$.2HCl.3H$_2$O: Calcd.: C, 45.09; H, 5.67; N, 18.20 Found: C, 45.32; H, 5.55; N, 18.10.

Reference Example 41
(S,S)-4-[2-(4-Amidinobenzoylamino)-3-(4-methoxyphenyl)]propionyl-3-[3-(6-aminohexanoylamino)]propyl-2-oxopiperazine-1-acetic acid trifluoroacetate (S,S)-4-{2-Benzyloxycarbonylamino-3-(4-methoxyphenyl)propionyl}-3-(3-t-butoxycarbonylaminopropyl)-2-oxopiperazine-1-acetic acid t-butyl ester produced in Reference Example 9 was subjected to substantially the same procedure as in Reference Example 15 and 16 to afford the titled compound as a colorless amorphous powdery product.

Specific optical rotation: $[\alpha]_D^{20}$ +57.3° (c=0.678, MeOH)
Elemental Analysis for C$_{33}$H$_{45}$N7O$_7$.CF$_3$CO$_2$H.2.5H$_2$O: Calcd.: C, 51.85; H, 6.34; N, 12.09 Found: C, 52.02; H, 6.25; N, 12.04.

Reference Example 42
(S,S)-4-[2-(4-Amidinobenzoylamino)-3-(4-methoxyphenyl)]propionyl-3-[4-(2-aminoacetylamino)]butyl-2-oxopiperazine-1-acetic acid trifluoroacetate (S,S)-4-[2-Benzyloxycarbonylamino-3-(4-methoxyphenyl)]propionyl-3-(4-t-butoxycarbonylamino)butyl-2-oxopiperazine-1-acetic acid t-butyl ester produced in Reference Example 14 and N-t-butoxycarbonyl glycine were subjected to substantially the same procedure as in Reference Example 15 and Reference Example 16 to afford the title compound as a colorless amorphous powdery product.

Specific optical rotation: $[\alpha]_D^{20}$ +59.8° (c=0.644, MeOH)
Elemental Analysis for C$_{30}$H$_{39}$N$_7$O$_7$.CF$_3$Co$_2$H. 2.5H$_2$O: Calcd.: C, 50.00; H, 5.90; N, 12.75 Found: C, 49.95; H, 5.72; N, 12.87.

Reference Example 43
4-(Amino-hydroxyimino)benzoic acid methyl ester

In 200 ml of methanol was dissolved 16.5 g of 4-cyanobenzoic acid methyl ester and 7.2 g of hydroxylamine hydrochloride. To the solution was added 8.82 g of sodium hydrogen carbonate at room temperature. The mixture was heated for 3 hours under reflux. The reaction mixture was cooled followed by addition of 400 ml of water. The resulting crystalline precipitate was collected by filtration, which was washed with water and ether and dried under reduced pressure to afford 16.1 g of the title compound as colorless needles.

m.p.: 170°–172° C.
Elemental Analysis for C$_9$H$_{10}$N$_2$O$_3$: Calcd.: C, 55.67; H, 5.19; N, 14.43 Found: C, 55.57; H, 5.22; N, 14.39.

Reference Example 44
4-(2,5-Dihydro-5-oxo-1,2,4-oxadiazol-3-yl)benzoic acid

In 30 ml of dioxane was suspended 5.83 g of 4-(amino-hydroxyimino)benzoic acid methyl ester produced in Reference Example 43 and 6 g of N,N'-carbonyldiimidazole, which was stirred for 30 minutes at 110° C. The reaction mixture was concentrated to dryness. The concentrate was dissolved in water and adjusted to pH 4 with acetic acid. The resulting crystals were collected by filtration and dissolved in 60 ml of 2N NaOH. The solution was stirred overnight at room temperature. To the reaction mixture was added acetic acid to adjust its pH to 4. The resulting crystalline precipitate was collected by filtration and washed with water, followed by recrystallization from dimethylformamide/ethyl acetate to afford 4.3 g of the title compound as a colorless crystalline product.

m.p.: not lower than 300° C. Elemental Analysis for C$_9$H$_6$N$_2$O$_4$: Calcd.: C, 52.44; H, 2.93; N, 13.59 Found: C, 52.14; H, 3.29; N, 13.89.

Reference Example 45
(S)-4-[4-(2,5-Dihydro-5-oxo-1,2,4-oxadiazol-3-yl)benzoylaminoacetyl-3-{3-[4-(2,5-dihydro-5-oxo-1,2,4-oxadiazol-3-yl)benzoylaminoj}propyl-2-oxopiperazine-1-acetic acid ammonium salt In 50 ml of methanol was dissolved 1 g of (S)-4-(benzyloxycarbonylamino)acetyl-3-(3-t- butoxycarbonylamino)propyl-2-oxopiperazine-1-acetic acid t-butyl ester produced in Reference Example 2. To the solution was added 0.2 g of 10% Pd-C, and the mixture was stirred for one hour under a hydrogen atmosphere. The catalyst was filtered off, and the filtrate was concentrated under reduced pressure. To the concentrate was added 4-(2,5-dihydro-5-oxo-1,2,4-oxadiazol-3-yl)benzoic acid produced in Reference Example 16. The mixture was dissolved in 20 ml of dimethylformamide. To the solution was added 0.36 g of 1-ethyl-3-(3-dimethylaminopropyl) carbodiimide hydrochloride (hereinafter referred to as WSC), and the resulting mixture was stirred for 3 hours at room temperature. The reaction mixture was concentrated under reduced pressure. The concentrate was purified by means of silica gel column chromatography (eluted with ethyl acetate—25% methanol/ethyl acetate) to give an oily product. This product was dissolved in 6 ml of trifluoroacetic acid and stirred for 2 hours at room temperature. The reaction mixture was concentrated under reduced pressure. The concentrate was dissolved in 8 ml of dimethylformamide, to which was added 1.25 ml of triethylamine. To the mixture was added a dimethylformamide solution of the active ester prepared from 0.33 g of 4-(2,5-dihydro-5-oxo-1,2,4-oxadiazol-3-yl) benzoic acid, 0.23 g of N-hydroxysuccinimide and 0.42 g of dicyclohexyl carbodiimide. The mixture was stirred for 3 hours at room temperature. Insolubles were filtered off, and the filtrate was concentrated under reduced pressure. The concentrate was dissolved in water and the pH was adjusted to 4 using acetic acid. The resulting precipitate was collected by filtration, and dissolved in water. The solution was adjusted to pH 8 using $NH_4$ or ammonium hydroxide and subjected to XAD-2 column chromatography. Fractions eluted with 10% acetonitrile/water were combined and freeze-dried to afford 0.114 g of the title compound as a colorless amorphous powdery product.

Specific optical rotation: $[\alpha]_D^{20}$ +49.9° (c=0.522, MeOH)
Elemental Analysis for $C_{29}H_3,N_9O_{10}.3.5H_2O$: Calcd.: C, 47.80; H, 5.26; N, 17.30 Found: C, 47.87; H, 5.12; N, 17.81.

Reference Example 46
4-Cyanobenzoic acid t-butyl ester

In 612 ml of methylene chloride was suspended 45.0 g of 4-cyanobenzoic acid and 3.1 ml of conc. sulfuric acid. To the suspension was added, while stirring at 0° C., 310 ml of isobutene. The mixture was stirred for 13 days. The reaction mixture was neutralized with a saturated aqueous solution of sodium hydrogen carbonate and extracted with ethyl acetate. The organic layer was concentrated under reduced pressure. The resulting precipitate was collected by filtration and washed with hexane. The filtrate and the washings were combined and concentrated under reduced pressure. The concentrate was purified by silica gel chromatography (hexane/ethyl acetate=10/1), followed by crystallization from methylene chloride/petroleum ether to afford 43.1 g of the title compound as a white crystalline product.

NMR(CDCl$_3$) δ: 1.61(9H,s), 7.72(2H,d,J=8.8 Hz), 8.08 (2H,d,J=8.8 Hz)

Reference Example 47
4-(Amino-hydroxyimino)methyl-benzoic acid t-butyl ester

In a mixture of 21.2 ml of t-butanol and 2.1 ml of water were dissolved 4.3 g of 4-cyanobenzoic t-butyl ester, 1.84 g of hydroxylamine hydrochloride and 2.31 g of sodium hydrogen carbonate. The solution was stirred for 2 hours at 80° C. To the reaction mixture was added water, and the mixture was subjected to extraction with ethyl acetate. The organic layer was concentrated under reduced pressure. The concentrate was purified by means of silica gel column chromatography (hexane/ethyl acetate=1/1), followed by crystallization from hexane to afford 4.41 g of the title compound as colorless needles.

m.p.: 153°–155° C.
Elemental Analysis for $C_{12}H_{16}N_2O_3$: Calcd.: C, 61.00; H, 6.83; N, 11.86 Found: C, 61.03; H, 6.70; N, 11.90.

Reference Example 48
4-(Amino-methoxycarbonyloxyiminomethyl)benzoic acid t-butyl ester In 8.46 ml of 1,4-dioxane were dissolved 1.0 g of 4-(amino-hydroxyimino)methyl-benzoic acid t-butyl ester and 292 mg of potassium carbonate. To the solution was added, while stirring at 0° C., 343 μL of methyl chloroformate. The mixture was stirred for one hour at room temperature. To the reaction mixture was added water. The resulting crystalline precipitate was collected by filtration and washed with water to afford 1.22 g of the title compound as a white crystalline product.

m.p.: 157°–159° C.
Elemental Analysis for $C_{14}H_{18}N_2O_5$: Calcd.: C, 57.14; H, 6.16; N, 9.52 Found: C, 56.98; H, 6.21; N, 9.30.

Reference Example 49
4-(Amino-methoxycarbonyloxyiminomethyl)benzoic acid trifluoroacetate In 4.0 ml of trifluoroacetic acid was dissolved 1.0 g of 4-(amino-methoxycarbonyloxyiminomethyl)benzoic acid t-butyl ester. The solution was stirred for one hour at room temperature. The reaction mixture was concentrated under reduced pressure. The concentrate was subjected to azeotropic distillation with toluene to afford 0.80 g of the title compound as a colorless amorphous powdery product.

Elemental Analysis for $C_{10}H_{10}N_2O_5.CF_3CO_2H$ (352.2233): Calcd.: C, 40.92; H, 3.15; N, 7.95 Found: C, 41.21; H, 2.98; N, 7.96.

Reference Example 50
(S)-4-[4-(Aminomethoxycarbonyloxyiminomethyl) benzoylamino]acetyl-3-{3-[4-(amino-methoxycarbonyloxyiminomethyl)-benzoylamino]}propyl-2-oxopiperazine-1-acetic acid (S)-4-(Benzyloxycarbonylamino)acetyl-3-(3-t-butoxycarbonylamino)propyl-2-oxopiperazine-1-acetic acid t-butyl ester produced in Reference Example 2 and 4-(amino-methoxycarbonyloxyiminomethyl)benzoic acid trifluoroacetate produced in Reference Example 20 were subjected to substantially the same procedure as in Reference Example 26 to afford the title compound as a colorless amorphous powdery product.

Specific optical rotation: $[\alpha]_D^{20}$ +50.5° (c=1.018, MeOH)
Elemental Analysis for $C_{31}H_{36}N_8O_{12}.2H_2O$: Calcd.: C, 49.73; H, 5.38; N, 14.97 Found: C, 49.54; H, 5.19; N, 14.87.

Reference Example 51
(S)-4-(4-Amidinobenzoylamino)acetyl-3-{3-[4-(amino-methxoycarbonyloxyiminomethyl)benzoylamino]}propyl-2-oxopiperazine-1-acetic acid hydrochloride (S)-4-(Benzyloxycarbonylamino)acetyl-3-(3-t-butoxycarbonylamino)propyl-2-oxopiperazine-1-acetic acid t-butyl ester produced in Reference Example 2,4-(amino-methoxycarbonyloxyiminomethyl)benzoic acid trifluoroacetate produced in Reference Example 49 and 4-amidinobenzoic acid were subjected to substantially the same procedure as in Reference Example 29 to afford the title compound as a colorless amorphous powdery product.

Specific optical rotation: $[\alpha]_D^{20}$ +47.5° (c=1.00, $H_2O$)

Elemental Analysis for $C_{29}H_{34}N_8O_9 \cdot HCl \cdot 3H_2O$: Calcd.: C, 47.77; H, 5.67; N, 15.37 Found: C, 47.51; H, 5.68; N, 15.27.

Reference Example 52
(S)-3-[3-(4-Amidinobenzoylamino)]propyl-4-benzyloxycarbonylaminoacetyl-2-oxopiperazine-1-acetic acid In 6.8 ml of trifluoroacetic acid was dissolved 1.35 g of (S)-4-benzyloxycarbonylaminoacetyl-3-(3-t-butoxycarbonylaminopropyl)-2-oxopiperazine-1-acetic acid t-butyl ester produced in Reference Example 2. The solution was stirred for one hour at room temperature and concentrated under reduced pressure. The concentrate was dissolved in a mixture of 20 ml of water and 10 ml of dioxane. To the solution was added stepwise 806 mg of sodium hydrogen carbonate and 683 mg of 4-amidinobenzoyl chloride hydrochloride. The mixture was stirred vigorously for 30 minutes. The reaction mixture was concentrated to give a crude product, which was purified by CHP-20 column chromatography (eluted with 20% acetonitrile/water) to afford 1.0 g of the title compound as a colorless amorphous powdery product.

Specific optical rotation: $[\alpha]_D^{20}$ +106.6° (c=0.478, 0.1N HCl)

Elemental Analysis for $C_{27}H_{32}N_6O_7 \cdot 2H_2O$: Calcd.: C, 55.09; H, 6.16; N, 14.28 Found: C, 55.36; H, 6.10; N, 14.35.

Reference Example 53
(S)-4-[4-(2-Aminoethyl)benzoylamino]acetyl-3-[3-(4-amidinobenzoylamino)]propyl-2-oxopiperazine-1-acetic acid trifluoroacetate (Compound C)

In 20 ml of methanol was dissolved 300 mg of (S)-3-[3-(4-amidinobenzoylamino)]propyl-4-benzyloxycarbonylaminoacetyl-2-oxopiperazine-1-acetic acid produced in Reference Example 21. To the solution was added 120 mg of 10% Pd-C, and the mixture was stirred for one hour at room temperature under a hydrogen atmosphere. The catalyst was filtered off, and the filtrate was concentrated under reduced pressure to give an oily product which was dissolved in 5 ml of dimethylformamide. To the solution was added 5 ml of an activated-ester solution in dimethylformamide, which activated-ester solution was prepared from 94 mg of N-hydroxysuccinimide and 173 mg of 4-(2-t-butoxycarbonylaminoethyl)benzoic acid in the presence of 167 mg of 1-ethyl-3-(3-dimethylaminopropyl) carbodiimide hydrochloride. The mixture was stirred for two hours at room temperature. The reaction mixture was concentrated to give an oily product, which was dissolved in 7 ml of trifluoroacetic acid. The solution was stirred for one hour at room temperature. The reaction mixture was concentrated under reduced pressure to give a crude product, which was purified by means of CHP-20 column chromatography (eluted with 10% acetonitrile/water) to afford 110 mg of the title compound as a colorless amorphous powdery product.

Specific optical rotation: $[\alpha]_D^{20}$ +41.7° (c=1.018, MeOH)

Elemental Analysis for $C_{28}H_{35}N_7O_6 \cdot 1.1CF_3CO_2H \cdot 4H_2O$: Calcd.: C, 47.53; H, 5.82; N, 12.85 Found: C, 47.64; H, 5.60; N, 12.72.

Reference Example 54
(S)-4-(4-Amidinobenzoylamino)acetyl-3-[3-(4-amidinobenzoylamino)]propyl-2-oxopiperazine-1-acetic acid hydrochloride In 5 ml of 0.5N hydrochloric acid was dissolved 1 g of (S)-4-(4-amidinobenzoylamino)acetyl-3-[3-(4-amidinobenzoylamino)]propyl-2-oxopiperazine-1-acetic acid trifluoroacetate produced in Reference Example 4. The solution was stirred for 5 minutes at 0° C. and adsorbed directly on a CHP-20 column. The column was washed with water until the eluate was pH neutral. The column was then eluted with 10% acetonitrile/water. Fractions of the eluate were combined and freeze-dried to afford 0.7 g of the title compound as a colorless amorphous powdery product.

Specific optical rotation: +51.3° (c=1.018, $H_2O$)

Elemental Analysis for $C_{27}H_{32}N_8O_6 \cdot HCl \cdot 5H_2O$: Calcd.: C, 46.92; H, 6.27; N, 16.21 Found: C, 47.13; H, 6.14; N, 16.23.

Reference Example 55
N-(4-t-butoxycarbonylphenyl)-N'-ethoxycarbonyl thiourea

In 150 ml of isopropyl ether was dissolved 13.51 g of 4-amino-benzoic acid t-butyl ester. To the solution was added, while stirring at room temperature, 9.83 g of ethoxycarbonyl isothiocyanate. The mixture was stirred for two hours, the resulting crystalline precipitate was collected by filtration and recrystallizated from isopropyl ether to give 21.83 g of the title compound as colorless needles.

m.p.: 119°–120° C.

Elemental Analysis for $C_{15}H_{20}N_2O_4S$: Calcd.: C, 55.54; H, 6.21; N, 8.64 Found: C, 55.56; H, 6.06; N, 8.65.

Reference Example 56
N-(4-butoxycarbonylphenyl)-N'-ethoxycarbonyl-S-methyl isothiourea In 80 ml of tetrahydrofuran was dissolved 21.7 g of N-(4-t-butoxycarbonylphenyl)-N'-ethoxycarbonyl thiourea produced in Reference Example 22. To the solution was added, at 0° C. (ice bath) while stirring, 2.68 g of a 60% dispersion of sodium hydride in oil which was previously washed with hexane. To the mixture was added dropwise a solution of 9.5 g of methyl iodide in 30 ml of hexane. The resulting mixture was stirred for one hour at 0° C. The reaction mixture was concentrated under reduced pressure, dissolved in ethyl acetate, washed with water then concentrated under reduced pressure. The concentrate was recrystallized from hexane to give 20 g of the title compound as colorless needles.

m.p.: 67°–68° C.

Elemental Analysis for $C_{16}H_{22}N_2O_4S$ Calcd.: C, 56.78; H, 6.55; N, 8.28 Found: C, 56.63; H, 6.31; N, 8.15.

Reference Example 57
3-(4-t-Butoxycarbonylphenylamino)-1,2,4-oxadiazolin-4H-5-one In 350 ml of methanol was dissolved 22.8 g of N-(4-butoxycarbonylphenyl)-N'-ethoxycarbonyl-S-methyl isothiourea produced in Reference Example 56 and 14 g of hydroxylamine hydrochloride. To the solution was added dropwise, at 0° C. (ice bath) while stirring 18 g of triethylamine. The mixture was stirred for 14 hours at room temperature. The reaction mixture was concentrated under reduced pressure dissolved in ethyl acetate, and washed with 1N hydrochloric acid. The organic layer was concentrated under reduced pressure to give a crude product, which was recrystallized from ethyl acetate—hexane to afford 7.8 g of the title compound as colorless prisms.

m.p.: 271°–272° C. (decomp.)

Elemental Analysis for $C_{13}H_{15}N_3O_4 \cdot 1/10H_2O$: Calcd.: C, 55.95; H, 5.49; N, 15.06 Found: C, 55.81; H, 5.47; N, 15.05.

Reference Example 58
3-(4-Carboxyphenylamino)-1,2,4-oxazolin-4H-5-one

In 70 ml of 1N NaOH was dissolved 7.7 g of 3-(4-t-butoxycarbonylphenylamino)-1,2,4-oxadiazolin-4H-5-one produced in Reference Example 24. The solution was stirred for 1.5 hour at 115° C. The reaction mixture was cooled and was neutralized with 2N HCl. The resulting precipitate was subjected to extraction with ethyl acetate. The extract solution was concentrated under reduced pressure to give a crude crystalline product, which was washed with ethyl acetate to afford 5.36 g of the title compound as yellow crystals.

m.p.: 272°–273° C. (decomp.)

Elemental Analysis for $C_9H_7N_3O_4$ Calcd.: C, 47.58; H, 3.40; N, 18.50 Found: C, 47.76; H, 3.39; N, 18.57.

Reference Example 59
4-Carboxyphenyl cyanamide

In 180 ml of tetrahydrofuran was dissolved 17.12 g of 4-amino(N-hydroxyimino)methylbenzoic acid methyl ester. To the solution was added 12.12 g of triethylamine. To the mixture was added dropwise, at 0° C. (ice bath), 12.65 g of methanesulfonyl chloride. The mixture was stirred for one hour at 0° C. then concentrated under reduced pressure. To the concentrate was added methanol. The resulting crystalline precipitate was collected by filtration and dissolved in 100 ml of methanol. To the solution was added, while stirring at room temperature, a solution of 12 g of sodium hydroxide in 100 g of water. The methanol was distilled off under reduced pressure. To the residue was added 700 ml of water. To this mixture was added, while stirring at room temperature, 80 ml of 4N HCl. The resulting crystalline precipitate was collected by filtration to give 13.12 g of the title compound as a colorless crystalline product.

m.p.: not lower than 300° C.

Elemental Analysis for $C_8H_6N_2O_2$ Calcd.: C, 59.26; H, 3.73; N, 17.28 Found: C, 58.97; H, 3.82; N, 17.04.

Reference Example 60
N-(4-carboxyphenyl)-N'-hydroxyguanidine

In 150 ml of methanol was dissolved 6.56 g of 4-carboxyphenyl cyanamide produced in Reference Example 26. To the solution was added, while stirring at room temperature, 6.1 g of hydroxylamine hydrochloride and 8.88 g of triethylamine. The mixture was stirred for two hours. The resulting crystalline precipitate was collected by filtration to afford 4.45 g of the title compound as a colorless crystalline product.

m.p.: 200°–202° C. (decomp.)

Elemental Analysis for $C_8H_9N_3O_3$ Calcd.: C, 48.78; H, 4.71; N, 21.33 Found: C, 48.55; H, 4.69; N, 21.09.

Reference Example 61
3-(4-Carboxyphenylamino)-5-trifluoromethyl-1,2,4-oxadiazole In 100 ml of tetrahydrofuran was dissolved 4.0 g of N-(4-carboxyphenyl)-N'-hydroxyguanidine produced in Reference Example 60. To the solution was added, while stirring at 0° C., 6.75 g of anhydrous trifluoroacetic acid. The mixture was stirred for 1.5 hour under the same conditions, followed by concentration under reduced pressure. To the concentrate was added water. The resulting crystalline product was collected by filtration and was recrystallized from ethyl acetate—hexane to afford 3.5 g of the title compound as a colorless crystalline product.

m.p.: 244°–246° C.

Elemental Analysis for $C_{10}H_6N_3O_3F_3$: Calcd.: C, 43.97; H, 2.21; N, 15.38 Found: C, 44.06; H, 2.31; N, 15.28.

Reference Example 62
4-t-Butoxycarbonyl benzaldoxime

In 100 ml of methanol was dissolved 20.5 g of 4-cyanobenzoic acid t-butyl ester and 13.9 g of hydroxylamine. To the solution was added, while stirring at room temperature, 128 g of triethylamine; The resulting mixture was stirred for one hour at 85° C. then concentrated under reduced pressure. The concentrate was dissolved in ethyl acetate, and the solution was washed with water. The organic layer was concentrated under reduced pressure to give a crude product, which was recrystallized from isopropyl ether to afford 11.45 g of the title compound as a colorless crystalline product.

m.p.: 113°–114° C.

Elemental Analysis for $C_{12}H_{16}N_2O_3 \cdot 1/10H_2O$: Calcd.: C, 60.54; H, 6.86; N, 11.77 Found: C, 60.77; H, 6.79; N, 11.57.

Reference Example 63
4-t-Butoxycarbonyl phenyl cyanamide

In 150 ml of ethyl acetate was dissolved 16.3 g of 4-t-butoxycarbonyl benzaldoxime produced in Reference Example 62. To the solution was added 13.7 ml of triethylamine. To the mixture was added dropwise, at 0° C. (ice bath), 9.92 g of methanesulfonyl chloride. The mixture was stirred for 0.5 hour under the same conditions. The reaction mixture was washed with water. The organic layer was concentrated under reduced pressure to leave an oily product. The oily product was dissolved in 150 ml of tetrahydrofuran, to which was added, while stirring at room temperature, 75 ml of 2N NaOH, followed by stirring for 0.5 hour. Tetrahydrofuran was then distilled off under reduced pressure. The residual solution was neutralized with 2N HCl extracted with ethyl acetate. The organic extracts were concentrated under reduced pressure. The concentrate was recrystallized from hexane-isopropyl ether to afford the title compound as colorless crystals.

m.p.: 94°–95° C.

Elemental Analysis for $C_{12}H_{14}N_2O_2 \cdot 1/10H_2O$: Calcd.: C, 65.50; H, 6.50; N, 12.73 Found: C, 65.51; H, 6.51; N, 12.5.

Reference Example 64
N-(4-t-butoxycarbonylphenyl)-N'-methoxycarbonyloxyguanidine In 120 ml of methanol was dissolved 8.72 g of 4-t-butoxycarbonylphenyl cyanamide produced in Reference Example 30 and 5.56 g of hydroxylamine hydrochloride. To the solution was added dropwise 8.80 g of triethylamine at −25° C. The reaction mixture was then warmed to room temperature and concentrated under reduced pressure. The concentrate was dissolved in ethyl acetate and washed with water. To the organic layer was added, at −10° C., 3.26 g of pyridine and 3.78 g of methyl chlorocarbonate. The reaction mixture was warmed to room temperature. Then, the reaction mixture was washed with water, and the organic layer was concentrated under reduced pressure to give a crude product. The crude product was recrystallized from isopropyl ether to afford 9.39 g of the title compound as colorless crystals.

m.p.: 122°–126° C.

Elemental Analysis for $C_{14}H_{19}N_3O_5$ Calcd.: C, 54.36; H, 6.19; N, 13.58 Found: C, 54.29; H, 6.02; N, 13.41.

Reference Example 65
N-(4-carboxyphenyl)-N'-methoxycarbonyloxyguanidine

In 25 ml of trifluoroacetic acid was dissolved 9.2 g of N-(4-t-butoxycarbonylphenyl)-N'-methoxycarbonyloxyguanidine produced in Reference Example 64. The solution was stirred for two hours at room temperature, then concentrated under reduced pressure, to which was added 100 mL of water was added to ther esidue and the pH of the solution was adjusted to 6 using sodium hydrogen carbonate. The resulting crystalline precipitate was collected by filtration and recrystallizated from tetrahydrofuran-ethyl acetate to afford 4.53 g of the title compound as a colorless crystalline product.

m.p.: 174°–175° C.

Elemental Analysis for $C_{10}H_{11}N_3O_5$ Calcd.: C, 47.43; H, 4.38; N, 16.59 Found: C, 47.17; H, 4.33; N, 16.44.

Reference Example 66
(S)-2-oxo-4-[4-(5-oxo-4,5-dihydro[1,2,4]oxadiazol-3-ylamino)benzoyl]aminoacetyl-3-[4-(5-oxo-4,5-dihydro[1,2,4]oxadiazol-3-ylamino)benzoyl]aminopropylpiperazine-1-acetic acid In 5 ml of trifluoroacetic acid was dissolved 500 mg of (S)-4-benzyloxycarbonylaminoacetyl-3-(3-t-butoxycarbonylaminopropyl)-2-oxopiperazine-1-acetic acid t-butyl ester. The solution was stirred for one hour at room temperature. The reaction mixture was concentrated under reduced pressure to leave an oily product, which was dissolved in 10 ml of methanol. To the solution was added 10 mg of 10% palladium-carbon. The mixture was stirred for one hour at room temperature under hydrogen atmosphere. The catalyst was filtered off, and the filtrate was concentrated under reduced pressure to leave a crude product of (S)-4-aminoacetyl-3-aminopropyl-2-oxopiperazine-1-acetic acid. This product was dissolved in a mixture of 10 ml of water and 10 ml of dioxane. To the solution was added 400 mg of sodium hydrogen carbonate. Subsequently, 420 mg of 3-(4-carboxyphenylamino)-1,2,4-oxadiazolin-4H-5-one produced in Reference Example 25 and 250 mg of N-hydroxysuccinimide were dissolved in 5 ml of dimethylformamide. To the solution was added 450 mg of dicyclohexyl carbodiimide. The mixture was stirred for 3 hours at room temperature, then concentrated under reduced pressure to leave an oily substance. This substance was dissolved in 5 ml of dioxane, and added to the solution of (S)-4-aminoacetyl-3-aminopropyl-2-oxopiperazine-1-acetic acid prepared as above. The mixture was stirred for 6 hours at room temperature. The reaction mixture was neutralized with 1N HCl, then concentrated under reduced pressure to give a crude product, followed by purification by means of a sephadex LH-20 column to afford 230 mg of the title compound as a colorless amorphous powdery product.

Specific optical rotation: $[\alpha]_D^{20}$ 51.9° (C=0.27, DMSO)
Elemental Analysis for $C_{29}H_{30}N_{10}O_{10} \cdot H_2O$: Calcd.: C, 50.00; H, 4.63; N, 20.11 Found: C, 49.79; H, 4.91; N, 19.96.

Reference Example 67
(S)-2-oxo-4-[4-(5-trifluoromethyl[1,2,4]-oxadiazol-3-ylamino)benzoyl]aminoacetyl-3-[4-(5-trifluoromethyl[1,2,4]-oxadiazol-3-ylamino)benzoyl]propylpiperazine-1-acetic acid Using (S)-4-benzyloxycarbonylaminoacetyl-3-(3-t-butoxycarbonylaminopropyl)-2-oxopiperazine-1-acetic acid t-butyl ester produced in Reference Example 2 and 3-(4-carboxyphenylamino)-5-trifluoromethyl-1,2,4-oxadiazole produced in Reference Example 61, the title compound was produced as a colorless amorphous powdery product by substantially the same procedure as in Reference Example 66.

Specific optical rotation: $[\alpha]_D^{20}$ 39.7° (C=0.25, DMSO)
Elemental Analysis for $C_{31}H_{28}N_{10}O_8F_6 \cdot H_2O$: Calcd.: C, 46.51; H, 3.78; N, 17.49 Found: C, 46.44; H, 3.97; N, 17.26.

Reference Example 68
(S)-4-[4-(N-methoxycarbonyloxyguanidino)benzoylaminoacetyl]-3-[3-(N-methoxycarbonyloxyguanidino)benzoylamino]propyl-2-oxopiperazine-1-acetic acid Employing (S)-4-benzyloxycarbonylaminoacetyl-3-(3-t-butoxycarbonylaminopropyl)-2-oxopiperazine-1-acetic acid t-butyl ester produced in Reference Example 2 and N-(4-carboxyphenyl)-N'-methoxycarbonyloxyguanidine produced in Reference Example 32, the title compound was produced as a colorless amorphous powdery product by substantially the same procedure as in Reference Example 66.

Specific optical rotation: $[\alpha]_D^{20}$ 20 31.20° (C=0.28, DMSO)
Elemental Analysis for $C_{31}H_{38}N_{10}O_{12} \cdot 2H_2O$: Calcd.: C, 47.81; H, 5.44; N, 17.99 Found: C, 47.63; H, 5.71; N, 17.83.

Reference Example 69
(S)-4-(N-t-butoxycarbonylamino)acetyl-3-(3-t-butoxycarbonylamino)propyl-2-oxopiperazine-1-acetic acid In 10 ml of trifluoroacetic acid was dissolved 1.5 g of (S)-4-benzyloxycarbonylaminoacetyl-3-(3-t-butoxycarbonylaminopropyl)-2-oxopiperazine-1-acetic acid t-butyl ester. The solution was stirred for one hour at room temperature. The reaction mixture was concentrated under reduced pressure to leave an oily substance, which was dissolved in a mixture of 10 ml of water and 10 ml of dioxane. To the solution was added 400 mg of sodium hydrogen carbonate and 700 mg of di-t-butyl dicarbonate. The mixture was stirred for 3 hours at room temperature. Dioxane was distilled off under reduced pressure to leave an aqueous solution, which was washed with ethyl acetate. The pH of the aqueous solution was adjusted to 3 with the addition of potassium hydrogen sulfate. The resulting aqueous solution was extracted with ethyl acetate. The extract solution was dried over anhydrous magnesium sulfate, and concentrated under reduced pressure to leave 1.2 g of the title compound as colorless crystals.

m.p.: 107°–109° C.
Elemental Analysis for $C_{21}H_{36}N_4O_8$ Calcd.: C, 53.38; H, 7.68; N, 11.86 Found: C, 53.35; H, 7.73; N, 11.95.

Reference Example 70
(S)-4-(N-benzyloxycarbonylamino)acetyl-3-(3-benzyloxycarbonylamino)propyl-2-oxopiperazine-1-acetic acid In 10 ml of trifluoroacetic acid was dissolved 2.0 g of (S)-4-benzyloxycarbonylaminoacetyl-3-(3-t-butoxycarbonylaminopropyl)-2-oxopiperazine-1-acetic acid t-butyl ester. The solution was stirred for one hour at room temperature. The reaction mixture was concentrated under reduced pressure to leave an oily substance, which was dissolved in a mixture of 10 ml of water and 10 ml of dioxane. To the solution was added 600 mg of sodium hydrogen carbonate and 550 mg of carbobenzoxy chloride. The mixture was stirred for one hour at room temperature. Dioxane was distilled off under reduced pressure to leave an aqueous solution, which was washed with ethyl acetate. The pH of the aqueous solution was adjusted to 3.5, using potassium hydrogencarbonate. The resulting aqueous solution was to extracted with ethyl acetate. The extract solution was dried over anhydrous magnesium sulfate, and concentrated under reduced pressure to afford 1.5 g of the title compound as a colorless amorphous powdery product.

Elemental Analysis for $C_{27}H_{32}N_4O_8$ Calcd.: C, 59.99; H, 5.97; N, 10.36 Found: C, 60.13; H, 5.87; N, 10.22.

Reference Example 71
(S)-4-(4-guanidinobenzoylamino)acetyl-3-[3-(4-guanidinobenzoylamino)]propyl-2-oxopiperazine-1-acetic acid pivaloyloxymethyl ester dihydrochloride In 5 ml of dimethylformamide was dissolved 500 mg of (S)-4-(N-benzyloxycarbonylamino)acetyl-3-(3-benzyloxycarbonylamino)propyl-2-oxopiperazine-1-acetic acid produced in Reference Example 70, 128 mg of potassium carbonate and 463 mg of potassium iodide. To the solution was added, at room temperature, 420 mg of pivaloyloxy methyl chloride. The mixture was stirred for 12 hours at room temperature. The reaction mixture was concentrated under reduced pressure to leave an oily substance, which was dissolved in ethyl acetate. The solution was washed with a 10% aqueous solution of potassium hydrogen sulfate and a saturated aqueous solution of sodium hydrogen carbonate, followed by concentration under reduced pressure. The concentrate was dissolved in 10 ml of methanol, to which was added 100 mg of 10% palladium-carbon. The mixture was stirred for one hour under a hydrogen atmosphere. The catalyst was filtered off, and the filtrate was concentrated to leave an oily substance. The oily substance was dissolved in a mixture of 20 ml each of water and dioxane. To the solution was added 400 mg of sodium hydrogen carbonate and 750 mg of 4-guanidinobenzoic acid 3,5-dioxo-4-azatricyclo[5,2,1,0,2,6]deca-8-en-4-ylester hydrochloride. The mixture was stirred for 3 hours at room temperature. Dioxane was distilled off under reduced pressure to leave an aqueous solution, to which was added hydrochloric acid to adjust the pH to 5. The resulting aqueous solution was subjected to CHP-20 column chromatography to afford 240 mg of the title compound as a colorless amorphous powdery product.

Specific optical rotation: $[\alpha]_D^{20}$ 56.23° (C=0.27, $H_2O$)

Elemental Analysis for $C_{33}H_{44}N_{10}O_8 \cdot 2HCl\ H_2O$: Calcd.: C, 49.56; H, 6.05; N, 17.51 Found: C, 49.31; H, 6.33; N, 17.24.

Reference Example 72

(S)-4-(4-guanidinobenzoylamino)acetyl-3-[3-(4-guanidinobenzoylamino)]propyl-2-oxopiperazine-1-acetic acid 1-(cyclohexyloxycarbonyloxy)ethyl ester dihydrochloride Employing (S)-4-(N-benzyloxycarbonylamino)acetyl-3-(3-benzyloxycarbonylamino)propyl-2-oxopiperazine-1-acetic acid produced in Reference Example 70 and 1-(cyclohexyloxycarbonyloxy)ethyl chloride, the title compound was produced as a colorless amorphous powdery product by substantially the same procedure as in Reference Example 71.

Specific optical rotation: $[\alpha]_D^{20}$ 52.5° (C=0.50, $H_2O$)

Elemental Analysis for $C_{36}H_{48}N_{10}O_9 \cdot 2HCl \cdot 3H_2O$: Calcd.: C, 48.49; H, 6.33; N, 15.71 Found: C, 48.35; H, 6.33; N, 15.52.

Reference Example 73

(S)-4-(4-guanidinobenzoylamino)acetyl-3-[3-(4-guanidinobenzoylamino)]propyl-2-oxopiperazine-1-acetic acid 5-methyl-2-oxo-1,3-dioxolen-4-ylmethyl ester dihydrochloride In 5 ml of dimethylformamide was dissolved 300 mg of (S)-4-(N-t-butoxycarbonylamino)acetyl-3-(3-t-butoxycarbonylamino)propyl-2-oxopiperazine-1-acetic acid produced in Reference Example 69 and 62 mg of sodium hydrogencarbonate. To the solution was added 115 mg of 5-methyl-2-oxo-1,3-dioxolen-4-ylmethyl bromide, and the mixture was stirred for 5 hours at room temperature. The reaction mixture was concentrated under reduced pressure to leave an oily substance, which was dissolved in ethyl acetate. The solution was washed with a 10% aqueous solution of sodium hydrogen carbonate and a saturated aqueous solution of sodium hydrogen carbonate, followed by concentration under reduced pressure. The concentrate was dissolved in 5 ml of trifluoroacetic acid and stirred for one hour at room temperature, followed by concentration under reduced pressure to leave an oily substance. The oily substance was dissolved in 20 ml each of water and dioxane, to which was added 400 mg of sodium hydrogen carbonate and 500 mg of 4-guanidinobenzoic acid 3,5-dioxo-4-azatricyclo[5,2,2,0,2,6]deca-8-en-4-yl ester hydrochloride.

The mixture was stirred for 3 hours at room temperature. Dioxane was distilled off under reduced pressure to leave an aqueous solution, to which was added 1N HCl to adjust the pH to 3.5. The resulting aqueous solution was subjected to CHP-20 column chromatography to afford 115 mg of the title compound as a colorless amorphous powdery product.

Specific optical rotation: $[\alpha]_D^{20}$ 43.7° (C=1.0, MeOH)

Elemental Analysis for $C_{32}H_{38}N_{10}O_9 \cdot 2HCl \cdot 3H_2O$: Calcd.: C, 46.10; H, 5.56; N, 16.80 Found: C, 46.43; H, 5.41; N, 16.58.

Reference Example 74

(S)-4-(4-guanidinobenzoylamino)acetyl-3-[3-(4-guanidinobenzoylamino)]propyl-2-oxopiperazine-1-acetic acid 2-(isobutyloxycarbonyl)-2-propylidene ethyl ester di-trifluoroacetate Employing (S)-4-(N-t-butoxycarbonylamino)acetyl-3-(3-t-butoxycarbonylamino)propyl-2-oxopiperazine-1-acetic acid produced in Reference Example 33 and 2-(isobutyloxycarbonyl)-2-propylidene ethyl bromide, the title compound was produced as a colorless amorphous powdery product by substantially the same procedure as in Reference Example 73.

Specific optical rotation: $[\alpha]_D^{20}$ 47.34° (C=0.48, $H_2O$)

Elemental Analysis for $C_{37}H_{50}N_{10}O_8 \cdot 2CF_3CO_2H \cdot 2H_2O$: Calcd.: C, 47.95; H, 5.50; N, 13.64 Found: C, 48.05; H, 5.51; N, 13.54.

Reference Example 75

(S)-4-(4-guanidinobenzoylamino)acetyl-3-[3-(4-guanidinobenzoylamino)]propyl-2-oxopiperazine-1-acetic acid ethyl ester dihydrochloride Employing (S)-4-(N-t-butoxycarbonylamino)acetyl-3-(3-t-butoxycarbonylamino)propyl-2-oxopiperazine-1-acetic acid produced in Reference Example 69 and ethyl iodide, the title compound was produced as a colorless amorphous powdery product by substantially the same procedure as in Reference Example 73.

Specific optical rotation: $[\alpha]_D^{20}$ 49.30° (C=0.47, $H_2O$)

Elemental Analysis for $C_{29}H_{38}N_{10}O_6 \cdot 2HCl \cdot 2H_2O$: Calcd.: C, 47.61; H, 6.06; N, 19.14 Found: C, 47.29; H, 6.35; N, 18.88.

Reference Example 76

(S,S)-[4-[2-benzyloxycarbonylamino-3-(4-methoxyphenyl) propionyl]-3-(3-tert-butoxycarbonylaminopropyl)-2-oxopiperazin-1-yl]acetic acid tert-butyl ester (another name: (S,S)-4-[2-benzyloxycarbonylamino-3-(4-methoxyphenyl) propionyl]-3-(3-tert-butoxycarbonylaminopropyl)-2-oxopiperazine-1-acetic acid tert-butyl ester)

In 50 ml of water was dissolved 4.2 g of (S)-[3-(3-tert-butoxycarbonylamino)propyl-2-oxopiperazin-1-yl]acetic acid tert-butyl ester-oxalate (another name: (S)-3-(3-tert-butoxycarbonylamino)propyl-2-oxopiperazine-1-acetic acid tert-butyl ester-oxalate) produced in Reference Example 3. To the solution was added 2.3 g of $NaHCO_3$. The resulting mixture was subjected to extraction twice with 50 ml each portion of dichloromethane. The extract solution was dried ($Na_2SO_4$), and concentrated under reduced pressure. To the concentrate was added 3 g of Z-Tyr(OMe)-OH, which was dissolved in 150 ml of dichloromethane. To the solution was added 1.92 g of WSC, which was stirred for two hours at room temperature. Dichloromethane was distilled off under reduced pressure, and the residue was subjected to extraction with ethyl acetate. The ethyl acetate layer was washed with a 3% aqueous solution of $KHSO_4$ and a saturated aqueous solution of $NaHCO_3$, which was dried ($Na_2SO_4$), followed by concentration under reduced pressure. The concentrate was purified by means of a silica gel chromatography (Hexane/AcOEt=1:2-AcOEt) to give 5.88 g of the title compound.

$^1$H-NMR(CDCl$_3$) δ: 1.35–2.10(4H,m), 1.41(9H,s), 1.46 (9H,s), 2.30(1H,m), 2.80–3.85(7H,m), 3.41(1H,d,J=17.4 Hz), 3.78(3H,s), 4.24(1H,d,J=17.4 Hz), 4.75(2H,m), 4.94 (1H,t,J=6.5 Hz), 5.10(2H,q,J=12.4 Hz), 5.69(1H,d,J=8.2 Hz), 6.80(2H,d,J=8.6 Hz), 7.09(2H,d,J=8.6 Hz), 7.35(5H,s).

Reference Example 77

(S,S)-[3-(3-aminopropyl)-4-[2-benzyloxycarbonylamino-3-(4-methoxyphenyl)propionyl]-2-oxopiperazin-1-yl]]acetic acid (another name: (S,S)-3-(3-aminopropyl)-4-[2-benzyloxycarbonylamino-3-(4-methoxyphenyl)propionyl-2-oxopiperazine-1-acetic acid)

In 20 ml of toluene was suspended 5.7 g of (S,S)-[4-[2-benzyloxycarbonylamino-3-(4-methoxyphenyl)propionyl]-3-(3-tert-butoxycarbonylaminopropyl)-2-oxopiperazin-1-yl]acetic acid tert-butyl ester (another name: (S,S)-4-[2-benzyloxycarbonylamino-3-(4-methoxyphenyl)propionyl]-3-(3-tert-butoxycarbonylaminopropyl)-2-oxopiperazine-1-acetic acid tert-butyl ester) produced in Reference Example 76. The suspension was stirred at 0° C. (ice bath) to which was added 20 ml of trifluoroacetic acid. The mixture was stirred for two hours at room temperature, followed by addition of toluene and concentration under reduced pressure. The concentrate was dissolved in 30 ml of water. The pH of the aqueous solution was adjusted to 5 with conc. aqueous ammonia, and the resulting solution was subjected to XAD-2 column chromatography (eluting with H$_2$O→50% CH$_3$CN water) to afford 4.3 g of the title compound.

$^1$H-NMR(CD$_3$OD) δ: 1.40–2.10(4H,m), 2.32(1H,m), 2.80–4.00(7H,m), 3.16(1H,d,J=16.5 Hz), 3.77(3H,s), 4.61–4.85(2H,m), 4.72(1H,d,J=16.5 Hz), 5.05(2H,q,J=12.3 Hz), 6.82(2H,d,J=8.4 Hz), 7.11(2H,d,J=8.4 Hz), 7.32(5H,s).

Reference Example 78

(S,S)-[4-[2-benzyloxycarbonylamino-3-(4-methoxyphenyl) propionyl]-3-(3-benzyloxycarbonylaminopropyl)-2-oxopiperazin-1-yl]acetic acid (another name: (S,S)-4-[2-benzyloxycarbonylamino-3-(4-methoxyphenyl)propionyl]-3-(3-benzyloxycarbonylaminopropyl)-2-oxopiperazine-1-acetic acid)

In 100 ml of a 50% aqueous solution of dioxane was dissolved 3.8 g of (S,S)-[3-(3-aminopropyl)-4-[2-benzyloxycarbonylamino-3-(4-methoxyphenyl)propionyl]-2-oxopiperazin-1-yl]acetic acid (another name: (S,S)-3-(3-aminopropyl)-4-[2-benzyloxycarbonylamino-3-(4-methoxyphenyl) propionyl]-2-oxopiperazine-1-acetic acid) produced in Reference Example 77. To the solution was added 1.52 g of NaHCO$_3$, to which was added dropwise, at 0° C. (ice bath) 1.24 ml of benzyloxycarbonyl-chloride. The mixture was stirred for 1.5 hour at room temperature. Dioxane was distilled off. To the residue was added a 3% aqueous solution of KHSO$_4$ to adjust the pH to 2. The mixture was subjected to extraction with ethyl acetate. The extract solution was washed with a saturated aqueous solution of NaHCO$_3$, dried (Na$_2$SO$_4$), and concentrated under reduced pressure. To the concentrate was added ether. The mixture was subjected to decantation twice to afford 4 g of the title compound.

$^1$H-NMR(CDCl$_3$) δ: 1.40–2.05(4H,m), 2.22(1H,m), 2.75 (9H,m), 3.74(3H,s), 4.65–5.20(6H,m), 5.52(1H,t,J=5.5 Hz), 5.94(1H,d,J=8.6 Hz), 6.78(2H,d,J=8.6 Hz), 7.05(2H,d,J=8.6 Hz), 7.31(10H,s).

Reference Example 79

(S,S)-[4-[2-benzyloxycarbonylamino-3-(4-methoxyphenyl) propionyl]-3-(3-benzyloxycarbonylaminopropyl)-2-oxopiperazin-1-yl]acetic acid tert-butyl ester (another name: (S,S)-4-[2-benzyloxycarbonylamino-3-(4-methoxyphenyl) propionyl]-3-(3-benzyloxycarbonylaminopropyl)-2-oxopiperazine-1-acetic acid tert-butyl ester)

In 50 ml of dichloromethane was dissolved 1.7 g of (S,S)-[4-[2-benzyloxycarbonylamino-3-(4-methoxyphenyl) propionyl]-3-(3-benzyloxycarbonylaminopropyl)-2-oxopiperazin-1-yl]acetic acid (another name: (S,S)-4-[2-benzyloxycarbonylamino- 3-(4-methoxyphenyl)propionyl]-3-(3-benzyloxycarbonylaminopropyl)-2-oxopiperazine-1-acetic acid) produced in Reference Example 78, 2 ml of tert-butanol and 1.6 g of 4-dimethylaminopyridine. To the solution was then added 0.6 g of WSC, and the mixture was stirred for 24 hours at room temperature. Dichloromethane was distilled off, and the residue was subjected to extraction with ethyl acetate. The ethyl acetate layer was washed with water and a saturated aqueous saline solution, dried (Na$_2$SO$_4$), concentrated under reduced pressure. The concentrate was purified by means of a silica gel column chromatography (AcOEt), followed by crystallization from ether/hexane to afford 1.02 g of the title compound as colorless crystals.

m.p.: 138°–140° C.

Specific optical rotation: $[α]_D^{20}$ +49.7° (C=0.431, MeOH)

Elemental Analysis for C$_{39}$H$_{48}$N$_4$O$_9$(716.832): Calcd.: C, 65.35; H, 6.75; N, 7.82 Found: C, 65.17; H, 6.69; N, 7.91.

Reference Example 80

(S,S)-[4-[2-benzyloxycarbonylamino-3-(4-methoxyphenyl) propionyl]-3-[3-(4-guanidinobenzoylamino)propyl]-2-oxopiperazin-1-yl]acetic acid hydrochloride (another name: (S,S)-4-[2-benzyloxycarbonylamino-3-(4-methoxyphenyl) propionyl]-3-[3-(4-guanidinobenzoylamino)propyl]-2-oxopiperazine-1-acetic acid hydrochloride)

In 50 ml of a 50% aqueous solution of dioxane was dissolved 0.5 g of (S,S)-[3-(3-aminopropyl)-4-[2-benzyloxycarbonylamino-3-(4-methoxyphenyl)propionyl]-2-oxopiperazin-1-yl]acetic acid (another name: (S,S)-3-(3-aminopropyl)-4-[2-benzyloxycarbonylamino-3-(4-methoxyphenyl)propionyl]-2-oxopiperazine-1-acetic acid) produced in Reference Example 78. To the solution was added 0.24 g of NaHCO$_3$, to which was then added 0.377 g of 4-guanidinobenzoic acid 3,5-dioxo-4-azatricyclo[5,2,1,0 2,6]deca-8-en-4-yl ester hydrochloride. The mixture was stirred for two hours at room temperature. The pH of the reaction mixture was adjusted to 3 with 1N-HCl, followed by distilling off dioxane. The residue was purified by means of column chromatography (eluting with H$_2$O→10% aqueous solution of CH$_3$CN→a 20% aqueous solution of CH$_3$CN→a 50% aqueous solution of CH$_3$CN) to afford 0.43 g of the title compound.

$^1$H-NMR(CD$_3$OD) δ: 1.50–2.10(4H,m), 2.45(1H,m), 2.80–4.25(9H,m), 3.77(3H,s), 4.60–5.00(2H,m), 5.00(2H,s), 6.83(2H,d,J=8.5 Hz), 7.13(2H,d,J=8.5 Hz), 7.30(5H,s), 7.35 (2H,d,J=8.5 Hz), 7.92(2H,d,J=8.5 Hz).

Reference Example 81

(S,S)-[3-[3-(4-guanidinobenzoylamino)propyl]-4-[3-(4-methoxyphenyl)-2-[4-(5-trifluoromethyl-[1,2,4]oxadiazol-3-ylamino)benzoylamino]propionyl]-2-oxopiperazin-1-yl] acetic acid hydrochloride (another name: (S,S)-3-[3-(4-guanidinobenzoylamino)-propyl]-4-[3-(4-methoxyphenyl)-2-[4-(5-trifluoromethyl-[1,2,4]oxadiazol-3-ylamino) benzoylamino]propionyl]-2-oxopiperazine-1-acetic acid hydrochloride)

In 40 ml of methanol was dissolved (S,S)-[4-[2-benzyloxycarbonylamino-3-(4-methoxyphenyl)propionyl]-

3-[3-(4-guanidinobenzoylamino)propyl]-2-oxopiperazin-1-yl]acetic acid hydrochloride (another name: (S,S)-4-[2-benzyloxycarbonylamino-3-(4-methoxyphenyl)propionyl]-3-[3-(4-guanidinobenzoylamino)propyl]-2-oxopiperazine-1-acetic acid hydrochloride) produced in Reference Example 80. To the solution was added 0.2 g of 10% Pd-C. The mixture was subjected to catalytic reduction for two hours at room temperature. The catalyst was filtered off, and the filtrate was concentrated under reduced pressure and dissolved in 50 ml of a 50% aqueous solution of dioxane. To the solution was added dropwise, while maintaining an alkaline pH, a dioxane solution of the acid chloride prepared from 4-(5-trifluoromethyl-[1,2,4]oxadiazol-3-ylamino) benzoic acid and oxazolyl chloride. The mixture was stirred for 30 minutes at room temperature. The pH of the reaction mixture was adjusted to 3 with 1N-HCl, then concentrated to dryness. The concentrate was purified by means of silica gel chromatography (AcOEt:AcOH:$H_2O$=8:1:1), and then triturated with ether to give 0.17 g of the title compound as a colorless powdery product.

Specific optical rotation: $[\alpha]_D^{20}$ +42.8° (C=0.94, DMSO)

Elemental Analysis for $C_{37}H_{39}N_{10}O_8F_3.HCl.0.1Et_2O$ (852.649): Calcd.: C, 52.68; H, 5.08; N, 16.43 Found: C, 52.62; H, 5.01; N, 16.58.

Reference Example 82

(S,S)-[4-[3-(4-methoxyphenyl)-2-[4-(5-trifluoromethyl[1,2,4]oxadiazol-3-ylamino)benzoylamino]propionyl]-2-oxo-3-[3-[4-(5-trifluoromethyl[1,2,4]oxadiazol-3-ylaminobenzoyl-amino]propyl]piperazin-1-yl]acetic acid tert-butyl ester (another name: (S,S)-4-[3-(4-methoxyphenyl)-2-[4-(5-trifluoromethyl[1,2,4]oxadiazol-3-ylamino)benzoylamino]propionyl]-2-oxo-3-[3-[4-(5-trifluoromethyl[1,2,4]oxadiazol-3-ylaminobenzoyl-amino]propyl]piperazine-1-acetic acid tert-butyl ester)

In 50 ml of methanol was dissolved 0.54 g of (S,S)-[4-[2-benzyloxycarbonylamino-3-(4-methoxyphenyl)propionyl]-3-(3-benzyloxycarbonylaminopropyl)-2-oxopiperazin-1-yl]acetic acid tert-butyl ester (another name: (S,S)-4-[2-benzyloxycarbonylamino-3-(4-methoxyphenyl)-propionyl]-3-(3-benzyloxycarbonylaminopropyl)-2-oxopiperazine-1-acetic acid tert-butyl ester) produced in Reference Example 79. To the solution was added 0.25 g of 10% Pd-C. The mixture was subjected to catalytic reduction for two hours. The catalyst was filtered off, and the filtrate was concentrated to dryness under reduced pressure. To the concentrate was added 0.41 g of 4(5-trifluoromethyl-[1,2,4] oxadiazol-3-ylamino)benzoic acid and 0.1 g of 4-dimethyl aminopyridine. The mixture was dissolved in 30 ml of acetonitrile. To the solution was added 0.39 g of WSC, and the mixture was stirred for 20 hours. Acetonitrile was distilled off, and the residue was subjected to extraction with ethyl acetate. The extract solution was washed with a 3% aqueous solution of $KHSO_4$ and a saturated aqueous solution of NaCl, dried ($Na_2SO_4$), and concentrated under reduced pressure. The concentrate was purified by means of silica gel chromatography (AcOEt) to afford 0.44 g of the title compound.

$^1$H NMR(CD$_3$OD) δ: 1.45(9H,s), 1.50–2.10(4H,m), 2.47 (1H,m), 2.95–4.20(9H,m), 3.77(3H,s), 4.80–5.20(2H,m), 6.86(2H,d,J=8.6 Hz), 7.20(2H,d,J=8.6 Hz), 7.41(2H,d,J=8.8 Hz), 7.42(2H,d,J=8.8 Hz), 7.72(2H,d,J=8.8 Hz), 7.77(2H,d, J=8.8 Hz).

Reference Example 83

(S,S)-[4-[3-(4-methoxyphenyl)-2-[4-(5-trifluoromethyl[1,2,4]oxadiazol-3-ylamino)benzoylamino]propionyl]-2-oxo-3-[3-(4-(5-trifluoromethyl[1,2,4]oxadiazol-3-ylaminobenzoyl-amino]propyl]piperazin-1-yl]acetic acid (another name: (S,S)-4-[3-(4-methoxyphenyl)-2-[4-(5-trifluoromethyl[1,2,4]oxadiazol-3-ylamino)benzoylamino]propionyl]-2-oxo-3-[3-[4-(5-trifluoromethyl[1,2,4]oxadiazol-3-ylaminobenzoyl-amino]propyl]piperazine-1-acetic acid)

In 6 ml of trifluoroacetic acid was dissolved, at 0° C., 0.44 g of (S,S)-[4-[3-(4-methoxyphenyl)-2-[4-(5-trifluoromethyl [1,2,4]oxadiazol- 3-ylamino)benzoylamino]propionyl]-2-oxo-3-[3-[4-(5-trifluoromethyl[1,2,4]oxadiazol-3-ylaminobenzoyl-amino]propyl]piperazin-1-yl]acetic acid tert-butyl ester (another name: (S,S)-4-[3-(4-methoxyphenyl)-2-[4-(5-trifluoromethyl[1,2,4]oxadiazol-3-ylamino)benzoylamino]propionyl]-2-oxo-3-[3-[4-(5-trifluoromethyl[1,2,4]oxadiazol-3-ylaminobenzoyl-amino] propyl]piperazine-1-acetic acid tert-butyl ester) produced in Reference Example 82. The solution was stirred for two hours at room temperature. The reaction mixture was added to toluene, which was twice concentrated to dryness under reduced pressure. The concentrate was triturated with in a small volume of ethyl acetate ether to give 0.38 g of the title compound as a powdery product.

Specific optical rotation: $[\alpha]_D^{20}$ +0.7° (C=1.043, DMSO)

Elemental Analysis for $C_{39}H_{36}N_{10}O_9F_6.2H_2O.0.2AcOEt$ (956.419): Calcd.: C, 49.08; H, 4.38; N, 14.64 Found: C, 50.17; H, 4.17; N, 14.35.

Reference Example 84

(S,S)-[4-[3-(4-methoxyphenyl)-2-[4-(5-oxo-4,5-dihydro[1,2,4]oxadiazol-3-ylamino)benzoylamino]propionyl]-2-oxo-3-[4-(5-oxo-4,5-dihydro[1,2,4]oxadiazol-3-ylamino) benzoylamino]-propyl]piperazin-1-yl]acetic acid tert-butyl ester (another name: (S,S)-4-[3-(4-methoxyphenyl)-2-[4-(5-oxo-4,5-dihydro[1,2,4]oxadiazol-3-ylamino)benzoylamino] propionyl]-2-oxo-3-[4-(5-oxo-4, 5-dihydro[1,2,4]oxadiazol-3-ylamino)benzoylamino]-propyl]piperazine-1-acetic acid tert-butyl ester)

In 50 ml of methanol was dissolved 0.54 g of (S,S)-[4-[2-benzyloxycarbonylamino-3-(4-methoxyphenyl) propionyl]-3-(3-benzyloxycarbonylaminopropyl)-2-oxopiperazin-1-yl)acetic acid tert-butyl ester (another name: (S,S)- 4-[2-benzyloxycarbonylamino-3-(4-methoxyphenyl)-propionyl]-3-(3-benzyloxycarbonylaminopropyl)-2-oxopiperazine-1-acetic acid tert-butyl ester) produced in Reference Example 79. To the solution was added 0.25 g of 10% Pd-C. The mixture was subjected to catalytic reduction for two hours. The catalyst was filtered off, and the filtrate was concentrated to dryness under reduced pressure. To the concentrate was added 0.33 g of 4-(5-oxo-4,5-dihydro[1,2,4]oxadiazol-3-ylamino)benzoic acid. The mixture was dissolved in 10 ml of N,N-dimethylformamide, and the solution was stirred at 0° C. N,N-dimethylformamide was distilled off under reduced pressure. To the residue was added water, and the pH of the aqueous solution was adjusted to 2 with a 3% aqueous solution of $KHSO_4$. The solution was subjected to extraction with ethyl acetate containing a small volume of N,N-dimethylformamide. The extract solution was washed with a saturated aqueous solution of NaCl, dried ($Na_2SO_4$), and concentrated under reduced pressure. The concentrate was purified by means of silica gel chromatography (AcOEt→AcOEt/AcOH/$H_2O$=8:1:1) to afford 0.52 g of the title compound.

$^1$H-NMR(CD$_3$OD) δ: 1.44(9H,s), 1.50–2.10(4H,m), 2.48 (1H,m), 2.90–4.20(9H,m), 3.75(3H,s), 4.80–5.20(2H,m), 6.84(2H,d,J=8.4 Hz), 7.18(2H,d,J=8.4 Hz), 7.33(2H,d,J=8.8 Hz), 7.35(2H,d,J=8.8 Hz), 7.71(2H,d,J=8.8 Hz), 7.74(2H,d, J=8.8 Hz).

Reference Example 85

(S,S)-[4-[3-(4-methoxyphenyl)-2-[4-(5-oxo-4,5-dihydro[1,2,4]oxadiazol-3-ylamino)benzoylamino]propionyl]-2-oxo- 3-[4-(5-oxo-4,5-dihydro[1,2,4]oxadiazol-3-ylamino) benzoylamino]-propyl]piperazin-1-yl]acetic acid (another name: (S,S)-4-[3-(4-methoxyphenyl)-2-[4-(5-oxo-4,5-dihydro[1,2,4]oxadiazol- 3-ylamino)benzoylamino] propionyl]-2-oxo-3-[4-(5-oxo-4,5-dihydro[1,2,4]oxadiazol-3-ylamino)benzoylamino]-propyl]piperazine-1-acetic acid)

In 6 ml of trifluoroacetic acid was dissolved, at 0° C., 0.62 g of (S,S)-[4-[3-(4-methoxyphenyl)-2-[4-(5-oxo-4,5-dihydro[1,2,4]oxadiazol-3-ylamino)benzoylamino] propionyl]-2-oxo-3-[4-(5-oxo-4,5-dihydro[1,2,4]oxadiazol-3-ylamino)benzoylamino]-propyl]piperazin-1-yl]acetic acid tert-butyl ester (another name: (S,S)-4-[3-(4-methoxyphenyl)-2-[4-(5-oxo-4,5-dihydro[1,2,4]oxadiazol-3-ylamino)benzoylamino]propionyl]-2-oxo-3-[4-(5-oxo-4,5-dihydro[1,2,4]oxadiazol-3-ylamino)benzoylamino]-propyl]piperazine-1-acetic acid tert-butyl ester) produced in Reference Example 84. The solution was stirred for two hours at room temperature. To the reaction mixture was added toluene. The mixture was twice concentrated to dryness under reduced pressure. The concentrate was dissolved in a small volume of methanol, to which was then added ethyl acetate to afford 0.43 g of the title compound as a powdery product.

Specific optical rotation: $[\alpha]_D^{20}$ +7.5° (C=0.983, DMSO)

Elemental Analysis for $C_{37}H_{38}N_{10}O_{11}.1.5H_2O.0.5AcOEt$ (869.846): Calcd.: C, 53.85; H, 5.21; N, 16.10 Found: C, 53.71; H, 5.05; N, 15.97.

Reference Example 86

(S,S)-[4-[2-[4-(3-methoxycarbonyloxyguanidino) benzoylamino-3-(4-methoxyphenyl)propionyl]-3-[3-[4-(3-methoxycarbonyloxyguanidino)benzoyl]amino]propyl-2-oxopiperazin-1-yl]acetic acid tert-butyl ester (another name: (S,S)-4-[2-[4-(3-methoxycarbonyloxyguanidino) benzoylamino-3-(4-methoxyphenyl)propionyl]-3-[3-[4-(3-methoxycarbonyloxyguanidino)benzoyl]amino]propyl-2-oxopiperazine-1-acetic acid tert-butyl ester)

In 50 ml of methanol was dissolved 0.5 g of (S,S)-[4-[2-benzyloxycarbonylamino-3-(4-methoxyphenyl-propionyl]-3-(3-benzyloxycarbonylaminopropyl)-2-oxopiperazin-1-yl] acetic acid tert-butyl ester (another name: (S,S)-4-[2-benzyloxycarbonylamino-3-(4-methoxyphenylpropionyl]-3-(3-benzyloxycarbonylaminopropyl)-2-oxopiperazine-1-acetic acid tert-butyl ester) produced in Reference Example 79. To the solution was added 0.25 g of 10% Pd-C, and the mixture was subjected to catalytic reduction for two hours. The catalyst was filtered off, and the filtrate was concentrated to dryness under reduced pressure. To the concentrate was added 0.38 g of 4-(3-methoxycarbonyloxyguanidino) benzoic acid. The mixture was dissolved in 10 ml of N,N-dimethylformamide. The solution was stirred at 0° C., to which was then added 0.21 ml of triethylamine. To the mixture was further added 0.25 g of diethyl cyanophosphate, followed by stirring for one hour at 0° C. To the reaction mixture was added 1 ml of acetic acid. The mixture was subjected to distillation under reduced pressure and the residue was purified by means of silica gel chromatography (AcOEt→AcOEt/AcOH/H₂O=18:1:1) to afford 0.51 g of the title compound.

$^1$H-NMR(CD₃OD) δ: 1.44(9H,s), 1.50–2.10(4H,m), 2.48 (1H,m), 2.90–4.20(9H,m), 3.76(3H,s), 3.84(6H,s), 4.80–5.20(2H,m), 6.84(2H,d,J=8.6 Hz), 7.18(2H,d,J=8.6 Hz), 7.33(4H,d,J=8.6 Hz), 7.67(4H,d,J=8.6 Hz).

Reference Example 87

(S,S)-[4-[2-[4-(3-methoxycarbonyloxyguanidino) benzoylamino-3-(4-methoxyphenyl)propionyl]-3-[3-[4-(3-methoxycarbonyloxyguanidino)benzoyl]amino]propyl-2-oxopiperazin-1-yl]acetic acid (another name: (S,S)-4-[2-[4-(3-methoxycarbonyloxyguanidino)benzoylamino-3-(4-methoxyphenyl)propionyl]-3-[3-[4-(3-methoxycarbonyloxyguanidino)benzoyl]amino]propyl-2-oxopiperazine-1-acetic acid)

In 6 ml of trifluoroacetic acid was dissolved, at 0° C., 0.51 g of (S,S)-[4-[2-[4-(3-methoxycarbonyloxyguanidino) benzoylamino-3-(4-methoxyphenyl)propionyl]-3-[3-[4-(3-methoxycarbonyloxyguanidino)benzoyl]amino]propyl-2-oxopiperazin-1-yl]acetic acid tert-butyl ester (another name: (S,S)-4-[2-[4-(3-methoxycarbonyloxyguanidino) benzoylamino-3-(4-methoxyphenyl)propionyl]-3-[3-[4-(3-methoxycarbonyloxyguanidino)benzoyl]amino]propyl-2-oxopiperazine-1-acetic acid tert-butyl ester) produced in Reference Example 86. The solution was stirred for two hours at room temperature. To the reaction mixture was added toluene, which was twice subjected to concentration to dryness under reduced pressure. The concentrate was dissolved in a 50% aqueous methanol and was purified by CHP-20 column chromatography (H₂O→20% aqueous methanol→50% aqueous methanol→75% aqueous methanol) to afford 0.2 g of the title compound as a powdery product.

Specific optical rotation: $[\alpha]_D^{20}$ +9.7° (C=1.04, DMSO)

Elemental Analysis for $C_{39}H_{46}N_{10}O_{13}.0.5H_2O$ (871.862): Calcd.: C, 53.73; H, 5.43; N, 16.07 Found: C, 53.76; H, 5.46; N, 16.09.

Reference Example 88

(S,S)-4-[2-(4-guanidinobenzoyl)amino-3-(4-methoxyphenyl)propionyl)-3-[3-(4-guanidinobenzoyl) aminopropyl]-2-oxopiperazine-1-acetic acid hydrochloride In 5 ml of methanol was dissolved 250 mg of (S,S)-3-(3-aminopropyl)-4-[2-benzyloxycarbonylamino-3-( 4-methoxyphenyl)propionyl]-2-oxopiperazine-1-acetic acid produced in Reference Example 77. To the solution was added 100 mg of 10% Pd-C, and the mixture was stirred for one hour at room temperature in a hydrogen atmosphere. The catalyst was filtered off, and the filtrate was concentrated under reduced pressure to leave an oily substance. The oily substance was dissolved in a mixture of 10 ml of dioxane and 10 ml of water. To the solution was added 210 mg of sodium hydrogencarbonate and 450 mg of 4-guanidinobenzoic acid 3,5-dioxo-4-azatricyclo[5,2,1,0 2,6]deca-8-en-4-ylester. The mixture was stirred for one hour at room temperature. The pH of the reaction mixture was adjusted to 3 with 1N HCl, then dioxane was distilled off under reduced pressure. The remaining aqueous solution was subjected to CHP-20 column chromatography. The fraction eluted with 10% acetonitrile/water was freeze-dried to afford 130 mg of the title compound as an amorphous powdery product.

Elemental Analysis for $C_{35}H_{42}N_{10}O_7.2H_2O$: Calcd.: C, 53.40; H, 6.02; N, 17.79 Found: C, 53.11; H, 5.86; N, 18.06.

Reference Example 89

(S)-[3-[3-(4-amidinobenzoylamino)propyl]-4-[[4-(iminomethoxycarbonylaminomethyl)benzoylamino]acetyl] -2-oxopiperazin-1-yl]acetic acid hydrochloride (another name: (S)-3-[3-(4-amidinobenzoylamino)propyl]-4-[[4-(iminomethoxycarbonylaminomethyl)benzoylamino]-acetyl]-2-oxopiperazine-1-acetic acid hydrochloride)

In a mixture of 1,4-dioxane (2.0 ml) and H₂O (2.0 ml) was dissolved (S)-[4-[(4-amidinobenzoylamino)acetyl]-3-[3-(4-amidinobenzoyl-amino)propyl]-2-oxopiperazin-1-yl]acetic acid hydrochloride (another name: (S)-4-[(4-amidinobenzoylamino)acetyl]-3-[3-(4-amidinobenzoyl-amino)propyl]-2-oxopiperazine-1-acetic acid hydrochloride) (0.17 g, 0.29 mmol) produced in Reference Example 4. To the solution was gradually added, at 0° C., a 2N aqueous solution of sodium hydroxide (0.46 ml, 0.91 mmol). To the mixture was then added gradually chlorocarbonic acid methyl ester (0.053 ml, 0.69 mmol), which was stirred for 30 minutes. The pH of the reaction mixture was adjusted to pH 3 with a 1N HCl, and ther eaction mixture was concentrated under reduced pressure. The concentrate was purified by means of column chromatography (CHP-20, $H_2O$-5% $CH_3CNaq$-10% $CH_3CNaq$-15% $CH_3CNaq$). The hydrochloride salt was prepared using 1N HCl to afford the title compound (0.20 g, 91%) as a colorless powdery product.

Specific optical rotation: $[\alpha]_D^{20}$ +49.7° (C=0.984, MeOH)

Elemental Analysis for $C_{29}H_{34}N_8O_8 \cdot 2.0HCl \cdot 2.5H_2O \cdot 1.0MeOH$ (772.640): Calcd.: C, 46.64; H, 5.87; N, 14.50 Found: C, 46.34; H, 5.62; N, 14.26.

Reference Example 90

(S,S)-[4-[2-[4-(3-methoxycarbonylguanidino) benzoylamino]-3-(4-methoxyphenyl)propionyl]-3-[3-[4-(3-methoxycarbonylguanidino)benzoylamino]propyl]-2-oxopiperazin-1-yl]acetic acid hydrochloride (another name: (S,S)-4-[2-[4-(3-methoxycarbonylguanidino) benzoylamino]-3-(4-methoxyphenyl)propionyl]-3-[3-[4-(3-methoxycarbonylguanidino)benzoylamino]propyl]-2-oxopiperazine-1-acetic acid hydrochloride)

In a mixture of 1,4-dioxane (5.2 ml) and $H_2O$ (5.2 ml) was dissolved (S,S)-[4-[2-(4-guanidinobenzoylamino)-3-(4-methoxyphenyl)propionyl]-3-[3-(4-guanidinobenzoylamino)propyl]-2-oxopiperazin-1-yl]acetic acid (another name: (S,S)-4-[2-(4-guanidinobenzoylamino)-3-(4-methoxyphenyl)propionyl]-3-[3-(4-guanidinobenzoylamino)propyl]-2-oxopiperazine- 1-acetic acid) (0.52 g, 0.73 mmol) produced in Reference Example 88. To the solution was added, at 0° C., 2N aqueous solution of sodium hydroxide (4.35 ml, 8.70 mmol) and chlorocarbonic acid methyl ester (0.55 ml, 7.25 mmol) while keeping the pH range of the reaction system at not higher than 10. The mixture was stirred for 30 minutes, whose pH was adjusted to 7 with 1N HCl, and the resulting mixture was concentrated under reduced pressure. The concentrate was dissolved in $H_2O$ (5.0 ml), to which was added, at 0° C., lithium hydroxide (0.20 g, 4.78 mmol). The mixture was stirred for two hours at 0° C., the pH was adjusted to 3, and concentrated under reduced pressure. The concentrate was purified by means of column chromatography [(CHP-20, 10% $CH_3CNaq$-15% $CH_3CNaq$-20% $CH_3CNaq$-25% $CH_3CNaq$) and (LH-20, $H_2O$)] to afford the title compound (0.28 g, 39%).

Specific optical rotation: $[\alpha]_D^{20}$ +64.4° (C=1.041, MeOH)

Elemental Analysis for $C_{39}H_{46}N_{10}O_{11} \cdot 2.0HCl \cdot 4.5H_2O$ (984.845): Calcd.: C, 47.56; H, 5.83; N, 14.22 Found: C, 47.40; H, 5.55; N, 14.33.

Reference Example 91

(S,S)-[4-[2-benzyloxycarbonylamino-3-(4-methoxyphenyl) propionyl]-3-(3-benzyloxycarbonylaminopropyl)-2-oxopiperazin-1-yl]acetic acid 1-cyclohexyloxycarbonyloxy ethyl ester (another name: (S,S)-4-[2-benzyloxycarbonylamino-3-(4-methoxyphenyl)propionyl]-3-(3-benzyloxycarbonylaminopropyl)-2-oxopiperazine-1-acetic acid 1-cyclohexyloxycarbonyloxy ethyl ester)

In DMF (5.8 ml) was dissolved (S,S)-[4-[2-benzyloxycarbonylamino-3-(4-methoxyphenyl)propionyl]-3-(3-benzyloxycarbonylaminopropyl)-2-oxopiperazin-1-yl] acetic acid (another name: (S,S)-4-[2-benzyloxycarbonylamino-3-(4-methoxyphenyl)propionyl]-3-(3-benzyloxycarbonylaminopropyl)-2-oxopiperazine-1-acetic acid) (0.58 g, 0.88 mmol) produced in Reference Example 78 and triethylamine (0.49 ml, 3.52 mmol). To the solution was added, while stirring at room temperature, carbonic acid 1-chloroethyl ester cyclohexyl ester (0.73 g, 3.52 mmol) and potassium iodide (0.58 g, 3.52 mmol). The mixture was stirred for 38 hours at room temperature, then poured into water. To the mixture was extracted with ethyl acetate. The organic layer was dried over anhydrous magnesium sulfate and concentrated under reduced pressure. The concentrate was purified by means of silica gel column chromatography (hexane/ethyl acetate=⅔) to afford the title compound (0.43 g, 59%) as a colorless amorphous powdery product.

IR ν max $cm^{-1}$: 3410, 2930, 1755, 1710, 1645, 1510, 1450, 1240, 1075 NMR($CD_3OD$) δ: 1.10–2.10(14H,m), 1.52(3H,d,J=5.4 Hz), 2.80–5.20(15H,m), 3.77(3H,s), 5.07 (2H,s), 5.09(2H,s), 5.64(1H,d,J=7.8 Hz), 6.67–6.87(2H,m), 7.08(2H,d,J=8.4 Hz), 7.33(10H,s).

Reference Example 92

(S,S)-[4-[2-(4-guanidinobenzoylamino)-3-(4-methoxyphenyl)propionyl]-3-[3-(4-guanidinobenzoylamino)propyl]-2-oxopiperazin-1-yl]acetic acid 1-cyclohexyloxycarbonyloxyethyl ester (another name: (S,S)-4-[2-(4-guanidinobenzoylamino)-3-(4-methoxyphenyl)propionyl]-3-[3-(4-guanidinobenzoylamino)propyl]-2-oxopiperazine-1-acetic acid 1-cyclohexyloxycarbonyloxyethyl ester)

In methanol (8.6 ml) was dissolved (S,S)-[4-[2-benzyloxycarbonylamino-3-(4-methoxyphenyl)propionyl]-3-(3-benzyloxycarbonylaminopropyl)-2-oxopiperazin-1-yl] acetic acid 1-cyclohexyloxycarbonyloxyethyl ester (another name: (S,S)-4-[2-benzyloxycarbonylamino-3-(4-methoxyphenyl)propionyl]-3-(3-benzyloxycarbonylaminopropyl)-2-oxopiperazine-1-acetic acid 1-cyclohexyloxycarbonyloxyethyl ester) (0.43 g, 0.52 mmol) produced in Reference Example 91 and acetic acid (0.062 ml, 1.09 mmol). To this solution was added 10% Pd-C (0.17 g), and the mixture was stirred for one hour under a hydrogen atmosphere. The catalyst was filtered off, and the filtrate was concentrated under reduced pressure. The concentrate was dissolved in a mixture of 1,4-dioxane (4.3 ml) and $H_2O$ (8.6 ml). To the solution was added, while stirring at room temperature, sodium hydrogen carbonate (0.22 g, 2.59 mmol) and 4-guanidinobenzoic acid N-hydroxy-5-norbornene-2,3-dicarboxyimide ester (0.43 g, 1.14 mmol). One hour later, the pH of the reaction mixture was adjusted to 3 with 1N HCl, then concentrated under reduced pressure. The concentrate was purified by means of column chromatography [(CHP-20, 10% $CH_3CNaq$-15% $CH_3CNaq$-20% $CH_3CNaq$) and (LH-20, $H_2O$)] to afford the title compound (0.073 g, 14%) as a colorless amorphous powdery product.

Specific optical rotation: $[\alpha]_D^{20}$ +63.4° (C=1.009, MeOH)

Elemental Analysis for $C_{44}H_{56}N_{10}O_{10} \cdot 2.0HCl \cdot 3.0H_2O$ (1011.957): Calcd.: C, 52.22; H, 6.37; N, 13.84 Found: C, 52.38; H, 6.07; N, 13.81.

Reference Example 93

(S,S)-[3-(3-t-butoxycarbonylaminopropyl)-4-[2-(4-(1,3-dimethoxycarbonylguanidino)benzoylamino]-3-(4-methoxyphenyl)propionyl]-2-oxopiperazin-1-yl]acetic acid t-butyl ester (another name: (S,S)-3-(3-t- butoxycarbonylaminopropyl)-4-[2-[4-(1,3-dimethoxycarbonylguanidino)benzoylamino]-3-(4-methoxyphenyl)propionyl]-2-oxopiperazine-1-acetic acid t-butyl ester)

In methanol (6.6 ml) was dissolved (S,S)-(4-[2-benzyloxycarbonylamino-3-(4-methoxyphenyl)propionyl]-3-(3-t-butoxycarbonylaminopropyl)-2-oxopiperazin-1-yl] acetic acid t-butyl ester (another name: (S,S)-4-[2-benzyloxycarbonylamino-3-(4-methoxyphenyl)propionyl]-3-(3-t-butoxycarbonylaminopropyl)-2-oxopiperazine-1-acetic acid t-butyl ester) (0.66 g, 0.97 mmol) produced in Reference Example 9. To the solution was added 10% Pd-C (0.26 g), and the mixture was stirred for one hour under a hydrogen atmosphere. The catalyst was filtered off, and the filtrate was concentrated under reduced pressure. The concentrate was dissolved in a mixture of 1,4-dioxane (6.6 ml) and $H_2O$ (6.6 ml). To the solution was added, at room temperature, 4-guanidinobenzoic acid N-hydroxy-5-norbornene-2,3-dicarboximide ester (0.55 g, 1.45 mmol) and sodium hydrogen carbonate (0.12 g, 1.45 mmol). One hour later, the pH of the reaction system was adjusted with 1N HCl, and the reaction mixture was concentrated under reduced pressure. The concentrate was purified by means of column chromatography (CHP-20, $H_2O$-5% $CH_3CNaq$-10% $CH_3CNaq$-15% $CH_3CNaq$-25% $CH_3CNaq$-30% $CH_3CNaq$) to afford (S,S)-[3-(3-t-butoxycarbonylaminopropyl)-4-[2-(4-guanidinobenzoylamino)-3-(4-methoxyphenyl) propionyl]-2-oxopiperazin-1-yl]acetic acid t-butyl ester (another name: (S,S)-3-(3-t-butoxycarbonylaminopropyl)-4-[2-(4-guanidinobenzoylamino)-3-(4-methoxyphenyl) propionyl]-2-oxopiperazine-1-acetic acid t-butyl ester) (0.50 g, 73%) as a colorless amorphous powdery product. This product was dissolved in 1,4-dioxane (5.0 ml), to which was added, while stirring at 0° C. and keeping the pH of the reaction system at 10 or below, 2N NaOH (2.46 ml, 4.93 mmol) and chlorocarbonic acid methyl ester (0.27 ml, 3.52 mmol). The mixture was stirred for 30 minutes at 0° C., the pH was adjusted to 3 with 1N HCl, and the resulting mixture was extracted with ethyl acetate. The organic layer was dried over anhydrous magnesium sulfate and concentrated under reduced pressure. The concentrate was purified by means of silica gel column chromatography (hexane/ethyl acetate=1/10) to afford the title compound (0.42 g, 72%) as a colorless amorphous powdery product.

IR ν max $cm^{-1}$ (KBr): 3400, 2970, 1730, 1640, 1510, 1490, 1435, 1362, 1245, 1155, 1025, 948 NMR($CD_3OD$) δ: 1.39(9H,s), 1.46(9H,s), 1.20–1.65(2H,m), 1.65–2.06(2H,m), 2.41–2.64(1H,m), 2.88–4.18(7H,m), 3.46(2H,s), 3.59(1H,d, J=17.2 Hz), 3.72(3H,s), 3.77(3H,s), 4.08(1H,d,J=17.2 Hz), 4.78–4.97(1H,m), 5.11(1H,dd,J=6.2,9.2 Hz), 6.85(2H,d,J= 8.4 Hz), 7.19(2H,d,J=8.4 Hz), 7.30(2H,d,J=8.4 Hz), 7.84 (2H,d,J=8.4 Hz).

Reference Example 94

(S,S)-[3-(3-t-butoxycarbonylaminopropyl)-4-[2-[4-(3-methoxycarbonylguanidino)benzoylamino]-3-(4-methoxyphenyl)propionyl]-2-oxopiperazin-1-yl]acetic acid t-butyl ester (another name: (S,S)-3-(3-t-butoxycarbonylaminopropyl)-4-[2-[4-(3-methoxycarbonylguanidino)benzoylamino]-3-(4-methoxyphenyl)propionyl]-2-oxopiperazine-1-acetic acid t-butyl ester)

In a mixture of methanol (4.1 ml) and $H_2O$ (0.41 ml) was dissolved (S,S)-[3-(3-t-butoxycarbonylaminopropyl)-4-[2-[4-(1,3-dimethoxycarbonylguanidino)benzoylamino]-3-(4-methoxyphenyl)propionyl]-2-oxopiperazin-1-yl]acetic acid t-butyl ester (another name: (S,S)-3-(3-t-butoxycarbonylaminopropyl)-4-[2-[4-(1,3-dimethoxycarbonylguanidino)benzoylamino]-3-(4-methoxyphenyl)-propionyl]-2-oxopiperazine-1-acetic acid t-butyl ester) (0.41 g, 0.50 mmol) produced in Reference Example 93. To the solution was added, at 0° C., lithium hydroxide.1.0 hydrate (22.9 mg, 0.55 mmol). The mixture was stirred for 30 minutes at 0° C. then the pH was adjusted to 4 with 1N HCl. The reaction mixture was concentrated under reduced pressure. The concentrate was purified by means of silica gel column chromatography (ethyl acetate/methanol=10/1) to afford the title compound (0.36 g, 95%) as a colorless amorphous powdery product.

IR ν max $cm^{-1}$ (KBr): 3400, 2970, 1733, 1640, 1508, 1435, 1360, 1240, 1150 NMR($CD_3OD$) δ: 1.39(9H,s), 1.46 (9H,s), 1.20–2.05(4H,m), 2.42–2.64(1H,m), 2.84–4.20(9H, m), 3.68(3H,s), 3.77(3 H,s), 4.80–5.00(1H,m), 5.10(1H,dd, J=9.0,6.4 Hz), 6.84(2H,d,J=8.8 Hz), 7.18(2H,d,J=8.8 Hz), 7.45(2H,d,J=8.8 Hz), 7.82(2H,d,J=8.8 Hz).

Reference Example 95

(S,S)-[3-[3-(4-guanidinobenzoylamino)propyl]-4-[2-[4-(3-methoxycarbonylguanidino)benzoylamino]-3-(4-methoxyphenyl)propionyl]-2-oxopiperazin-1-yl]acetic acid hydrochloride (another name: (S,S)-3-[3-(4-guanidinobenzoylamino)propyl]-4-[2-[4-(3-methoxycarbonylguanidino)benzoylamino]-3-(4-methoxyphenyl)propionyl]-2-oxopiperazine-1-acetic acid hydrochloride)

In methylene chloride (2.0 ml) was dissolved (S,S)-[3-(3-t-butoxycarbonylaminopropyl)-4-[2-[4-(3-methoxycarbonylguanidino)benzoylamino]-3-(4-methoxyphenyl)propionyl]-2-oxopiperazin-1-yl]acetic acid t-butyl ester (another name: (S,S)-3-(3-t-butoxycarbonylaminopropyl)-4-[2-[4-(3-methoxycarbonylguanidino)benzoylamino]-3-(4-methoxyphenyl)propionyl]-2-oxopiperazine-1-acetic acid t-butyl ester) (0.35 g, 0.46 mmol) produced in Reference Example 94. To the solution was added, while stirring at room temperature, trifluoroacetic acid (2.0 ml). Two hours later, the reaction mixture was concentrated under reduced pressure. The concentrate was dissolved in a mixture of 1,4-dioxane (3.5 ml) and $H_2O$ (7.0 ml). To this solution was added, at room temperature, 4-guanidinobenzoic acid N-hydroxy-5-norbornene-2,3-dicarboximide ester (0.19 g, 0.50 mmol) and sodium hydrogen carbonate (0.19 g, 2.28 mmol). One hour later, the pH of the reaction system was adjusted to 2 with a 1N aqueous solution of hydrochloric acid. The reaction mixture was concentrated under reduced pressure. The concentrate was purified by means of column chromatography (CHP-20, $H_2O$-5% $CH_3CNaq$-10% $CH_3CNaq$-15% $CH_3CNaq$-20% $CH_3CNaq$-25% $CH_3CNaq$), which was processed with a 1N aqueous solution of hydrochloric acid to lead to the corresponding hydrochloride, i.e. the title compound (0.29 g, 69%) as a colorless amorphous powdery product.

Specific optical rotation: $[\alpha]_D^{20}$ +69.9° (C=1.025, MeOH)

Elemental Analysis for $C_{37}H_{44}N_{10}O_9 \cdot 2.0HCl \cdot 4.0H_2O$ (917.801): Calcd.: C, 48.42; H, 5.93; N, 15.26 Found: C, 48.30; H, 5.78; N, 15.20.

Reference Example 96

(S)-[4-[[4-(3-methoxycarbonylguanidino)-benzoylamino] acetyl]-3-[3-[4-(3-methoxycarbonylguanidino) benzoylamino]propyl]-2-oxopiperazin-1-yl]acetic acid hydrochloride (another name: (S)-4-[[4-(3-methoxycarbonylguanidino)benzoylamino]acetyl]-3-[3-[4-(3-methoxycarbonylguanidino)benzoylamino]propyl]-2-oxopiperazine-1-acetic acid hydrochloride)

In a mixture of 1,4-dioxane (3.0 ml) and H₂O.(3.0 ml) was dissolved (S)-[4-[(4-guanidinobenzoylamino)acetyl]-3-[3-(4-guanidinobenzoylamino)propyl]-2-oxopiperazin-1-yl] acetic acid hydrochloride (another name: (S)-4-[(4-guanidinobenzoylamino)acetyl]-3-[3-(4-guanidinobenzoylamino)propyl]-2-oxopiperazine-1-acetic acid hydrochloride) (0.3 g, 0.51 mmol) produced in Reference Example 26. To the solution was added gradually, with stirring at 0° C. while keeping the pH at 10 or below, a 2N aqueous solution of sodium hydroxide (2.60 ml, 5.10 mmol) and chlorocarbonic acid methyl ester (0.31 ml, 4.00 mmol). The reaction mixture was stirred for 10 minutes at 0° C., the pH was adjusted to 4 with a 1N aqueous solution of hydrochloric acid, and the resulting mixture was extracted with ethyl acetate. The organic layer was dried over anhydrous magnesium sulfate and concentrated under reduced pressure. The concentrate was purified by means of column chromatography (CHP-20, 10% CH₃CNaq-15% CH₃CNaq-20% CH₃CNaq-25% CH₃CNaq-35% CH₃CNaq) to give (S)-[4-[[4-(1,3-dimethoxycarbonylguanidino)benzoylamino]acetyl]-3-[3-[4-(1,3-dimethoxycarbonylguanidino)benzoylamino]-propyl]-2-oxopiperazin-1-yl]acetic acid (another name:

(S)-4-[[4-(1,3-dimethoxycarbonylguanidino)benzoylamino]acetyl]-3-[3-[4-(1,3-dimethoxycarbonylguanidino)benzoylamino]-propyl]-2-oxopiperazine-1-acetic acid) (0.26 g, 62%) as a colorless amorphous powdery product. This product (0.26 g, 0.31 mmol) was dissolved in a mixture of methanol (2.6 ml) and H₂O (0.26 ml). To the solution was added, at 0° C., lithium hydroxide.1.0hydrate (42 mg, 1.00 mmol). One hour later, the pH of the reaction mixture was adjusted to pH 4 with a 1N aqueous solution of hydrochloric acid, and the resulting mixture was concentrated under reduced pressure. The concentrate was purified by means of column chromatography [(CHP-20, 5% CH₃CNaq-10% CH₃CNaq-15% CH₃CNaq-20% CH₃CNaq) and (LH-20, H₂O)] to afford the title compound (0.13 g, 58%) as a colorless amorphous powdery product.

Specific optical rotation: $[\alpha]_D^{20}$ +48.2° (C=1.043, MeOH)

Elemental Analysis for $C_{31}H_{38}N_{10}O_{10}$·1.0HCl.3.0H₂O (801.211): Calcd.: C, 46.47; H, 5.66; N, 17.48 Found: C, 46.30; H, 5.38; N, 17.35.

Reference Example 97

(S)-[3-(3-t-butoxycarbonylaminopropyl)-4-[(4-guanidinobenzoylamino)acetyl]-2-oxopiperazin-1-yl]acetic acid t-butyl ester (another name: (S)-3-(3-t-butoxycarbonylaminopropyl)-4-[(4-guanidinobenzoylamino)acetyl]-2-oxopiperazine-1-acetic acid t-butyl ester)

In ethyl acetate (7.0 ml) was dissolved (S)-[4-benzyloxycarbonylaminoacetyl-3-(3-t-butoxycarbonylaminopropyl)-2-oxopiperazin-1-yl]acetic acid t-butyl ester (another name: (S)-4-benzyloxycarbonylaminoacetyl-3-(3-t-butoxycarbonyl-aminopropyl)-2-oxopiperazine-1-acetic acid t-butyl ester) (0.70 g, 1.24 mmol) produced in Reference Example 2. To the solution was added 10% Pd-C (0.21 g), which was stirred for one hour at room temperature under a hydrogen atmosphere. The catalyst was filtered off, and the filtrate was concentrated under reduced pressure. The concentrate was dissolved in a mixture of 1,4-dioxane (7.0 ml) and H₂O (7.0 ml). To the solution was added, at room temperature, 4-guanidinobenzoic acid N-hydroxy-5-norbornene-2,3-dicarboximide ester (0.56 g, 1.49 mmol). One hour later, the pH of the reaction mixture was adjusted to pH 4 with a 1N aqueous solution of hydrochloric acid, and the resulting mixture was concentrated under reduced pressure. The concentrate was purified by means of column chromatography (CHP-20, H₂O-5% CH₃CNaq-10% CH₃CNaq-15% CH₃CNaq-20% CH₃CNaq) to afford the title compound (0.70 g, 96%) as a colorless amorphous powdery product.

IR ν max cm⁻¹ (KBr): 3320, 2970, 2920, 1730, 1640, 1560, 1500, 1445, 1360, 1250, 1155 NMR(CD₃OD) δ: 1.42(9H,s), 1.48(9H,s), 1.02–2.17(4H,m), 2.90–3.20(2H,m), 3.36–4.64(6H,m), 4.00(1H,d,J=17.5 Hz), 4.12(1H,d,J=17.5 Hz), 4.82–5.03(1H,m), 7.38(2H,d,J=8.6 Hz), 7.97(2H,d,J=8.6 Hz).

Reference Example 98

(S)-[3-(3-t-butoxycarbonylaminopropyl)-4-[[4-(1,3-dimethoxycarbonylguanidino)benzoylamino]acetyl]-2-oxopiperazin-1-yl]acetic acid t-butyl ester (another name: (S)-3-(3-t-butoxycarbonylaminopropyl)-4-[[4-(1,3-dimethoxycarbonylguanidino)benzoylamino]-acetyl]-2-oxopiperazine-1-acetic acid t-butyl ester)

In a mixture of 1,4-dioxane (7.0 ml) and H₂O (7.0 ml) was dissolved (S)-[3-(3-t-butoxycarbonylaminopropyl)-4-[(4-guanidinobenzoylamino)acetyl]-2-oxopiperazin-1-yl]acetic acid t-butyl ester (another name: (S)-3-(3-t-butoxycarbonylaminopropyl)-4-[(4-guanidinobenzoylamino)acetyl)-2-oxopiperazine-1-acetic acid t-butyl ester) (0.70 g, 1.19 mmol) produced in Reference Example 97. To the solution was added gradually, with stirring at 0° C., while keeping the pH of the reaction system at 10 or below, a 2N aqueous solution of sodium hydroxide (4.20 ml, 8.33 mmol) and chlorocarbonic acid methyl ester (0.46 ml, 5.94 mmol). The mixture was stirred for 30 minutes at 0° C., then the reaction mixture was adjusted to pH 4 with a 1N aqueous solution of hydrochloric acid, and the resulting mixture was extracted with ethyl acetate. The organic layer was dried over anhydrous magnesium sulfate and concentrated under reduced pressure. The concentrate was purified by means of silica gel column chromatography (ethyl acetate/methanol=13/1) to afford the title compound (0.67 g, 80%) as a colorless amorphous powdery product.

IR ν max cm⁻¹ (KBr): 3380, 2970, 1730, 1640, 1490, 1433, 1362, 1250, 1155 NMR(CD₃OD) δ: 1.42(9H,s), 1.48 (9H,s), 1.30–2.15(4H,m), 2.98–3.20(2H,m), 3.45(3H,s), 3.72(3H,s), 3.34–4.70(8H,m), 4.85–5.05(1H,m), 7.32(2H,d, J=8.5 Hz), 7.91(2H,d,J=8.5 Hz).

Reference Example 99

(S)-[3-(3-t-butoxycarbonylaminopropyl)-4-[[4-(3-methoxycarbonylguanidino)benzoylamino]acetyl]-2-oxopiperazin-1-yl]acetic acid t-butyl ester (another name: (S)-3-(3-t-butoxycarbonylaminopropyl)-4-[[4-(3-methoxycarbonylguanidino)benzoylamino]acetyl]-2-oxopiperazine-1-acetic acid t-butyl ester)

In a mixture of methanol (6.7 ml) and H₂O (0.67 ml) was dissolved (S)-[3-(3-t-butoxycarbonylaminopropyl)-4-[[4-(1,3-dimethoxycarbonylguanidino)benzoylamino]acetyl]-2-oxopiperazin-1-yl]acetic acid t-butyl ester (another name: (S)-3-(3-t-butoxycarbonylaminopropyl)-4-[[4-(1,3-dimethoxycarbonylguanidino)benzoylamino]acetyl]-2-oxopiperazine-1-acetic acid t-butyl ester) (0.67 g, 0.95 mmol) produced in Reference Example 98. To the solution was added, under ice-cooling, lithium hydroxide-1.0 hydrate (45.8 mg, 1.09 mmol). The mixture was stirred for 30 minutes at 0° C., and the pH of the reaction mixture was adjusted to pH 4 with a 1N aqueous solution of hydrochloric acid, then concentrated under reduced pressure. The concentrate was purified by means of silica gel column chromatography (ethyl acetate/methanol=10/1-5/1) to afford the title compound (0.44 g, 72%) as a colorless amorphous powdery product.

IR ν max cm$^{-1}$ (KBr): 3390, 2970, 2925, 1730, 1640, 1525, 1435, 1360, 1240, 1155 NMR(CD$_3$OD) δ: 1.42(9H,s), 1.47(9H,s), 1.20–2.14(4H,m), 2.96–3.18(2H,m), 3.68(3H,s), 3.98(1H,d,J=17.4 Hz), 4.12(1H,d,J=17.4 Hz), 3.22–4.66 (6H,m), 4.82–5.04(1H,m), 7.45(2H,d,J=8.6 Hz), 7.86(2H,d, J=8.6 Hz).

Reference Example 100

(S)-[3-[3-(4-guanidinobenzoylamino)propyl]-4-[[4-(3-methoxycarbonylguanidino)benzoylamino]acetyl]-2-oxopiperazin-1-yl]acetic acid trifluoroacetate (another name: (S)-3-[3-(4-guanidinobenzoylamino)propyl]-4-[[4-(3-methoxycarbonylguanidino)benzoylamino]acetyl]-2-oxopiperazine-1-acetic acid trifluoroacetate)

In methylene chloride (4.4 ml) was dissolved (S)-[3-(3-t-butoxycarbonylaminopropyl)-4-[[4-(3-methoxycarbonylguanidino)benzoylamino]acetyl]-2-oxopiperazin-1-yl]acetic acid t-butyl ester (another name: (S)-3-(3-t-butoxycarbonylaminopropyl)-4-[[4-(3-methoxycarbonylguanidino)benzoylamino]acetyl]-2-oxopiperazine- 1-acetic acid t-butyl ester) (0.44 g, 0.68 mmol) produced in Reference Example 99. To the solution was added, with stirring at room temperature, trifluoroacetic acid (4.4 ml). One hour later, the reaction mixture was concentrated under reduced pressure then dissolved in a mixture of 1,4-dioxane (4.4 ml) and H$_2$O (4.4 ml). To this solution was added, at room temperature, 4-guanidinobenzoic acid N-hydroxy-5-norbornene-2,3-dicarboximide ester (0.31 g, 0.82 mmol) and sodium hydrogen carbonate (0.29 g, 3.40 mmol). One hour later, the PH of the reaction was adjusted to pH 2 with a 1N aqueous solution of hydrochloric acid, and the resulting mixture was concentrated under reduced pressure. The concentrate was purified by means of column chromatography [(CHP-20, H$_2$O-5% CH$_3$CNaq-10% CH$_3$CNaq-15% CH$_3$CNaq) and (LH-20, H$_2$O)] to afford the title compound (0.18 g, 32%) as a colorless amorphous powdery product.

Specific optical rotation: $[\alpha]_D^{20}$ +46.9° (C=0.976, MeOH)

Elemental Analysis for C$_{29}$H$_{36}$N$_{10}$O$_8$·1.0CF$_3$CO$_2$H·3.0H$_2$O (820.737): Calcd.: C, 45.37; H, 5.28; N, 17.07 Found: C, 45.42; H, 5.08; N, 16.92.

The present invention provides, by dispersing and atomizing an amorphous water-soluble 2-piperazinone-1-acetic acid compound in a polymer solution, a sustained-release microcapsule containing the compound in high concentration with low initial drug release. Furthermore, use of this microcapsule can reduce undesirable side effects such as hemorrhage caused by a high initial release of the above compound, and can be useful for the prophylaxis or treatment of thrombosis, angina pectoris, unstable angina or ischemic complication, reobstruction or restenosis after percutaneous transluminal coronary angioplasty or coronary thrombolytic therapy.

We claim:

1. A sustained release microcapsule, comprising:
   (a) a pharmaceutically effective compound comprising an amorphous water-soluble 2-piperazinone-1-acetic acid compound of formula (I) or a salt thereof:

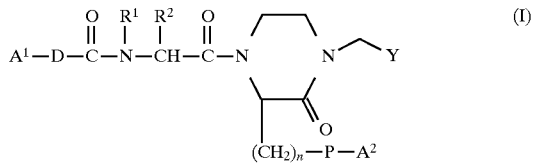

wherein

A$^1$ and A$^2$ independently are a group having a nitrogen atom capable of being positively charged or optionally substituted amidoxime, optionally substituted oxadiazolyl or optionally substituted thiadiazolyl;

D is a 2- to 6-atom chain optionally bonded through a hereto-atom or a 5- or 6-membered carbocyclic ring or heterocyclic ring having 1 to 4 N, O or S hetero-atoms provided that depending on the bonding position of said 5- or 6-membered ring, said ring is counted as a 2- or 3-atom chain in said 2- to 6-atom chain;

R$^1$ is a hydrogen atom or a hydrocarbon group;

R$^2$ is (1) hydrogen atom or (2) a C$_{1-4}$ alkyl group which may be substituted with an optionally substituted phenyl group optionally substituted with C$_{1-4}$ alkoxy, hydroxyl group or carbamoyl group, or R$^1$ and R$^2$ may be joined together to form a 5- or 6-membered ring;

P is a 1- to 10-carbon atom chain optionally bonded through a hereto-atom or 5- or 6-membered carbocyclic ring or heterocyclic ring having 1 to 4 N, O or S hetero-atoms provided that depending on the bonding position of said 5- or 6-membered ring, said ring is counted as a 2- or 3-atom chain in said 1- to 10-carbon atom chain;

Y is (1) a carboxyl group which is optionally esterified with optionally substituted alkoxy, alkenyloxy or benzyloxy, or —OCH(R$^{7a}$)OCOR$^8$ wherein R$^{7a}$ is hydrogen, straight-chain or branched lower alkyl, or C$_{5-7}$ cycloalkyl and R$^8$ is straight-chain or branched lower alkyl, lower alkenyl, C$_{5-7}$ cycloalkyl, lower alkyl substituted with C$_{5-7}$ cycloalkyl or optionally substituted C$_{6-12}$ aryl, lower alkenyl substituted with C$_{5-7}$ cycloalkyl or optionally substituted C$_{6-12}$ aryl, optionally substituted aryl, straight-chain or branched lower alkoxy, straight chain or branched lower alkenyloxy, C$_{5-7}$ cycloalkyloxy, lower alkoxy substituted with C$_{5-7}$ cycloalkyl or optionally substituted C$_{6-12}$ aryl, lower alkenyloxy substituted with C$_{5-7}$ cycloalkyl or optionally substituted C$_{6-12}$ aryl, or optionally substituted C$_{6-12}$ aryloxy, or (2) an optionally amidated carboxyl group; and n denotes an integer of 0 to 8; and (b) a pharmacologically acceptable polymer binder.

2. A microcapsule of claim 1, wherein the 2-piperazinone-1-acetic acid compound or salt thereof is dispersed in the polymer.

3. A microcapsule of claim 1, wherein the water-solubility of the 2-piperazinone-1-acetic acid compound or salt thereof is not less than about 1 g/100 ml at 20 C°.

4. A microcapsule of claim 1, wherein the average particle size of the 2-piperazinone-1-acetic acid compound or salt thereof is not more than about 30 μm.

5. A microcapsule of claim 1, wherein the average particle size of the 2-piperazinone-1-acetic acid compound or salt thereof is not more than about 5 μm.

6. A microcapsule of claim 1, wherein the 2-piperazinone-1-acetic acid compound is (S)-4-(4-guanidinobenzoyl-amino)acetyl-3-[3-(4-guanidinobenzoylamino)]propyl-2-oxopiperazine-1-acetic acid.

7. A microcapsule of claim 1, which comprises (S)-4-(4-guanidinobenzoylamino)acetyl-3-[3-(4-guanidinobenzoylamino)]propyl-2-oxopiperazine-1-acetic acid hydrochloride.

8. A microcapsule of claim 1, wherein the 2-piperazinone-1-acetic acid compound is (S)-4-(4-amidinobenzoyl)aminoacetyl-3-{3-(4-amidinobenzoyl)amino}propyl-2-oxopiperazine-1-acetic acid.

9. A microcapsule of claim 1, which comprises (S)-4-(4-amidinobenzoyl)aminoacetyl-3-{3-(4-amidinobenzoyl)amino}propyl-2-oxopiperazine-1-acetic acid trifluoroacetate.

10. A microcapsule of claim 1, wherein the 2-piperazinone-1-acetic acid compound is (S)-4-[4-(2-aminoethyl)benzoylamino)acetyl-3-[3-(4-amidinobenzoylamino)]propyl-2-oxopiperazine-1-acetic acid.

11. A microcapsule of claim 1, wherein the 2-piperazinone-1-acetic acid compound is (S)-4-(4-amidinobenzoylamino)acetyl-3-[2-(4-guanidinobenzoylamino)]ethyl-2-oxopiperazine-1-acetic acid.

12. A microcapsule of claim 1, wherein the 2-piperazinone-1-acetic acid compound is (S)-4-(4-amidinobenzoyl)aminoacetyl-3-[3-( 4-guanidinobutanoylamino)]propyl-2-oxopiperazine-1-acetic acid.

13. A microcapsule of claim 1, wherein the polymer is a biodegradable polymer.

14. A microcapsule of claim 13, wherein the biodegradable polymer is a polyester.

15. A microcapsule of claim 14, wherein the polyester is a lactic acid/glycolic acid copolymer or homopolymer.

16. A microcapsule of claim 15, wherein the molar ratio of lactic acid/glycolic acid of the copolymer or homopolymer is from about 100/0 to about 25/75.

17. A microcapsule of claim 15, wherein the weight average molecular weight of the lactic acid/glycolic acid copolymer or homopolymer is from about 5000 to about 30000.

18. A microcapsule of claim 14, wherein the polyester is hydroxybutyric acid/glycolic acid copolymer or homopolymer.

19. A microcapsule of claim 18, wherein the molar ratio of hydroxybutyric acid/glycolic acid of the copolymer or homopolymer is from about 100/0 to about 25/75.

20. A microcapsule of claim 18, wherein the weight average molecular weight of the hydroxybutyric acid/glycolic acid of the copolymer or homopolymer is from about 5000 to about 25000.

21. A method of treatment of diseases in the circulatory system, comprising the steps of:
   selecting a patient in need thereof; and
   administering to said patient a microcapsule of claim 1.

22. A method of treatment of thrombosis, angina pectoris, unstable angina or ischemic complication, reobstruction or restenosis after percutaneous transluminal coronary angioplasty or coronary thrombolytic therapy, comprising the steps of:
   selecting a patient in need thereof; and
   administering to said patient a microcapsule of claim 1.

23. A microcapsule which is produced by the steps of:
   selecting a dispersion of an amorphous water-soluble 2-piperazinone-1-acetic acid compound of the formula (I) or salt thereof as defined in claim 1;
   selecting a solution of a polymer in an organic solvent;
   dispersing in aqueous phase said dispersion of amorphous water-soluble 2-piperazinone-1-acetic acid or salt thereof and said polymer solution in organic solvent to obtain a solid/oil/water (s/o/w) emulsion; and
   subjecting the s/o/w emulsion to in-water drying.

24. A microcapsule of claim 23, wherein the concentration of the 2-piperazinone-1-acetic acid compound or salt thereof in the solution of a polymer in an organic solvent is from about 0.01 to about 75% (w/w).

25. A microcapsule of claim 23, wherein the solution of a polymer in an organic solvent further contains a basic compound, or oil or fat.

26. A microcapsule of claim 25, wherein the basic compound is a basic amino acid.

27. A microcapsule of claim 25, wherein the basic compound is L-arginine, L-lysine or N-methylglucamine.

28. A microcapsule of claim 25, wherein the concentration of the basic compound, or oil or fat in the solution of a polymer in an organic solvent is from about 0.1 to about 3% (w/w).

29. A microcapsule of claim 23, wherein the aqueous phase further contains an osmotic pressure adjustor.

30. A microcapsule of claim 29, wherein the osmotic pressure adjustor is a sodium chloride.

31. A method of producing a microcapsule, which comprises the steps of:
   selecting a dispersion of an amorphous water-soluble 2-piperazinone-1-acetic acid compound of the formula (I) or salt thereof as defined in claim 1;
   selecting a solution of a polymer in an organic solvent;
   dispersing in aqueous phase said dispersion of amorphous water-soluble 2-piperazinone-1-acetic acid or salt thereof and said polymer solution in organic solvent to obtain a solid/oil/water (s/o/w) emulsion; and
   subjecting the s/o/w emulsion to in-water drying.

32. A method according to claim 24, wherein said patient is a mammal.

* * * * *

UNITED STATES PATENT AND TRADEMARK OFFICE
CERTIFICATE OF CORRECTION

PATENT NO. : 5,876,756
DATED : March 2, 1999
INVENTOR(S): SHIGEYUKI TAKADA, ET AL.

It is certified that error appears in the above-identified patent and that said Letters Patent is hereby corrected as shown below:

<u>ON COVER PAGE AT [54] TITLE</u>

"MICROCAPSULE" should read --SUSTAINED RELEASE MICROCAPSULE--.

<u>COLUMN 1</u>

Line 1, Title, "MICROCAPSULE" should read --SUSTAINED RELEASE MICROCAPSULE--;
Line 7, "field" should read --filed--.

<u>COLUMN 3</u>

Line 52, "namely, (2)" should read --namely, ¶(2)--.

<u>COLUMN 4</u>

Formula (1), "(i)" should be deleted;
Line 38, "(10)" should read --¶ (10)--;
Line 46, "above ," should read --above,--;
Line 58, insert --D is--.

<u>COLUMN 6</u>

Line 19, "atom" should read --atoms--.

UNITED STATES PATENT AND TRADEMARK OFFICE
CERTIFICATE OF CORRECTION

PATENT NO. : 5,876,756

DATED : March 2, 1999

INVENTOR(S): SHIGEYUKI TAKADA, ET AL.

It is certified that error appears in the above-identified patent and that said Letters Patent is hereby corrected as shown below:

COLUMN 8

Line 4, "examples" should read --examples of--.

COLUMN 9

Line 4, "example" should read --examples--;
Line 10, "groups" should read --groups,--;
Line 20, "A'" should read --A' and--;
Line 26, "a interval" should --an interval--; and no ¶ indent for line;
Line 27, no ¶ indent for line;
Line 32, "be" should read --be a--.

COLUMN 10

Line 31, "Example" should read --Examples--;
Formula 3, "$\overset{\|}{O}$" should read --$\overset{\|}{O}$.--.

COLUMN 11

Line 25, "(in" should read --(In--;
Line 25, "A')." should read --A'.)--;
Line 32, "(e.g.propargyl," should read --(e.g. propargyl,--.

COLUMN 12

Line 45, "ring," should read --ring--.

UNITED STATES PATENT AND TRADEMARK OFFICE
CERTIFICATE OF CORRECTION

PATENT NO. : 5,876,756

DATED : March 2, 1999

INVENTOR(S): SHIGEYUKI TAKADA, ET AL.

It is certified that error appears in the above-identified patent and that said Letters Patent is hereby corrected as shown below:

COLUMN 13

Line 10, "on e" should read --one--.

COLUMN 14

Line 63, "groups" should read --group--.

COLUMN 16

Line 13, "$R^2$" should read --$R^1$--;
Line 43, "hydrogen," should read --hydrogen;--;
Line 46, "from," should read --from--.

COLUMN 18

Formula 3,

"" (second occurrence) should read --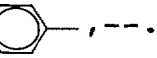,--.

COLUMN 20

Line 33, "ethyl)" should read --ethyl]--;
Line 61, "oxopiperazine" should read --oxopiperazin--.

COLUMN 21

Line 28, "oxopiperazine" should read --oxopiperazin--.

UNITED STATES PATENT AND TRADEMARK OFFICE
CERTIFICATE OF CORRECTION

PATENT NO. : 5,876,756

DATED : March 2, 1999

INVENTOR(S): SHIGEYUKI TAKADA, ET AL.

It is certified that error appears in the above-identified patent and that said Letters Patent is hereby corrected as shown below:

COLUMN 22

Line 6, "above or," should read --above, or--.

COLUMN 25

Line 49, "stating," should read --stated,--.

COLUMN 26

Line 49, "the" should read --where the--;
Line 53, "methanol" should read --methanol,--; and "And," should read --And, with--;
Line 55 "subjecting" should read --being subjected--.

COLUMN 28

Line 67, "acid2" should read --acid. 2--.

COLUMN 29

Line 29, "about" (2nd occurrence) should be deleted.

COLUMN 31

Line 60, "preferable" should read --preferably--.

COLUMN 32

Line 21, "by," should read --by--;
Line 23, "or," should read --or--.

UNITED STATES PATENT AND TRADEMARK OFFICE
CERTIFICATE OF CORRECTION

PATENT NO. : 5,876,756

DATED : March 2, 1999

INVENTOR(S): SHIGEYUKI TAKADA, ET AL.

It is certified that error appears in the above-identified patent and that said Letters Patent is hereby corrected as shown below:

COLUMN 33

Line 12, "suspension." should read --suspension;--;
Line 13, "being" should read --are--;
Line 55, "Any" should read --As regards--.

COLUMN 34

Line 10, "receptos" should read --receptors--.

COLUMN 35

Line 7, "When" should read --when--;
Line 14, "500 mg" should read --500 mg,--;
Line 19, "administer" should read --administered--.
Line 36, "1(2)" should read --(2)--.

COLUMN 36

Line 11, "Smitzerland)" should read --Switzerland)--;
Line 40, "A. W/O/W" should read --A. ¶ W/O/W--.

COLUMN 39

Line 18, "O $_5$" should read --$O_5$--;
Line 37, "+41.90°" should read --+41.9°--.

COLUMN 40

Line 8, "+46.80°" should read --46.8°--.

UNITED STATES PATENT AND TRADEMARK OFFICE
CERTIFICATE OF CORRECTION

PATENT NO. : 5,876,756

DATED : March 2, 1999

INVENTOR(S): SHIGEYUKI TAKADA, ET AL.

It is certified that error appears in the above-identified patent and that said Letters Patent is hereby corrected as shown below:

COLUMN 41

Line 51, "was" should read --and was--.

COLUMN 42

Line 30, "]α]$_D$" should read --[α]$_D$--.

COLUMN 45

Line 58, "ox-opiperazine" should read --oxopiperazine--.

COLUMN 46

Line 9, "H70)" should read --H$_2$O)--;
Line 17, "N-t-" should read --N$^4$-t---.

COLUMN 47

Line 12, "Jethyl-" should read --]ethyl--;
Line 30, "with" should read --while--.

COLUMN 49

Line 2, "-3-(3-(4-" should read ---3-[3-4---;
Line 11, "+48.60°" should read --+48.6°--.

UNITED STATES PATENT AND TRADEMARK OFFICE
CERTIFICATE OF CORRECTION

PATENT NO. : 5,876,756
DATED : March 2, 1999
INVENTOR(S): SHIGEYUKI TAKADA, ET AL.

It is certified that error appears in the above-identified patent and that said Letters Patent is hereby corrected as shown below:

COLUMN 50

Line 63, "benzoylaminojacetyl" should read
--benzoylamino]acetyl--;
Line 64, "benzoylaminoj}propyl" should read
--benzoylamino]}propyl--.

COLUMN 51

Line 38, "$H_3$," should read --$H_{31}$--.

COLUMN 52

Line 57, "methxoycarbonyloxyiminomethyl)" should read
--methoxycarbonyloxyiminomethyl)--.

COLUMN 54

Line 19, "recrystallizated" should read --recrystallized--.

COLUMN 56

Line 30, "N,12.5." should read --N.12.52.--;
Line 59, "was added" (1st occurrence) should be deleted;
"ther esidue" should read --the residue--;
Line 62, "recrystallizated" should read --recrystallized--.

UNITED STATES PATENT AND TRADEMARK OFFICE
CERTIFICATE OF CORRECTION

PATENT NO. : 5,876,756

DATED : March 2, 1999

INVENTOR(S): SHIGEYUKI TAKADA, ET AL.

It is certified that error appears in the above-identified patent and that said Letters Patent is hereby corrected as shown below:

COLUMN 58

Line 49, "to" should be deleted.

COLUMN 59

Line 23, "2HCl H$_2$O:" should read --2HCl·H$_2$O:--.

COLUMN 60

Line 52, "ester-oxalate" should read --ester·oxalate--;
Line 54, "ester-oxalate" should read --ester·oxalate--.

COLUMN 62

Line 9, "benzyloxycarboaylamino- 3" should read
 --benzyloxycarbonylamino-3--.
Line 43, "[5,2,1,0" should read --[5,2,1,0,--.

COLUMN 63

Line 58, "'HNMR" should read 'H-NMR--.

COLUMN 64

Line 8, "oxadiazol -3" should read --oxadiazol-3--;
Line 19, "in" should be deleted.

UNITED STATES PATENT AND TRADEMARK OFFICE
CERTIFICATE OF CORRECTION

PATENT NO. : 5,876,756
DATED : March 2, 1999
INVENTOR(S): SHIGEYUKI TAKADA, ET AL.

Page 9 of 10

It is certified that error appears in the above-identified patent and that said Letters Patent is hereby corrected as shown below:

COLUMN 65

Line 4, "oxadiazol -3" should read --oxadiazol-3--.

COLUMN 66

Line 43, [5,2,1,0" should read --[5,2,1,0,--;
Line 64, "amidinobenzoyl-amino)" should read
  --amidinobenzoylamino)--.

COLUMN 67

Line 7, "ther eaction" should read --the reaction--.

COLUMN 68

Line 11, "To the" should read --The--.

UNITED STATES PATENT AND TRADEMARK OFFICE
CERTIFICATE OF CORRECTION

PATENT NO. : 5,876,756

DATED : March 2, 1999

INVENTOR(S): SHIGEYUKI TAKADA, ET AL.

It is certified that error appears in the above-identified patent and that said Letters Patent is hereby corrected as shown below:

COLUMN 72

Line 23, "acetyl)" should read --acetyl]--;
Line 59, "hydroxide-1.0" should read --hydroxide·1.0--.

COLUMN 76

Line 47, "24," should read --22,--.

Signed and Sealed this

Eighth Day of February, 2000

Attest:

Q. TODD DICKINSON

Attesting Officer

Commissioner of Patents and Trademarks